(12) United States Patent
Bjorn et al.

(10) Patent No.: US 7,282,347 B2
(45) Date of Patent: Oct. 16, 2007

(54) METHOD FOR EXTRACTING QUANTITATIVE INFORMATION RELATING TO INTERACTIONS BETWEEN CELLULAR COMPONENTS

(75) Inventors: Sara Petersen Bjorn, Lyngby (DK); Ole Thastrup, Birkerod (DK); Bernard Robert Terry, Frederiksberg (DK); Grith Hagel, Dragor (DK); Soren Jensby Nielsen, Lyngby (DK)

(73) Assignee: Fisher Bioimage APS, Soborg (DK)

( * ) Notice: Subject to any disclaimer, the term of this patent is extended or adjusted under 35 U.S.C. 154(b) by 327 days.

(21) Appl. No.: 10/332,065

(22) PCT Filed: Jul. 3, 2001

(86) PCT No.: PCT/DK01/00466

§ 371 (c)(1),
(2), (4) Date: Mar. 14, 2003

(87) PCT Pub. No.: WO02/03072

PCT Pub. Date: Jan. 10, 2002

(65) Prior Publication Data

US 2004/0018504 A1 Jan. 29, 2004

(30) Foreign Application Priority Data

Jul. 4, 2000 (DK) ............................ 2000 01041
May 16, 2001 (DK) ............................ 2001 00775

(51) Int. Cl.
*C07H 21/04* (2006.01)
*C12Q 1/68* (2006.01)
*C12N 9/12* (2006.01)
*C12N 5/06* (2006.01)

(52) U.S. Cl. .................. 435/7.6; 435/196; 435/69.7; 435/6; 435/325; 435/7.1; 435/7.8; 435/19; 435/194

(58) Field of Classification Search .................. 435/6, 435/7.1, 69.1, 69.7
See application file for complete search history.

(56) References Cited

U.S. PATENT DOCUMENTS 5,597,688 A  1/1997  Connelly et al.
5,686,261 A  11/1997 Zhang et al.
2003/0187056 A1* 10/2003 Terry et al. ................. 514/424

FOREIGN PATENT DOCUMENTS

| EP | 0 743 519 A | 11/1996 |
| WO | WO96 25486 A | 8/1996 |
| WO | WO98 45704 A | 10/1998 |
| WO | WO 00/17221 | * 3/2000 |
| WO | WO 00 17221 A | 3/2000 |
| WO | WO 00 23615 A | 4/2000 |

OTHER PUBLICATIONS

Housley et al. www.Drugdiscoverytoday.com vol. 10, Nov. 2005 1503-1519.*
Sakai, Norio et al., "Direct visualization of the translocation of the gamma-subspecies of protein kinase C in living cells using fusion proteins with green fluorescent protein", The Journal of Cell Biology, vol. 139, No. 139, pp. 1465-1476, Dec. 1997.

* cited by examiner

*Primary Examiner*—Rebecca E. Prouty
*Assistant Examiner*—Md. Y. Meah
(74) *Attorney, Agent, or Firm*—Workman Nydegger

(57) ABSTRACT

A method is described to assay for protein interactions in living cells, e.g. by the introduction of two heterologous conjugates into the cell. The method uses the measurement of cellular distribution of a detectable component (e.g. a GFP-labeled~fluorescent probe) to indicate the presence or absence of an interaction between that component and a second component of interest. The method uses the knowledge that certain components can be stimulated to redistribute within the cell to defined locations. Inducible redistribution systems make it possible to determine if specific interactions occur between components. Inducible systems are described where it is demonstrated that the redistribution stimuli are essentially "null", in that they affect no other system in the cell during the assay period, other than the component whose redistribution can be induced. Also described is an extraction buffer which is useful in high throughput screening for drugs which affect the intracellular distribution of intracellular components. The extraction buffer comprises a cellular fixation agent and cellular permeabilisation agent. Optimizing the composition of the extraction buffer and its application to various cell types is described.

13 Claims, 20 Drawing Sheets

Figure 1:

Fig. 13
Fig. 13a
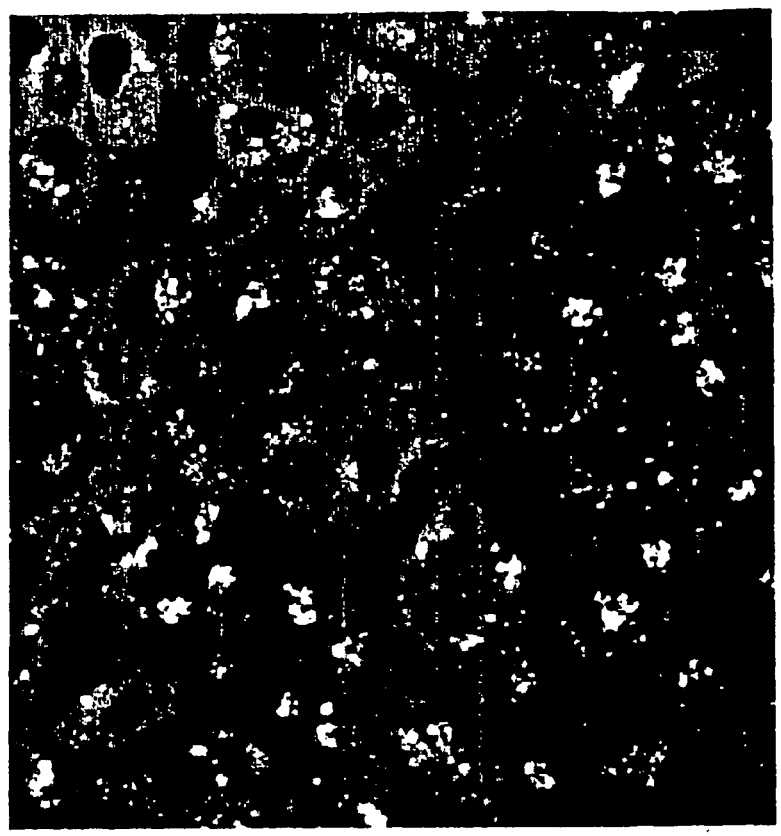
Fig. 13b
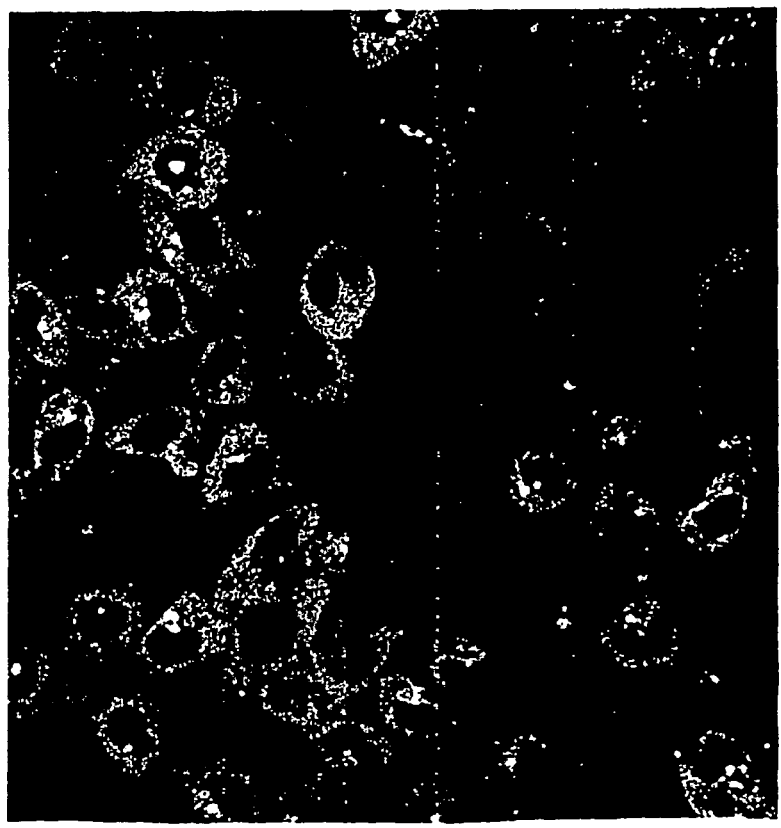

4A4-14-3-3b + EGFP-BAD

Non stimulated cells

Non extracted cells

Extracted cells

Stimulated cells

Non extracted cells

Extracted cells

Non stimulated cells
Before extraction <span></span> After extraction

Stimulated cells (Il-1 1ng/ml)
Before extraction <span></span> After extraction

SEQUENCE LISTING

<160> NUMBER OF SEQ ID NOS: 29
<210> SEQ ID NO 1
<211> LENGTH: 2666
<212> TYPE: DNA
<213> ORGANISM: Aequoria Victoria and Homo sapiens

<400> SEQUENCE: 1

| | | | | | |
|---|---|---|---|---|---|
| atggaacccc | cgaccgtccc | ctcggaaagg | agcctgtctc | tgtcactgcc | cgggccccgg | 60 |
| gagggccagg | ccaccctgaa | gcctcccccg | cagcacctgt | ggcggcagcc | tcggacccc | 120 |
| atccgtatcc | agcagcgcgg | ctactccgac | agcgcggagc | gcgccgagcg | ggagcggcag | 180 |
| ccgcaccggc | ccatagagcg | cgccgatgcc | atggacacca | gcgaccggcc | cggcctgcgc | 240 |
| acgacccgca | tgtcctggcc | ctcgtccttc | catggcactg | gcaccggcag | cggcggcgcg | 300 |
| ggcggaggca | gcagcaggcg | cttcgaggca | gagaatgggc | cgacaccatc | tcctggccgc | 360 |
| agcccctgg | actcgcaggc | gagcccagga | ctcgtgctgc | acgccggggc | ggccaccagc | 420 |
| cagcgccggg | agtccttcct | gtaccgctca | gacagcgact | atgacatgtc | acccaagacc | 480 |
| atgtcccgga | actcatcggt | caccagcgag | gcgcacgctg | aagacctcat | cgtaacacca | 540 |
| tttgctcagg | tgctggccag | cctccggagc | gtccgtagca | acttctcact | cctgaccaat | 600 |
| gtgcccgttc | ccagtaacaa | gcggtccccg | ctgggcggcc | ccaccctgt | ctgcaaggcc | 660 |
| acgctgtcag | aagaaacgtg | tcagcagttg | gcccgggaga | ctctggagga | gctggactgg | 720 |
| tgtctggagc | agctggagac | catgcagacc | tatcgctctg | tcagcgagat | ggcctcgcac | 780 |
| aagtttaaaa | ggatgttgaa | ccgtgagctc | acacacctgt | cagaaatgag | caggtccgga | 840 |
| aaccaggtct | cagagtacat | ttccacaaca | ttcctggaca | aacagaatga | agtggagatc | 900 |
| ccatcaccca | cgatgaagga | acgagaaaaa | cagcaagcgc | cgcgaccaag | accctcccag | 960 |
| ccgcccccgc | cccctgtacc | acacttacag | cccatgtccc | aaatcacagg | gttgaaaaag | 1020 |
| ttgatgcata | gtaacagcct | gaacaactct | aacattcccc | gatttggggt | gaagaccgat | 1080 |
| caagaagagc | tcctggccca | agaactggag | aacctgaaca | gtggggcct | gaacatcttt | 1140 |
| tgcgtgtcgg | attacgctgg | aggccgctca | ctcacctgca | tcatgtacat | gatattccag | 1200 |
| gagcgggacc | tgctgaagaa | attccgcatc | ccggtggaca | cgatggtgac | atacatgctg | 1260 |
| acgctggagg | atcactacca | cgctgacgtg | gcctaccata | cagcctgca | cgcagctgac | 1320 |
| gtgctgcagt | ccacccacgt | actgctggcc | acgcctgcac | tagatgcagt | gttcacggac | 1380 |
| ctggagattc | tcgccgccct | cttcgcggct | gccatccacg | atgtggatca | ccctggggtc | 1440 |
| tccaaccagt | tcctcatcaa | caccaattcg | gagctggcgc | tcatgtacaa | cgatgagtcg | 1500 |
| gtgctcgaga | tcaccaccct | ggccgtgggc | ttcaagctgc | tgcaggagga | caactgcgac | 1560 |
| atcttccaga | acctcagcaa | gcgccagcgg | cagagcctac | gcaagatggt | catcgacatg | 1620 |
| gtgctggcca | cggacatgtc | caagcacatg | accctcctgg | ctgacctgaa | gaccatggtg | 1680 |
| gagaccaaga | aagtgaccag | ctcaggggtc | ctcctgctag | ataactactc | cgaccgcatc | 1740 |
| caggtcctcc | ggaacatggt | gcactgtgcc | gacctcagca | ccccaccaa | gccgctggag | 1800 |
| ctgtaccgcc | agtggacaga | ccgcatcatg | gccgagttct | tccagcaggg | tgaccgagag | 1860 |
| cgcgagcgtg | gcatggaaat | cagccccatg | tgtgacaagc | acactgcctc | cgtggagaag | 1920 |
| tctcaggtgg | gttttattga | ctacattgtg | cacccattgt | gggagacctg | gcggaccttt | 1980 |
| gtccacccag | atgcccagga | gatcttggac | actttggagg | acaaccggga | ctggtactac | 2040 |

-continued

```
agcgccatcc ggcagagccc atctccgcca cccgaggagg agtcaagggg gccaggccac    2100
ccacccctgc ctgacaagtt ccagtttgag ctgacgctgg aggaggaaga ggaggaagaa    2160
atatcaatgg cccagatacc gtgcacagcc aagaggcat tgactgcgca gggattgtca     2220
ggagtcgagg aagctctgga tgcaaccata gcctgggagg catccccggc ccaggagtcg    2280
ttggaagtta tggcacagga agcatccctg gaggccgagc tggaggcagt gtatttgaca    2340
cagcaggcac agtccacagg cagtgcacct gtggctccgg atgagttctc gtcccgggag    2400
gaattcgtgg ttgctgtaag ccacagcagc ccctctgccc tggctcttca agccccctt    2460 ctccctgctt ggaggaccct gtctgtttca gagcatgccc cgggcctccc gggcctcccc    2520
tccacggcgg ccgaggtgga ggcccaacga gagcaccagg ctgccaagag ggcttgcagt    2580
gcctgcgcag ggacatttgg ggaggacaca tccgcactcc cagctcctgg tggcgggggg    2640
tcaggtggag accctacctg ggatcc                                         2666
```

<210> SEQ ID NO 2
<211> LENGTH: 886
<212> TYPE: PRT
<213> ORGANISM: Aequoria victoria and Homo sapiens

<400> SEQUENCE: 2

```
Met Glu Pro Pro Thr Val Pro Ser Glu Arg Ser Leu Ser Leu Ser Leu
 1               5                  10                  15

Pro Gly Pro Arg Glu Gly Gln Ala Thr Leu Lys Pro Pro Gln His
                20                  25                  30

Leu Trp Arg Gln Pro Arg Thr Pro Ile Arg Ile Gln Gln Arg Gly Tyr
            35                  40                  45

Ser Asp Ser Ala Glu Arg Ala Glu Arg Glu Arg Gln Pro His Arg Pro
        50                  55                  60

Ile Glu Arg Ala Asp Ala Met Asp Thr Ser Asp Arg Pro Gly Leu Arg
 65                  70                  75                  80

Thr Thr Arg Met Ser Trp Pro Ser Ser Phe His Gly Thr Gly Thr Gly
                 85                  90                  95

Ser Gly Gly Ala Gly Gly Gly Ser Ser Arg Arg Phe Glu Ala Glu Asn
                100                 105                 110

Gly Pro Thr Pro Ser Pro Gly Arg Ser Pro Leu Asp Ser Gln Ala Ser
            115                 120                 125

Pro Gly Leu Val Leu His Ala Gly Ala Ala Thr Ser Gln Arg Arg Glu
        130                 135                 140

Ser Phe Leu Tyr Arg Ser Asp Ser Asp Tyr Asp Met Ser Pro Lys Thr
145                 150                 155                 160

Met Ser Arg Asn Ser Ser Val Thr Ser Glu Ala His Ala Glu Asp Leu
                165                 170                 175

Ile Val Thr Pro Phe Ala Gln Val Leu Ala Ser Leu Arg Ser Val Arg
            180                 185                 190

Ser Asn Phe Ser Leu Leu Thr Asn Val Pro Val Pro Ser Asn Lys Arg
        195                 200                 205

Ser Pro Leu Gly Gly Pro Thr Pro Val Cys Lys Ala Thr Leu Ser Glu
    210                 215                 220

Glu Thr Cys Gln Gln Leu Ala Arg Glu Thr Leu Glu Glu Leu Asp Trp
225                 230                 235                 240

Cys Leu Glu Gln Leu Glu Thr Met Gln Thr Tyr Arg Ser Val Ser Glu
                245                 250                 255

Met Ala Ser His Lys Phe Lys Arg Met Leu Asn Arg Glu Leu Thr His
```

-continued

```
                260                 265                 270
Leu Ser Glu Met Ser Arg Ser Gly Asn Gln Val Ser Glu Tyr Ile Ser
                275                 280                 285

Thr Thr Phe Leu Asp Lys Gln Asn Glu Val Glu Ile Pro Ser Pro Thr
            290                 295                 300

Met Lys Glu Arg Glu Lys Gln Gln Ala Pro Arg Pro Arg Pro Ser Gln
305                 310                 315                 320

Pro Pro Pro Pro Pro Val Pro His Leu Gln Pro Met Ser Gln Ile Thr
                    325                 330                 335

Gly Leu Lys Lys Leu Met His Ser Asn Ser Leu Asn Asn Ser Asn Ile
                340                 345                 350

Pro Arg Phe Gly Val Lys Thr Asp Gln Glu Glu Leu Leu Ala Gln Glu
            355                 360                 365

Leu Glu Asn Leu Asn Lys Trp Gly Leu Asn Ile Phe Cys Val Ser Asp
        370                 375                 380

Tyr Ala Gly Gly Arg Ser Leu Thr Cys Ile Met Tyr Met Ile Phe Gln
385                 390                 395                 400

Glu Arg Asp Leu Leu Lys Lys Phe Arg Ile Pro Val Asp Thr Met Val
                    405                 410                 415

Thr Tyr Met Leu Thr Leu Glu Asp His Tyr His Ala Asp Val Ala Tyr
                420                 425                 430

His Asn Ser Leu His Ala Ala Asp Val Leu Gln Ser Thr His Val Leu
            435                 440                 445

Leu Ala Thr Pro Ala Leu Asp Ala Val Phe Thr Asp Leu Glu Ile Leu
        450                 455                 460

Ala Ala Leu Phe Ala Ala Ala Ile His Asp Val Asp His Pro Gly Val
465                 470                 475                 480

Ser Asn Gln Phe Leu Ile Asn Thr Asn Ser Glu Leu Ala Leu Met Tyr
                    485                 490                 495

Asn Asp Glu Ser Val Leu Glu Asn His His Leu Ala Val Gly Phe Lys
                500                 505                 510

Leu Leu Gln Glu Asp Asn Cys Asp Ile Phe Gln Asn Leu Ser Lys Arg
            515                 520                 525

Gln Arg Gln Ser Leu Arg Lys Met Val Ile Asp Met Val Leu Ala Thr
        530                 535                 540

Asp Met Ser Lys His Met Thr Leu Leu Ala Asp Leu Lys Thr Met Val
545                 550                 555                 560

Glu Thr Lys Lys Val Thr Ser Ser Gly Val Leu Leu Leu Asp Asn Tyr
                    565                 570                 575

Ser Asp Arg Ile Gln Val Leu Arg Asn Met Val His Cys Ala Asp Leu
                580                 585                 590

Ser Asn Pro Thr Lys Pro Leu Glu Leu Tyr Arg Gln Trp Thr Asp Arg
            595                 600                 605

Ile Met Ala Glu Phe Phe Gln Gln Gly Asp Arg Glu Arg Glu Arg Gly
        610                 615                 620

Met Glu Ile Ser Pro Met Cys Asp Lys His Thr Ala Ser Val Glu Lys
625                 630                 635                 640

Ser Gln Val Gly Phe Ile Asp Tyr Ile Val His Pro Leu Trp Glu Thr
                    645                 650                 655

Trp Ala Asp Leu Val His Pro Asp Ala Gln Glu Ile Leu Asp Thr Leu
                660                 665                 670

Glu Asp Asn Arg Asp Trp Tyr Tyr Ser Ala Ile Arg Gln Ser Pro Ser
            675                 680                 685
```

```
Pro Pro Pro Glu Glu Glu Ser Arg Gly Pro Gly His Pro Pro Leu Pro
    690                 695                 700

Asp Lys Phe Gln Phe Glu Leu Thr Leu Glu Glu Glu Glu Glu Glu Glu
705                 710                 715                 720

Ile Ser Met Ala Gln Ile Pro Cys Thr Ala Gln Glu Ala Leu Thr Ala
                725                 730                 735

Gln Gly Leu Ser Gly Val Glu Glu Ala Leu Asp Ala Thr Ile Ala Trp
            740                 745                 750

Glu Ala Ser Pro Ala Gln Glu Ser Leu Glu Val Met Ala Gln Glu Ala
            755                 760                 765

Ser Leu Glu Ala Glu Leu Glu Ala Val Tyr Leu Thr Gln Gln Ala Gln
    770                 775                 780

Ser Thr Gly Ser Ala Pro Val Ala Pro Asp Glu Phe Ser Ser Arg Glu
785                 790                 795                 800

Glu Phe Val Val Ala Val Ser His Ser Ser Pro Ser Ala Leu Ala Leu
                805                 810                 815

Gln Ser Pro Leu Leu Pro Ala Trp Arg Thr Leu Ser Val Ser Glu His
            820                 825                 830

Ala Pro Gly Leu Pro Gly Leu Pro Ser Thr Ala Ala Glu Val Glu Ala
            835                 840                 845

Gln Arg Glu His Gln Ala Ala Lys Arg Ala Cys Ser Ala Cys Ala Gly
    850                 855                 860

Thr Phe Gly Glu Asp Thr Ser Ala Leu Pro Ala Pro Gly Gly Gly Gly
865                 870                 875                 880

Ser Gly Gly Asp Pro Thr
                885

<210> SEQ ID NO 3
<211> LENGTH: 1949
<212> TYPE: DNA
<213> ORGANISM: Aequoria victoria and Homo sapiens

<400> SEQUENCE: 3
atgcccttgg tggatttctt ctgcgagacc tgctctaagc cttggctggt gggctggtgg      60
gaccagttta aaaggatgtt gaaccgtgag ctcacacacc tgtcagaaat gagcaggtcc     120
ggaaaccagg tctcagagta catttccaca acattcctgg acaaacagaa tgaagtggag     180
atcccatcac ccacgatgaa ggaacgagaa aaacagcaag cgccgcgacc aagaccctcc     240
cagccgcccc cgcccctgt accacactta cagcccatgt cccaaatcac agggttgaaa      300
aagttgatgc atagtaacag cctgaacaac tctaacattc cccgatttgg ggtgaagacc     360
gatcaagaag agctcctggc caagaactg agaaacctga caagtgggg cctgaacatc       420 ttttgcgtgt cggattacgc tggaggccgc tcactcacct gcatcatgta catgatattc     480
caggagcggg acctgctgaa gaattccgc atcccggtgg acgcgatggt gacatacatg      540
ctgacgctgg aggatcacta ccacgctgac gtggcctacc ataacagcct gcacgcagct     600
gacgtgctgc agtccaccca gtactgctgg ccacgcctg cactagatgc agtgttcacg     660
gacctggaga ttctcgccgc cctcttcgcg gctgccatcc acgatgtgga tcaccctggg     720
gtctccaacc agttcctcat caacaccaat tcggagctgg cgctcatgta caacgatgag     780
tcggtgctcg agaatcacca cctggccgtg ggcttcaagc tgctgcagga ggacaactgc     840
gacatcttcc agaacctcag caagcgccag cggcagagcc tacgcaagat ggtcatcgac     900
atggtgctgg ccacggacat gtccaagcac atgaccctcc tggctgacct gaagaccatg     960
```

-continued

```
gtggagacca agaaagtgac cagctcaggg gtcctcctgc tagataacta ctccgaccgc    1020
atccaggtcc tccgaacat ggtgcactgt gccgacctca gcaaccccac caagccgctg     1080
gagctgtacc gccagtggac agaccgcatc atggccgagt tcttccagca gggtgaccga    1140
gagcgcgagc gtggcatgga aatcagcccc atgtgtgaca gcacactgc tccgtggag      1200 aagtctcagg tgggttttat tgactacatt gtgcacccat gtgggagac ctgggcggac    1260 cttgtccacc cagatgccca ggagatcttg gacactttgg aggacaaccg ggactggtac    1320
tacagcgcca tccggcagag cccatctccg ccacccgagg aggagtcaag ggggccaggc    1380
cacccacccc tgcctgacaa gttccagttt gagctgacgc tggaggagga agaggaggaa    1440
gaaatatcaa tggcccagat accgtgcaca gcccaagagg cattgactgc gcagggattg    1500
tcaggagtcg aggaagctct ggatgcaacc atagcctggg aggcatcccc ggcccaggag    1560
tcgttggaag ttatggcaca ggaagcatcc tggaggccg agctggaggc agtgtatttg     1620
acacagcagg cacagtccac aggcagtgca cctgtggctc cggatgagtt ctcgtcccgg    1680
gaggaattcg tggttgctgt aagccacagc agccctctg ccctggctct caaagcccc     1740 cttctccctg cttggaggac cctgtctgtt tcagagcatg ccccgggcct ccgggcctc     1800 ccctccacgg cggccgaggt ggaggcccaa cgagagcacc aggctgccaa gagggcttgc    1860
agtgcctgcg cagggacatt tggggaggac acatccgcac tcccagctcc tggtggcggg    1920
gggtcaggtg agacccctac ctgggatcc                                      1949
```

<210> SEQ ID NO 4
<211> LENGTH: 647
<212> TYPE: PRT
<213> ORGANISM: Aequoria victoria and Homo sapiens

<400> SEQUENCE: 4

```
Met Pro Leu Val Asp Phe Phe Cys Glu Thr Cys Ser Lys Pro Trp Leu
 1               5                  10                  15

Val Gly Trp Trp Asp Gln Phe Lys Arg Met Leu Asn Arg Glu Leu Thr
            20                  25                  30

His Leu Ser Glu Met Ser Arg Ser Gly Asn Gln Val Ser Glu Tyr Ile
        35                  40                  45

Ser Thr Thr Phe Leu Asp Lys Gln Asn Glu Val Glu Ile Pro Ser Pro
    50                  55                  60

Thr Met Lys Glu Arg Glu Lys Gln Gln Ala Pro Arg Pro Arg Pro Ser
65                  70                  75                  80

Gln Pro Pro Pro Pro Val Pro His Leu Gln Pro Met Ser Gln Ile
                85                  90                  95

Thr Gly Leu Lys Lys Leu Met His Ser Asn Ser Leu Asn Asn Ser Asn
            100                 105                 110

Ile Pro Arg Phe Gly Val Lys Thr Asp Gln Glu Glu Leu Leu Ala Gln
        115                 120                 125

Glu Leu Glu Asn Leu Asn Lys Trp Gly Leu Asn Ile Phe Cys Val Ser
    130                 135                 140

Asp Tyr Ala Gly Gly Arg Ser Leu Thr Cys Ile Met Tyr Met Ile Phe
145                 150                 155                 160

Gln Glu Arg Asp Leu Leu Lys Lys Phe Arg Ile Pro Val Asp Thr Met
                165                 170                 175

Val Thr Tyr Met Leu Thr Leu Glu Asp His Tyr His Ala Asp Val Ala
            180                 185                 190
```

```
Tyr His Asn Ser Leu His Ala Ala Asp Val Leu Gln Ser Thr His Val
        195                 200                 205

Leu Leu Ala Thr Pro Ala Leu Asp Ala Val Phe Thr Asp Leu Glu Ile
210                 215                 220

Leu Ala Ala Leu Phe Ala Ala Ile His Asp Val Asp His Pro Gly
225                 230                 235                 240

Val Ser Asn Gln Phe Leu Ile Asn Thr Asn Ser Glu Leu Ala Leu Met
                245                 250                 255

Tyr Asn Asp Glu Ser Val Leu Glu Asn His His Leu Ala Val Gly Phe
            260                 265                 270

Lys Leu Leu Gln Glu Asp Asn Cys Asp Ile Phe Gln Asn Leu Ser Lys
        275                 280                 285

Arg Gln Arg Gln Ser Leu Arg Lys Met Val Ile Asp Met Val Leu Ala
290                 295                 300

Thr Asp Met Ser Lys His Met Thr Leu Leu Ala Asp Leu Lys Thr Met
305                 310                 315                 320

Val Glu Thr Lys Lys Val Thr Ser Ser Gly Val Leu Leu Leu Asp Asn
                325                 330                 335

Tyr Ser Asp Arg Ile Gln Val Leu Arg Asn Met Val His Cys Ala Asp
            340                 345                 350

Leu Ser Asn Pro Thr Lys Pro Leu Glu Leu Tyr Arg Gln Trp Thr Asp
        355                 360                 365

Arg Ile Met Ala Glu Phe Phe Gln Gln Gly Asp Arg Glu Arg Glu Arg
370                 375                 380

Gly Met Glu Ile Ser Pro Met Cys Asp Lys His Thr Ala Ser Val Glu
385                 390                 395                 400

Lys Ser Gln Val Gly Phe Ile Asp Tyr Ile Val His Pro Leu Trp Glu
                405                 410                 415

Thr Trp Ala Asp Leu Val His Pro Asp Ala Gln Glu Ile Leu Asp Thr
            420                 425                 430

Leu Glu Asp Asn Arg Asp Trp Tyr Tyr Ser Ala Ile Arg Gln Ser Pro
        435                 440                 445

Ser Pro Pro Glu Glu Ser Arg Gly Pro Gly His Pro Pro Leu
450                 455                 460

Pro Asp Lys Phe Gln Phe Glu Leu Thr Leu Glu Glu Glu Glu Glu
465                 470                 475                 480

Glu Ile Ser Met Ala Gln Ile Pro Cys Thr Ala Gln Glu Ala Leu Thr
                485                 490                 495

Ala Gln Gly Leu Ser Gly Val Glu Glu Ala Leu Asp Ala Thr Ile Ala
            500                 505                 510

Trp Glu Ala Ser Pro Ala Gln Glu Ser Leu Glu Val Met Ala Gln Glu
        515                 520                 525

Ala Ser Leu Glu Ala Glu Leu Glu Ala Val Tyr Leu Thr Gln Gln Ala
530                 535                 540

Gln Ser Thr Gly Ser Ala Pro Val Ala Pro Asp Glu Phe Ser Ser Arg
545                 550                 555                 560

Glu Glu Phe Val Val Ala Val Ser His Ser Ser Pro Ser Ala Leu Ala
                565                 570                 575

Leu Gln Ser Pro Leu Leu Pro Ala Trp Arg Thr Leu Ser Val Ser Glu
            580                 585                 590

His Ala Pro Gly Leu Pro Gly Leu Pro Ser Thr Ala Ala Glu Val Glu
        595                 600                 605

Ala Gln Arg Glu His Gln Ala Ala Lys Arg Ala Cys Ser Ala Cys Ala
```

```
                610             615             620
Gly Thr Phe Gly Glu Asp Thr Ser Ala Leu Pro Ala Pro Gly Gly Gly
625                 630                 635                 640

Gly Ser Gly Gly Asp Pro Thr
            645

<210> SEQ ID NO 5
<211> LENGTH: 3999
<212> TYPE: DNA
<213> ORGANISM: Aequoria Victoria and Homo sapiens

<400> SEQUENCE: 5
atgcagcagg cgccgcagcc ttacgagttc ttcagcgagg agaacagtcc gaaatggcgg      60
ggactgttgg tctcggccct gcggaaggtt caggaacaag tgcatcccac tctctcagct     120
aatgaagagt ctctctatta tattgaagag ctgattttc cgctgcttaa taaattatgc      180
gtggcccagc caagcactgt tcaagatgta gaggagcgag ttcagaagac ctttcctcac     240
ccaattgata aatgggccat tgctgatgca caatctgcta tagaaaaacg aaaacgaaga     300
aatcctcttt tactgcctgt ggacaaaatc catccttcgt tgaaggaagt attagggtac     360
aaagtggact accatgtatc cctatatatt gtggctgtac tagagtatat ctcagctgat     420
attttaaaat tggctggtaa ttatgttttt aatatccggc attatgaaat atctcagcag     480
gacattaaag tgtcaatgtg tgcggataag gttttgatgg acatgtttga tcaggatgac     540
ataggtttgg tttctctctg tgaagatgaa cctggttctt ctggtgaatt aaactactat     600
gatcttgtca gaactgaaat cgcagaagaa agacagtatc tacgggaatt aaatatgatc     660
ataaaagtgt ttcagaaagc ctttctttct gatagaaagc tgtttaaacc ttctgatatc     720
gaaaagattt ttagtaacat ttcagatata catgaattga ctgtgaaact tttaggtttg     780
attgaagaca cagttgaaat gactgatgaa agcagtcctc atcccttagc tggcagctgt     840
tttgaagatt tggcagaaga gcaagcattt gatccttatg aaacattatc acaggacatt     900 cttcaccag agtttcatga acatttcaat aaattgatgg ccagacctgc agttgctcta     960
cactttcagt ccattgctga tggttttaaa gaggcagttc gttacgtcct tccacgtctt    1020
atgctggtgc cagtgtatca ctgttggcac tactttgagt tactaaagca attgaaagca    1080
tgtagtgaag aacaagaaga cagagaatgt ttgaaccaag ctattactgc tctcatgaat    1140
ctccaaggta gcatggaccg aatttacaag cagtattcac ctagacgtcg acctggagat    1200
cctgtttgcc ttttttatag tcaccaatta agaagcaaac acctggctat caaaaaaatg    1260
aatgaaattc agaaaaatat cgatggatgg gaaggcaaag atattggaca gtgttgtaat    1320
gaattcatta tggagggacc attgacaaga atcggtgcca acatgaacg gcatattttt    1380 ctgtttgatg gcttaatgat cagttgtaaa cctaatcatg ccagactcg gcttccaggt    1440 tacagtagtg cagaatacag gttaaaagaa aaatttgtca tgaggaaaat acaaatttgt    1500
gataaagaag atacttgtga gcacaagcat gcatttgaat tagtatccaa agatgagaac    1560
agcataatat ttgctgctaa gtctgctgaa gaaaaaaaca actggatggc agcccttatt    1620
tctcttcatt atcgtagtac tctagatcga atgttagatt cagtattatt gaagaagaa     1680 aatgagcaac cactgagatt accaagtcct gaagtatatc gttttgtagt aaaagactct    1740
gaggaaaaca ttgttttga agacaacttg caaagtagaa gtggcatccc cattattaaa    1800
ggaggaactg tagtgaaatt aattgaaagg ttaacatatc atatgtatgc agatcccaat    1860
tttgttcgta cttttcttac cacatatcgt tcatttgta aaccacagga attgctgagc     1920
```

-continued

```
ttactgattg aacggtttga aattccagag ccagaaccta ctgacgcaga caaattggca    1980
atagagaaag gcgagcagcc aatcagtgca gaccttaaaa gatttcgcaa ggaatatgtc    2040
caaccagtac aacttaggat cttaaatgta tttcggcatt gggttgaaca tcattttat     2100 gactttgaaa gagacttgga attgcttgaa agactagaat ccttcatttc aagtgtaaga    2160
gggaaagcta tgaaaaaatg ggtagagtca attgctaaga tcatcaggag gaagaagcaa    2220
gctcaggcaa atggagtaag ccataatatt accttttgaaa gtccacctcc accaattgaa   2280
tggcatatca gcaaaccagg acagtttgaa acatttgatc tcatgacact tgatccaata   2340
gaaattgcac gtcagctgac acttttggag tctgatcttt acaggaaagt tcaaccgtct   2400
gaacttgtag ggagtgtgtg gaccaaagaa gataaagaaa taaattctcc aaatttatta   2460
aaaatgattc gccataccac aaatctcacc ctctggtttg aaaaatgcat tgtggaagca   2520
gaaaattttg aagaacgggt ggcagtacta agtagaatta tagaaattct gcaagttttt   2580
caagatttga ataatttcaa tggcgtattg gagatagtca gtgcagtaaa ttcagtgtca   2640
gtatacagac tagaccatac ctttgaggca ctgcaggaaa ggaaaaggaa aattttggac   2700
gaagctgtgg aattaagtca agatcacttt aaaaaatacc tagtaaaact taagtcaatc   2760
aatccacctt gtgtgccttt ttttggaata tatttaacaa atattctgaa gaccgaagaa   2820
gggaataatg atttttttaaa aagaaaggg aaagatttaa tcaatttcag taagaggagg   2880
aaagtagctg aaattactgg agaaattcag cagtatcaga atcagcctta ctgtttacgg   2940
atagaaccag atatgaggag attctttgaa aaccttaacc ccatgggaag tgcatctgaa   3000
aaagagttta cagattattt gttcaacaag tcactagaaa ttgaacctcg aaactgcaaa   3060
cagccacctc gatttcctag gaaatcaact ttttccttaa aatctcctgg aataaagcct   3120
aacacaggcc gacatggctc tacctcaggt actttacgag gtcacccaac accattagaa   3180
agagaaccat gtaaaataag ctttagtcgg attgctgaaa ctgagctgga atcaacagtg   3240
tcagcaccaa cctctccaaa tacaccatct actccaccag tatctgcttc ttcagacctt   3300
agtgtatctt tagatgtgga tctcaacagc tcctgtggca gcaatagcat ctttgctcca   3360
gtgcttttgc cacattcaaa gtctttcttt agttcatgtg gtagtttaca taaactaagt   3420
gaagagcccc tgattcctcc tcctcttcct cctcgaaaaa agtttgatca tgatgcttca   3480
aattccaagg gaaatatgaa atctgatgat gatcctcctg ctattccacc gagacagcct   3540
cctcctccaa aggtaaaacc cagagttcct gttcctactg gtgcatttga tgggcctctg   3600
catagtccac ctccgccacc accaagagat cctcttcctg ataccctcc accagttccc    3660 cttcggcctc cagaacactt tataaactgt ccatttaatc ttcagccacc tccactgggg   3720
catcttcaca gagattcaga ctggctcaga gacattagta cgtgtccaaa ttcgccaagc   3780
actcctccta gcacaccctc tccaagggta ccgcgtcgat gctatgtgct cagttctagt   3840
cagaataatc ttgctcatcc tccagctccc cctgttccac caaggcagaa ttcaagccct   3900
catctgccaa aactgccacc aaagacttac aaacgggagc tttcgcaccc cccattgtac   3960
agactgcctt tgctagaaaa tgcagaaact ccccaatga                          3999
```

<210> SEQ ID NO 6
<211> LENGTH: 1333
<212> TYPE: PRT
<213> ORGANISM: Aequoria Victoria and Homo sapiens

<400> SEQUENCE: 6

-continued

```
Met Gln Gln Ala Pro Gln Pro Tyr Glu Phe Ser Glu Glu Asn Ser
 1               5                  10                 15

Pro Lys Trp Arg Gly Leu Leu Val Ser Ala Leu Arg Lys Val Gln Glu
                 20                  25                  30

Gln Val His Pro Thr Leu Ser Ala Asn Glu Glu Ser Leu Tyr Tyr Ile
             35                  40                  45

Glu Glu Leu Ile Phe Pro Leu Leu Asn Lys Leu Cys Val Ala Gln Pro
 50                  55                  60

Ser Thr Val Gln Asp Val Glu Arg Val Gln Lys Thr Phe Pro His
 65              70                  75                  80

Pro Ile Asp Lys Trp Ala Ile Ala Asp Ala Gln Ser Ala Ile Glu Lys
                 85                  90                  95

Arg Lys Arg Arg Asn Pro Leu Leu Pro Val Asp Lys Ile His Pro
                100                 105                 110

Ser Leu Lys Glu Val Leu Gly Tyr Lys Val Asp Tyr His Val Ser Leu
             115                 120                 125

Tyr Ile Val Ala Val Leu Glu Tyr Ile Ser Ala Asp Ile Leu Lys Leu
 130                 135                 140

Ala Gly Asn Tyr Val Phe Asn Ile Arg His Tyr Glu Ile Ser Gln Gln
145                 150                 155                 160

Asp Ile Lys Val Ser Met Cys Ala Asp Lys Val Leu Met Asp Met Phe
                165                 170                 175

Asp Gln Asp Asp Ile Gly Leu Val Ser Leu Cys Glu Asp Glu Pro Gly
            180                 185                 190

Ser Ser Gly Glu Leu Asn Tyr Tyr Asp Leu Val Arg Thr Glu Ile Ala
        195                 200                 205

Glu Glu Arg Gln Tyr Leu Arg Glu Leu Asn Met Ile Ile Lys Val Phe
210                 215                 220

Arg Glu Ala Phe Leu Ser Asp Arg Lys Leu Phe Lys Pro Ser Asp Ile
225                 230                 235                 240

Glu Lys Ile Phe Ser Asn Ile Ser Asp Ile His Glu Leu Thr Val Lys
                245                 250                 255

Leu Leu Gly Leu Ile Glu Asp Thr Val Glu Met Thr Asp Glu Ser Ser
            260                 265                 270

Pro His Pro Leu Ala Gly Ser Cys Phe Glu Asp Leu Ala Glu Glu Gln
        275                 280                 285

Ala Phe Asp Pro Tyr Glu Thr Leu Ser Gln Asp Ile Leu Ser Pro Glu
290                 295                 300

Phe His Glu His Phe Asn Lys Leu Met Ala Arg Pro Ala Val Ala Leu
305                 310                 315                 320

His Phe Gln Ser Ile Ala Asp Gly Phe Lys Glu Ala Val Arg Tyr Val
                325                 330                 335

Leu Pro Arg Leu Met Leu Val Pro Val Tyr His Cys Trp His Tyr Phe
            340                 345                 350

Glu Leu Leu Lys Gln Leu Lys Ala Cys Ser Glu Glu Gln Glu Asp Arg
        355                 360                 365

Glu Cys Leu Asn Gln Ala Ile Thr Ala Leu Met Asn Leu Gln Gly Ser
370                 375                 380

Met Asp Arg Ile Tyr Lys Gln Tyr Ser Pro Arg Arg Pro Gly Asp
385                 390                 395                 400

Pro Val Cys Pro Phe Tyr Ser His Gln Leu Arg Ser Lys His Leu Ala
                405                 410                 415

Ile Lys Lys Met Asn Glu Ile Gln Lys Asn Ile Asp Gly Trp Glu Gly
```

-continued

```
                420                 425                 430
Lys Asp Ile Gly Gln Cys Cys Asn Glu Phe Ile Met Glu Gly Pro Leu
            435                 440                 445
Thr Arg Ile Gly Ala Lys His Glu Arg His Ile Phe Leu Phe Asp Gly
450                 455                 460
Leu Met Ile Ser Cys Lys Pro Asn His Gly Gln Thr Arg Leu Pro Gly
465                 470                 475                 480
Tyr Ser Ser Ala Glu Tyr Arg Leu Lys Glu Lys Phe Val Met Arg Lys
                485                 490                 495
Ile Gln Ile Cys Asp Lys Glu Asp Thr Cys Glu His Lys His Ala Phe
            500                 505                 510
Glu Leu Val Ser Lys Asp Glu Asn Ser Ile Ile Phe Ala Ala Lys Ser
            515                 520                 525
Ala Glu Glu Lys Asn Asn Trp Met Ala Ala Leu Ile Ser Leu His Tyr
            530                 535                 540
Arg Ser Thr Leu Asp Arg Met Leu Asp Ser Val Leu Leu Lys Glu Glu
545                 550                 555                 560
Asn Glu Gln Pro Leu Arg Leu Pro Ser Pro Glu Val Tyr Arg Phe Val
                565                 570                 575
Val Lys Asp Ser Glu Glu Asn Ile Val Phe Glu Asp Asn Leu Gln Ser
            580                 585                 590
Arg Ser Gly Ile Pro Ile Ile Lys Gly Gly Thr Val Val Lys Leu Ile
595                 600                 605
Glu Arg Leu Thr Tyr His Met Tyr Ala Asp Pro Asn Phe Val Arg Thr
            610                 615                 620
Phe Leu Thr Thr Tyr Arg Ser Phe Cys Lys Pro Gln Glu Leu Leu Ser
625                 630                 635                 640
Leu Leu Ile Glu Arg Phe Glu Ile Pro Glu Pro Glu Pro Thr Asp Ala
                645                 650                 655
Asp Lys Leu Ala Ile Glu Lys Gly Glu Gln Pro Ile Ser Ala Asp Leu
            660                 665                 670
Lys Arg Phe Arg Lys Glu Tyr Val Gln Pro Val Gln Leu Arg Ile Leu
            675                 680                 685
Asn Val Phe Arg His Trp Val Glu His His Phe Tyr Asp Phe Glu Arg
            690                 695                 700
Asp Leu Glu Leu Leu Glu Arg Leu Glu Ser Phe Ile Ser Ser Val Arg
705                 710                 715                 720
Gly Lys Ala Met Lys Lys Trp Val Glu Ser Ile Ala Lys Ile Ile Arg
                725                 730                 735
Arg Lys Lys Gln Ala Gln Ala Asn Gly Val Ser His Asn Ile Thr Phe
            740                 745                 750
Glu Ser Pro Pro Pro Ile Glu Trp His Ile Ser Lys Pro Gly Gln
            755                 760                 765
Phe Glu Thr Phe Asp Leu Met Thr Leu Asp Pro Ile Glu Ile Ala Arg
            770                 775                 780
Gln Leu Thr Leu Leu Glu Ser Asp Leu Tyr Arg Lys Val Gln Pro Ser
785                 790                 795                 800
Glu Leu Val Gly Ser Val Trp Thr Lys Glu Asp Lys Glu Ile Asn Ser
                805                 810                 815
Pro Asn Leu Leu Lys Met Ile Arg His Thr Thr Asn Leu Thr Leu Trp
            820                 825                 830
Phe Glu Lys Cys Ile Val Glu Ala Glu Asn Phe Glu Glu Arg Val Ala
            835                 840                 845
```

```
Val Leu Ser Arg Ile Ile Glu Ile Leu Gln Val Phe Gln Asp Leu Asn
850                 855                 860

Asn Phe Asn Gly Val Leu Glu Ile Val Ser Ala Val Asn Ser Val Ser
865                 870                 875                 880

Val Tyr Arg Leu Asp His Thr Phe Glu Ala Leu Gln Glu Arg Lys Arg
                885                 890                 895

Lys Ile Leu Asp Glu Ala Val Glu Leu Ser Gln Asp His Phe Lys Lys
                900                 905                 910

Tyr Leu Val Lys Leu Lys Ser Ile Asn Pro Pro Cys Val Pro Phe Phe
                915                 920                 925

Gly Ile Tyr Leu Thr Asn Ile Leu Lys Thr Glu Glu Gly Asn Asn Asp
930                 935                 940

Phe Leu Lys Lys Lys Gly Lys Asp Leu Ile Asn Phe Ser Lys Arg Arg
945                 950                 955                 960

Lys Val Ala Glu Ile Thr Gly Glu Ile Gln Gln Tyr Gln Asn Gln Pro
                965                 970                 975

Tyr Cys Leu Arg Ile Glu Pro Asp Met Arg Arg Phe Glu Asn Leu
                980                 985                 990

Asn Pro Met Gly Ser Ala Ser Glu Lys Glu Phe Thr Asp Tyr Leu Phe
                995                 1000                1005

Asn Lys Ser Leu Glu Ile Glu Pro Arg Asn Cys Lys Gln Pro Pro Arg
                1010                1015                1020

Phe Pro Arg Lys Ser Thr Phe Ser Leu Lys Ser Pro Gly Ile Lys Pro
1025                1030                1035                1040

Asn Thr Gly Arg His Gly Ser Thr Ser Gly Thr Leu Arg Gly His Pro
                1045                1050                1055

Thr Pro Leu Glu Arg Glu Pro Cys Lys Ile Ser Phe Ser Arg Ile Ala
                1060                1065                1070

Glu Thr Glu Leu Glu Ser Thr Val Ser Ala Pro Thr Ser Pro Asn Thr
                1075                1080                1085

Pro Ser Thr Pro Pro Val Ser Ala Ser Ser Asp Leu Ser Val Ser Leu
                1090                1095                1100

Asp Val Asp Leu Asn Ser Ser Cys Gly Ser Asn Ser Ile Phe Ala Pro
1105                1110                1115                1120

Val Leu Leu Pro His Ser Lys Ser Phe Phe Ser Cys Gly Ser Leu
                1125                1130                1135

His Lys Leu Ser Glu Glu Pro Leu Ile Pro Pro Leu Pro Pro Arg
                1140                1145                1150

Lys Lys Phe Asp His Asp Ala Ser Asn Ser Lys Gly Asn Met Lys Ser
                1155                1160                1165

Asp Asp Asp Pro Pro Ala Ile Pro Pro Arg Gln Pro Pro Pro Pro Lys
                1170                1175                1180

Val Lys Pro Arg Val Pro Val Pro Thr Gly Ala Phe Asp Gly Pro Leu
1185                1190                1195                1200

His Ser Pro Pro Pro Pro Pro Arg Asp Pro Leu Pro Asp Thr Pro
                1205                1210                1215

Pro Pro Val Pro Leu Arg Pro Glu His Phe Ile Asn Cys Pro Phe
                1220                1225                1230

Asn Leu Gln Pro Pro Pro Leu Gly His Leu His Arg Asp Ser Asp Trp
                1235                1240                1245

Leu Arg Asp Ile Ser Thr Cys Pro Asn Ser Pro Ser Thr Pro Pro Ser
1250                1255                1260
```

```
Thr Pro Ser Pro Arg Val Pro Arg Cys Tyr Val Leu Ser Ser Ser
1265                1270                1275                1280

Gln Asn Asn Leu Ala His Pro Pro Ala Pro Pro Val Pro Pro Arg Gln
                1285                1290                1295

Asn Ser Ser Pro His Leu Pro Lys Leu Pro Pro Lys Thr Tyr Lys Arg
                1300                1305                1310

Glu Leu Ser His Pro Pro Leu Tyr Arg Leu Pro Leu Leu Glu Asn Ala
            1315                1320                1325

Glu Thr Pro Gln Glx
        1330

<210> SEQ ID NO 7
<211> LENGTH: 28
<212> TYPE: DNA
<213> ORGANISM: Artificial Sequence
<220> FEATURE:
<223> OTHER INFORMATION: 4A-Ct-top PCR primer used to amplify the
      C-terminal part HSPDE4A4

<400> SEQUENCE: 7
gtttaaaagg atgttgaacc gtgagctc                                      28

<210> SEQ ID NO 8
<211> LENGTH: 28
<212> TYPE: DNA
<213> ORGANISM: Artificial Sequence
<220> FEATURE:
<223> OTHER INFORMATION: 4A-bottom PCR primer used to amplify the
      C-terminal part HSPDE4A4 and also to amplify the coding region
      of HSPDE4A1

<400> SEQUENCE: 8
gtggatccca ggtagggtct ccacctga                                      28

<210> SEQ ID NO 9
<211> LENGTH: 28
<212> TYPE: DNA
<213> ORGANISM: Artificial Sequence
<220> FEATURE:
<223> OTHER INFORMATION: 4A4-top PCR primer used to amplify the
      N-terminal part of HSPDE4A4

<400> SEQUENCE: 9
gtaagcttgc gccatggaac ccccgacc                                      28

<210> SEQ ID NO 10
<211> LENGTH: 33
<212> TYPE: DNA
<213> ORGANISM: Artificial Sequence
<220> FEATURE:
<223> OTHER INFORMATION: 4A4N-bottom PCR primer used to amplify the
      N-terminal part of HSPDE4A4

<400> SEQUENCE: 10
ggttttaaac ttgtgcgagg ccatctcgct gac                                33

<210> SEQ ID NO 11
<211> LENGTH: 37
<212> TYPE: DNA
<213> ORGANISM: Artificial Sequence
<220> FEATURE:
<223> OTHER INFORMATION: 9658-top PCR primer contains the Avr2 cloning
      sites and flanks the zeocin resistance gene including its E. coli
      promoter

<400> SEQUENCE: 11
```
tcctaggctg cagcacgtgt tgacaattaa tcatcgg        37

<210> SEQ ID NO 12
<211> LENGTH: 37
<212> TYPE: DNA
<213> ORGANISM: Artificial Sequence
<220> FEATURE:
<223> OTHER INFORMATION: 9655-bottom PCR primer-contains Avr2 cloning
      sites and flanks the zeocin resistance gene including its E. coli
      promoter

<400> SEQUENCE: 12
tcctaggtca gtcctgctcc tcggccacga agtgcac        37

<210> SEQ ID NO 13
<211> LENGTH: 34
<212> TYPE: DNA
<213> ORGANISM: Artificial Sequence
<220> FEATURE:
<223> OTHER INFORMATION: 0099-top PCR primer used to isolate the coding
      sequence of human SOS1 from a human fetus or brain cDNA library

<400> SEQUENCE: 13
gttggatccc atgcagcagg cgccgcagcc ttac        34

<210> SEQ ID NO 14
<211> LENGTH: 35
<212> TYPE: DNA
<213> ORGANISM: Artificial Sequence
<220> FEATURE:
<223> OTHER INFORMATION: 0100-bottom PCR primer used to isolate the
      coding sequence of human SOS1 from a human fetus or brain cDNA
      library

<400> SEQUENCE: 14
gttgcggccg ctcattgggg agtttctgca ttttc        35

<210> SEQ ID NO 15
<211> LENGTH: 27
<212> TYPE: DNA
<213> ORGANISM: Artificial Sequence
<220> FEATURE:
<223> OTHER INFORMATION: 0073-top PCR primer used to isolate the coding
      sequence of human GRB2 from a human fetus or brain or placenta
      cDNA library

<400> SEQUENCE: 15
gcgaagcttt cagaatggaa gccatcg        27

<210> SEQ ID NO 16
<211> LENGTH: 26
<212> TYPE: DNA
<213> ORGANISM: Artificial Sequence
<220> FEATURE:
<223> OTHER INFORMATION: 0074-bottom PCR primer used to isolate the
      coding sequence of human GRB2 from a human fetus or brain or
      placenta cDNA library

<400> SEQUENCE: 16
gccgaattcg gacgttccgg ttcacg        26

<210> SEQ ID NO 17
<211> LENGTH: 28
<212> TYPE: DNA
<213> ORGANISM: Artificial Sequence
<220> FEATURE:
<223> OTHER INFORMATION: 9949 oligonucleotide used to ligate the -continued vector fragment to create resulting plasmid PS587

<400> SEQUENCE: 17
ctagcattaa tacgactcac tataggga                                           28

<210> SEQ ID NO 18
<211> LENGTH: 28
<212> TYPE: DNA
<213> ORGANISM: Artificial Sequence
<220> FEATURE:
<223> OTHER INFORMATION: 9950 oligonucleotide used to ligate the
      vector fragment to create resulting plasmid PS587

<400> SEQUENCE: 18
gatctcccta tagtgagtcg tattaatg                                           28

<210> SEQ ID NO 19
<211> LENGTH: 26
<212> TYPE: DNA
<213> ORGANISM: Artificial Sequence
<220> FEATURE:
<223> OTHER INFORMATION: 9952-top PCR primer used to isolate the coding
      sequence of human PKAcat (except the 17 N-terminal amino acids)
      from human liver or spleen cDNA library

<400> SEQUENCE: 19
gagcgtgaaa gaattcttag ccaaag                                             26

<210> SEQ ID NO 20
<211> LENGTH: 29
<212> TYPE: DNA
<213> ORGANISM: Artificial Sequence
<220> FEATURE:
<223> OTHER INFORMATION: 9922-bottom PCR primer used to isolate the
      coding sequence of human PKAcat (except the 17 N-terminal
      amino acids) from human liver or spleen cDNA library

<400> SEQUENCE: 20
gtggatccca aaactcagaa aactccttg                                          29

<210> SEQ ID NO 21
<211> LENGTH: 62
<212> TYPE: DNA
<213> ORGANISM: Artificial Sequence
<220> FEATURE:
<223> OTHER INFORMATION: 9955 oligonucleotide which adds remaining
      N-terminal amino acids to PKAcat

<400> SEQUENCE: 21
agcttccgcg atgggcaacg ccgccgccgc caagaagggc agcgagcagg agagcgtgaa        60
ag                                                                       62

<210> SEQ ID NO 22
<211> LENGTH: 62
<212> TYPE: DNA
<213> ORGANISM: Artificial Sequence
<220> FEATURE:
<223> OTHER INFORMATION: 9956 oligonucleotide which adds remaining
      N-terminal amino acids to PKAcat

<400> SEQUENCE: 22
aattctttca cgctctcctg ctcgctgccc ttcttggcgg cggcggcgtt gcccatcgcg        60
ga                                                                       62

<210> SEQ ID NO 23

```
<211> LENGTH: 32
<212> TYPE: DNA
<213> ORGANISM: Artificial Sequence
<220> FEATURE:
<223> OTHER INFORMATION: 0143-top PCR primer used to isolate the coding
      sequence of human GRB2 from the PS587 plasmid

<400> SEQUENCE: 23
gttggatccc atggaagcca tcgccaaata tg                                  32

<210> SEQ ID NO 24
<211> LENGTH: 29
<212> TYPE: DNA
<213> ORGANISM: Artificial Sequence
<220> FEATURE:
<223> OTHER INFORMATION: 0142-bottom PCR primer used to isolate the
      coding sequence of human GRB2 from the PS587 plasmid

<400> SEQUENCE: 24
gtttctagat tagacgttcc ggttcacgg                                      29

<210> SEQ ID NO 25
<211> LENGTH: 33
<212> TYPE: DNA
<213> ORGANISM: Artificial Sequence
<220> FEATURE:
<223> OTHER INFORMATION: 0122 PCR primer used to isolate the
      C-terminal part of the coding sequence of human SOS1 from
      human fetus or brain cDNA library

<400> SEQUENCE: 25
gttctcgagt catgagcttt agtcggattg ctg                                 33

<210> SEQ ID NO 26
<211> LENGTH: 33
<212> TYPE: DNA
<213> ORGANISM: Artificial Sequence
<220> FEATURE:
<223> OTHER INFORMATION: 0123 PCR primer used to isolate the
      C-terminal part of the coding sequence of human SOS1 from
      human fetus or brain cDNA library

<400> SEQUENCE: 26
gttggatcct cattggggag tttctgcatt ttc                                 33

<210> SEQ ID NO 27
<211> LENGTH: 22
<212> TYPE: DNA
<213> ORGANISM: Artificial Sequence
<220> FEATURE:
<223> OTHER INFORMATION: 9916 PCR primer used to isolate the Cys1
      domain of human PKCgamma from human brain cDNA library

<400> SEQUENCE: 27
gtgaattcgg ccatggctgg tc                                             22

<210> SEQ ID NO 28
<211> LENGTH: 28
<212> TYPE: DNA
<213> ORGANISM: Artificial Sequence
<220> FEATURE:
<223> OTHER INFORMATION: 9935 PCR primer used to isolate the Cys1 domain
      of human PKCgamma from human brain cDNA library

<400> SEQUENCE: 28
gtggtacctt cccagcgcct ggacactc                                       28
```

```
<210> SEQ ID NO 29
<211> LENGTH: 32
<212> TYPE: DNA
<213> ORGANISM: Artificial Sequence
<220> FEATURE:
<223> OTHER INFORMATION: 4A1-top PCR primer used to amplify the
      coding region of HSPDE4A1

<400> SEQUENCE: 29
gtaagcttaa gatgcccttg gtggatttct tc                                 32
```

METHOD FOR EXTRACTING QUANTITATIVE INFORMATION RELATING TO INTERACTIONS BETWEEN CELLULAR COMPONENTS

This application is the national phase under 35 U.S.C. § 371 of PCT International Application No. PCT/DK01/00466 which has an International filing date of Jul. 3, 2001, which designated the United States of America.

FIELD

The present invention relates to measurement of interactions between two components wherein the two components are present in a cell, and where both components are most usually wholly or mainly proteinaceous in composition (i.e. the interaction is a protein-protein interaction, or protein-protein binding event). This is presently referred to as "GFP assisted Readout of Interacting Proteins (GRIP)"

The present invention also relates to an extraction buffer used in high throughput screening for drugs that affect the intracellular distribution of intracellular components. The extraction buffer comprises a cellular fixation agent and a cellular permeabilization agent.

BACKGROUND

The interaction of proteins with each other and with other cellular components is an intrinsic part of nearly every cellular process, and this is especially true of intracellular signalling systems. Information is passed through and between signalling systems by a series of such interactions. In order to study the function of a protein, a practical strategy is first to identify the components that it interacts with. Most of these will be other proteins—sometimes of the same species, but most often a very different type and with very different functional characteristics.

The identification of novel interactions is a very rapidly growing area of research in cell biology and signal transduction. A notable feature of recent discoveries in this area is the specificity with which partners interact, equalling or exceeding the degree of specificity commonly seen in ligand-receptor interactions seen at the cell surface. Identification of interacting species brings with it the opportunity to identify novel signalling interactions that may assist greatly in the functional characterisabon of proteins involved in cellular signalling. In addition the method will be applicable to the development of new pharmaceutical agents capable of disrupting or engaging partners in an interaction.

Compounds with this mechanism of action will be able to modulate the flow of information through signalling pathways, and in so doing find application in very many areas of human and animal health care. Since such compounds will be inherently very selective and have their action without the need for gross inhibition of catalytic activity, it can be expected that therapies based on their use will not carry with them the problems of poor specificity and damaging side effects commonly associated with more traditional active-site inhibitors.

Existing methods for identification of interacting species can be divided into two groups: First are those methods that can only work with more or less purified components brought together in vitro, such as surface plasmon resonance (evanescent wave methods), protein mass spectroscopy, fluorescence correlation spectroscopy and anisotropy measurements all with the common feature that the components of interest are isolated from the cellular context. The second group includes all methods designed to work within living cells. Of these, many have been developed to work in yeast cells (yeast two hybrid, reverse yeast two hybrid and variations thereof) but some have been adapted for use in mammalian cell systems. Cellular methods for detection of protein interactions have been well reviewed by Mendelsohn, A. R., Brent, R. (1999) (Science 284(5422):1948). Many of these methods are descendants of the conventional two-hybrid methods, where transcriptional activity is initiated by the bringing together of bi-partite transcription factors through the interaction of attached "bait" and "prey" components, while other methods rely on reconstitution of a biochemical function in vivo. Rossi et al. (2000) (Trends in Cell Biology 10:119-122) have thus developed a mammalian cell-based protein-protein interaction assay where the read-out is not transcriptional but reconstitution of a mutated beta-galactosidase enzyme. Upon reconstitution of the tetrameric enzyme, enzymatic activity can be monitored. In addition methods for monitoring protein-protein interactions that are based on an optical read-out i.e. fluorescence resonance transfer (FRET), or coincidence analysis (a variant of fluorescence correlation spectroscopy), or fluorescence lifetime changes. The last three categories are more normally applied under simplified in vitro conditions, but attempts are being made to move them into the more complex environment of the living cell.

Recently Tobias Meyer reported (WO00/17221) a method wherein two heterologous conjugates are introduced into a cell. The first heterologous conjugate comprises the first protein of interest conjugated to a detectable group (e.g. GFP). The second heterologous conjugate comprises a second protein of interest conjugated to a protein that specifically binds to an internal structure within the cell upon stimulation with phorbol ester. When the second protein is bound to an internal structure within the cell, with a known distribution, binding between the two proteins of interest can be visualised as the detectable group will be located bound to internal structure within the cell.

Proteins(-GFP) that are not "anchored" in an intracellular organelle or compartment, but are more or less mobile in the cytosol, will diffuse into the surrounding medium upon cell permeabilization, at a rate largely governed by the degree of permeabilisation imposed. It is difficult to control the release of cellular contents by permeabilization since detergents have the tendency to not only disrupt the membrane but also over time disrupt intracellular components. Beside this, damaging the membrane will start some uncontrolled protease activity with the same unintentional result. This phenomenon is also seen when using non detergent permeabilization (eg. Digitonin). Fixative agents are commonly used to preserve structural integrity in cells during the processes necessary to prepare biological material for microscopy. Fixatives aimed at preserving or stabilising protein structures within cells can be divided into two groups; those that coagulate proteins, such as organic acids or alcohols (e.g. acetic acid, ethanol), and those that cross-link proteins together into an insoluble network, such as the aldehydes (e.g. formaldehyde or glutaraldehyde). The rate of fixation by such agents is governed by their rate of penetrance into cells together with the rate of chemical cross-linking or coagulation that they can achieve. The processes and methods of cellular fixation have been thoroughly studied and described in the scientific literature (see, for example, Fixation for Electron Microscopy by M. A. Hayat, 1981, Academic Press, New York).

Translocation usually involves changes in the effective mobility of at least one protein within the cell, either through changes in interaction between that component and an anchored (or effectively non-mobile) component or through a change in location or compartmentation of the component, for example a transfer from the extra-nuclear cytoplasm into the nucleus itself. Changes in interaction or compartmentation constitute translocation. Redistribution™ is the art of making translocation a measurable event (WO98/45704). Translocation may involve change in mobility or compartmentation of a component to which the component of interest is attached, for example a motor protein by which the component of interest is carried. Some translocations involve sub-microscopic distances, for instance the interaction between a soluble signaling protein in the cytoplasm and an adjacent actin filament or intracellular membrane. The mobility of the previously soluble component is greatly changed in such a translocation, but any change in its position in space may be unresolvable by microscopic means. In this case, it would be desirable to separate mobile from immobile forms of the protein of interest in order to reveal the redistribution signal.

Usually redistribution™ is measured by "imaging", which is very time consuming and inconvenient for drug screening in HT format. Redistribution™ assays often comprise cell lines stably expressing a particular protein of interest, (most often that protein being an engineered protein fusion between the protein of interest and a luminescent protein such as GFP). In such cells, it may be the case that the component of interest is overexpressed to some degree relative to the other components in the cell with which it should interact. This can lead to a masking of the translocation event by excess amounts of the protein of interest that cannot physically interact with the limited number of partner components available in the cell. In such cases, removal of the excess component of interest may be sufficient to unmask the translocation that has occurred.

Fixation of the cells before permeabilization is never successful in such cases, since all proteins become effectively immobilized to approximately the same degree under the influence of the fixative, and hence cannot be differentially removed or washed away from the cell.

SUMMARY OF THE INVENTION

The interaction between Sos and Grb2 can be measured in various ways. As shown in the Example 7, cells co-transfected with a PDE4A4-SosA conjugate and with a Grb2-EGFP conjugate illustrate the binding between SosA and Grb2. In Example 8 the conjugates are PKAcat-hGrb2 and EGFP-Sos-Cterm. The advantage of the PKAcat conjugates is that no special treatment is necessary in order to visualise interaction, as long as levels of cAMP within cells remain sufficiently low so that PKA is predominately attached to it regulatory subunits. In Example 9 the conjugates are Cys1-Grb2 and EGFP-Sos-Cterm. The possible advantage of the Cys1 conjugates are that they will take one component of a pair to the plasma membrane when treated with PMA or some other activation stimulus. This special location may be necessary in order to activate interaction of the components being studied.

Example 3 describes a generic way to produce cell lines by co-transfection of two plasmids, each expression a heterologous conjugate. As illustrated in this example, by using PDE4A4 based anchor probes as anchor-proteins an average of two dense aggregates is formed by treatment with rolipram. These aggregates can by detected directly with an antibody directed against the unique C-terminal peptide sequence of PDE4A. The dense aggregates (the spots) will disappear when either rolipram is removed or competed against with one of a particular class of PDE4 inhibitors (e.g. RP73401). It is important to note that the treatment with rolipram does not affect the levels of cAMP in the cells (Example 14).

Example 4 describes that using PKAcata based anchor probes as anchor-proteins aggregates are formed in the cytoplasm when the concentration of cytoplasmic cAMP is low. These aggregates can by detected directly with an antibody directed against PKAc or against the PKA regulatory subunit. These aggregates disperse into the cytoplasm when cAMP concentrations are elevated.

Example 5 describes that using PDE4A1 based anchor probes as anchor-proteins, small perinuclear spots are formed in the cytoplasm in otherwise untreated cells. PDE4A1 spots can by detected directly with an antibody directed against the unique C-terminal peptde sequence of PDE4A. These spots disperse into the cytoplasm when rolipram is added to the cells.

Example 6 describes that using Cys1 domain based anchor probes as anchor-proteins redistributes to the plasma membrane when activated e.g. by treatment with PMA. The localisation of the Cys1 domain can be confirmed with antibodies directed against the myc or flag antigens (when myc or flag sequences are included in the genetic construct used to transfect the cells).

Application of fixative and permeabilisation simultaneously, as described in this document, aims to preserve local concentrations of the anchored, diffusionally restricted or largely immobile form of the protein of interest while allowing freely mobile or unanchored forms to be released from the cell. It is expected that the process of cell permeabilisation, especially by detergents, will in time remove even relatively immobile, anchored or compartmentalised proteins from the cell, and hence a balance must be found between the rate of permeabilisation and solubilisation caused by the detergent agent, and the rate at which cross-linking or fixation takes place. This balance may be achieved by careful selection of the fixative and premeabilisation agents, controlling the relative concentrations of these agents, also by controlling the physical and chemical conditions under which the agents work (pH, osmolarity or ionic strength, temperature).

In order to control the permeabilization to a level that allows "floating" proteins to leave the cells without disrupting intracellular organelles and compartments, cells are slightly chemically fixed during the permeabilization process. The purpose is to just let the "non bound" proteins leave the cells and then have the rest chemically fixed. The present application discloses how complex intracellular movements within the cell can be measured easily. In Example 10, the change in mobility of BAD caused by the binding between the 14-3-3 protein and BAD is measured using a PDE4A4-14-3-3 and an EGFP-BAD fusion. The PDE4A4-14-3-3 protein is stuck in spots within the cell due to previous treatment with rolipram. By extracting the soluble (or mobile) BAD, fused to GFP, with a buffer comprising a combination of a cellular permeabilization agent and a cellular fixation agent, only the immobile GFP is left in the cell, and the change in mobility of BAD caused by binding to the 14-3-3 protein, can be read as a change in fluorescence intensity. Example 11 shows the same principle applied to the Redistribution™ of NFkB(p65) from cytosol to nucleus upon stimulation of NFkB. The optimization of the extraction buffer, to identify the optimal ratio between the cellular fixation agent and the cellular permeabilisation agent is illustrated in Example 12.

DETAILED DISCLOSURE

The redistribution-trap method, subject of this application, is different from any of the above-mentioned methods in that it utilises positional information from PDE4 and in one aspect distribution of a GFP-labelled fluorescent probe in a cell, to indicate the presence or absence of an interaction between specific components. That it does so in the complex environment of the cell, which allows for the influence of factors which may modulate an interaction in the same way as would happen in the native system, adds important physiological relevance to the method. Since it is based on non-destructive fluorescence imaging, meaning that the cells can be live and active whilst being monitored, and since it is based on non-disturbing treatment with e.g. rolipram, the redistribution-trap method also allows transient or conditional interactions to be monitored. Transient or conditional interactions may occur when components are phosphorylated or otherwise modified during their cycle of operation (e.g. transmission of a signal), and such modifications are common amongst components of intracellular signalling pathways. As the method does not rely on covalent interactions nor that the components need have a specific orientation upon interaction, the method is very sensitive and allow for measurement of even low affinity interactions.

One aspect thus relates to a method for detecting if a compound modulates an intracellular protein interaction comprising the steps of:
(a) providing a cell that contains two heterologous conjugates,
the first heterologous conjugate comprising a first protein of interest conjugated to a detectable group,
the second heterologous conjugate comprising a second protein of interest conjugated to an anchor protein that can specifically bind to an internal structure within the cell;
(b) detecting the intracellular distribution of the detectable group an intracellular distribution of said detectable group mimicking the intracellular distribution of the anchor-protein being indicative of binding between the two proteins of interest;
(c) repeating step (b) with and without the compound;

a change in intracellular distribution of the detectable group with and without the compound being indicative of the compound modulating said protein interaction.

The redistribution-trap method according to the present invention makes use of the fact that many signalling components redistribute within the cell to specific locations upon specific stimuli or treatments. If those components can be labelled in some way to make them visible in the cell, their location can be monitored and measured by a number of image-based techniques. Since imaging techniques are non-destructive, they allow measurements to be made on living cells, hence active processes can be followed over time if that is required—as may be the case when transient events need to be monitored. This application details how the knowledge that a particular component will redistribute upon receiving a certain stimulus (the "anchor" stimulus) can be harnessed, to create a system to explore interactions between intracellular components. If a component is known to distribute to a known cellular location upon a certain stimulus, another component (the "bait") may be covalently attached to the first (the "anchor") and, given the appropriate anchor stimulus, will be expected to assume the same distribution in the cell as the anchor component to which it is attached. A further component (the "prey"), which is expected to interact with the bait component, is introduced into the same cell. The prey component is labelled in some way to make it visible in the cell. If an interaction occurs between bait and prey (perhaps requiring a further interaction "stimulus"), then the prey component also takes up the same distribution within the cell as the anchor-bait component, but only if the appropriate anchor stimulus has also been applied. Using this system it is therefore possible to distinguish between specific bait-prey interactions and any other condition affecting the distribution of the detectable prey component. The redistributon-trap method is therefore able to impose a gross redistribution upon interacting components within the cell, even if the components in isolation would not normally display an appreciable redistribution as part of their functional cycle. Anchor systems can be designed to achieve redistribution to compartments or locations within cells where the interacting components may experience the influences that would normally be required to modulate the interaction between those components. As an example, some components may normally require to be phosphorylated or dephosphorylated by enzymes sequestered in the plane of the plasma membrane—for such components it would be appropriate for an anchor system to be chosen such that the anchor stimulus redistributed the anchor probe to the plasma membrane, to allow the interacting components to be appropriately modified. An example of such an anchor system would be one based on the Cys1 domain of PKCγ.

The method also allows for targeting interactions to different locations within the cell with the purpose of studying whether location specific conditions are necessary for the interaction to occur. In one embodiment one or both interacting components are targeted to the nuclear compartment. In another embodiment, one or both interacting components are targeted to mitochondria outer or inner membranes. In another embodiment, one or both interacting components are targeted to different regions of Golgi bodies. In another embodiment, one or both interacting components are targeted to focal adhesion complexes. In another embodiment, one or both interacting components are targeted to cytoskeletal structures such as F-actin strands or microtubular bundles. In another preferred embodiment, one or both interacting components are targeted to the plasma membrane. In another preferred embodiment, one or both interacting components are targeted to cytoplasmic granules or aggregates such as those formed by PDE4A4 in the presence of rolipram.

Thus, a specific embodiment of the present invention relates to a method wherein the specific binding to the internal structure within the cell is induced by an anchor stimulus that by itself has little likelihood of stimulating or inhibiting signalling activity within the cell of interest.

Due to the strong anchoring response of PDE4A4 to rolipram and other specific PDE4 inhibitors such as RS25344, PDE4A4 is most preferred as the anchoring species. Furthermore, it seems that the attachment of PDE4A4 to it's anchor site is not affected by he presence of additional parts attached to the C-terminal of the PDE4A4 molecule, here these attachments can be of very variable size (from less than 10 kDa to at least 150 kDa). Thus, a specific embodiment of the present invention relates to a method as described above wherein the specific binding is induced by addition of the anchor stimulus rolipram and wherein the anchor protein is PDE4A4.

The particular utility of stimulus-induced distributions, such as those that are based on PDE4A4 anchors or PKCαCys1 domains, is that in one and the same cell it is possible to switch on a distinctive distribution where previously there was none. This not only guarantees, in advance, that the distinctive distribution is purely a result of specific interaction between anchored and detectable components (the anchor component responding to the stimulus is "invisible" unless decorated by the detectable component), but also guarantees that this interaction will give a signal that is measurable by the assay equipment configured to detect the specific and expected distribution of the anchor component. In effect this latter point means that many different interactions can be measured and assayed without the need to reconfigure the measuring equipment or the assay method. Also, the inducing stimulus provides a reference compound in screening assays by which the maximum and minimum expected signals for an assay can be determined.

Many signalling components have a specific location within the cell and redistribute upon specific stimuli or treatments. If those components can be labelled in some way to make them visible in the cell, their location can be monitored and measured by a number of image-based techniques. Since imaging techniques are non-destructive, they allow measurements to be made on living cells, hence active processes can be followed over time if that is required—as may be the case when transient events need to be monitored. This application details how the knowledge that a particular component will redistribute upon receiving a certain stimulus (the "anchor" stimulus) can be harnessed, to create a system to explore interactions between intracellular components. If a component is known to have an inherently distinctive cellular distribution, another component (the "bait") may be covalently attached to the first (the "anchor") and, without any anchor stimulus, will be expected to assume the same distribution in the cell as the anchor component to which it is attached. A further component (the "prey"), which is expected to interact with the bait component, is introduced into the same cell. The prey component is labelled in some way to make it visible in the cell. If an interaction occurs between bait and prey (perhaps requiring a further "interaction stimulus"), then the prey component also takes up the same distribution within the cell as the anchor-bait component, even without application of an anchor stimulus due to the specific location in the first place. Further, if the inherent distinctive distribution of the anchor component will be dissolved by application of an anchor stimulus, then such a system is useful to distinguish between specific bait-prey interactions and any other condition affecting the distribution of the detectable prey component. The redistribution-trap method is therefore able to impose a gross redistribution upon interacting components within the cell, even if the components in isolation would not normally display an appreciable redistribution as part of their functional cycle. Anchor systems can be designed to achieve redistribution to compartments or locations within cells where the interacting components may experience the influences that would normally be required to modulate the interaction between those components. As an example, the spot like cytoplasmic distribution of PKA can be dissolved by addition of forskolin; the spot like cytoplasmic distribution of PDE4A1 can be dissolved by addition of rolipram; the spot like nuclear distribution of histonedeacetylase 5 (HDAC5) is dissolved by Trichostatin A (TSA); or the specific binding of the anchor protein is PLC-delta to the cell membrane is dissolved by addition of ATP and distributed within the cytoplasm.

For these systems where a distinctive distribution is dispersed or dissolved by a specific stimulus (the anchor stimulus), such as those based on PDE4A1, PKAcat, PLCdelta or HDAC5, the stimulus provides a means to check whether that distinct distribution is the result of interaction between anchored and detectable components, or results from some inherent tendency of the detectable component to assume that distinct distribution within the cell. The check for this can be made in one and the same cell that the assay for interaction is measured. As with stmulus-induced distributions, systems with an initial distinct distribution of the anchor component share the advantages of being able to assay many different interactions with one configuration of equipment and assay protocol. The anchor stimulus in each case again provides a reference compound in screening assays by which the maximum and minimum expected signals for an assay can be determined. The particular additional advantage of those systems where the anchor stimulus disperses a distribution is that no pretreatment or co-treatment of cells with distribution stimuli is necessary during the assay procedure, precluding any possibility that the anchor stimulus may interfere, directly or indirectly, with the interaction that is being tested.

The term "compound" is intended to indicate any sample, which has a biological function or exerts a biological effect in a cellular system. The sample may be a sample of a biological material such as a sample of a body fluid including blood, plasma, saliva, milk, urine, or a microbial or plant extract, an environmental sample containing pollutants including heavy metals or toxins, or it may be a sample containing a compound or mixture of compounds prepared by organic synthesis or genetic techniques. The compound may be small organic compounds or biopolymers, including proteins and peptides.

The compound to be tested can be regarded as a special interaction stimulus.

Numerous cell systems for transfection exist. A few examples are *Xenopus* oocytes or insect cells, such as the sf9 cell line, or mammalian cells isolated directly from tissues or organs taken from healthy or diseased animals (primary cells), or transformed mammalian cells capable of indefinite replication under cell culture conditions (cell lines). However, it is preferred that the cells used are mammalian cells. This is due to the complex biochemical interactions specific for each cell type. The term "mammalian cell" is intended to indicate any living cell of mammalian origin. The cell may be an established cell line, many of which are available from The American Type Culture Collection (ATCC, Virginia, U.S.A.) or similar Cell Culture Collections. The cell may be a primary cell with a limited life span derived from a mammalian tissue, including tissues derived from a transgenic animal, or a newly established immortal cell line derived from a mammalian tissue including transgenic tissues, or a hybrid cell or cell line derived by fusing different cell types of mammalian origin e.g. hybridoma cell lines. The cells may optionally express one or more non-native gene products, e.g. receptors, enzymes, enzyme substrates, prior to or in addition to the fluorescent probe. Preferred cell lines include but are not limited to those of fibroblast origin, e.g. BHK, CHO, BALB, NIH-3T3 or of endothelial origin, e.g. HUVEC, BAE (bovine artery endothelial), CPAE (cow pulmonary artery endothelial), HLMVEC (human lung microvascular endothelial cells), or of airway epithelial origin, e.g. BEAS-2B, or of pancreatic origin, e.g. RIN, INS-1, MIN6, bTC3, aTC6, bTC6, HIT, or of hematopoietic origin, e.g. primary isolated human monocytes, macrophages, neutrophils, basophils, eosinophils and lymphocyte populations, AML-14, AML-193, HL-60, RBL-1, U937, RAW, JAWS, or of adipocyte origin, e.g. 3T3-L1, human pre-adipocytes, or of neuroendocrine origin, e.g. AtT20, PC12, GH3, muscle origin, e.g. SKMC, A10, C2C12, renal origin, e.g. HEK 293, LLC-PK1, or of neuronal origin, e.g. SK-N-DZ, SK-N-BE(2), HCN-1A, NT2/D1.

The examples of the present invention are based on CHO cells. Therefore fibroblast derived cell lines such as BALB, NIH-3T3 and BHK cells are preferred.

It is preferred that the two heterologous conjugates are introduced into the cell as plasmids, e.g. two individual plasmids mixed upon application to cells with a suitable transfection agent such as Fugene (see Example 3, Example 4, Example 5 and Example 6) so that transfected cells express and integrate both the first and the second heterologous conjugates simultaneously. Many other means for introduction of one or both of the conjugates are evenly feasible e.g. electroporation, calcium phosphate precipitate, microinjection, adenovirus and retroviral methods, bicistronic plasmids encoding both conjugates etc.

Throughout the present invention, the term "protein" should have the general meaning. That includes not only the translated product, but also chemically synthesised proteins. For proteins translated within the cell, the naturally, or induced, post-translational modifications such as glycosylation and lipidabon are expected to occur and those products are still considered proteins.

The term intracellular protein interaction has the general meaning of an interaction between two proteins, as described above, within the same cell. The interaction is due to non-covalent forces between the protein components, most usually between one or more regions or domains on each protein whose physico-chemical properties allow for a more or less specific recognition and subsequent interaction between the two protein, components involved. In a preferred embodiment, the intracellular interaction is a protein-protein binding.

The luminophore allows the spatial distribution of the component to be visualised and/or recorded by emitting light. In a preferred aspect of the invention, the luminophore is capable of being redistributed in substantially the same manner as the component. In yet another embodiment of the invention, the luminophore is capable of being quenched upon spatial association with a component which is redistributed by modulation of the pathway, the quenching being measured as a change in the intensity or lifetime of the luminescence.

In a preferred aspect, the luminophore is a fluorophore. In a preferred embodiment of the invention, the luminophore is a polypeptide encoded by and expressed from a nucleotide sequence harboured in the cell or cells. E.g. the luminophore is a part of a hybrid polypepbde comprising a fusion of at least a portion of each of two polypeptides one of which comprises a luminescent polypeptide and the other one of which comprises the component. As the examples are carried out with GFP, GFP is especially preferred.

In the present context, the term "green fluorescent protein" (GFP) is intended to indicate a protein which, when expressed by a cell, emits fluorescence upon exposure to light of the correct excitation wavelength (e.g. as described by Chalfie, M. et al. (1994) Science 263, 802-805). Such a fluorescent protein in which one or more amino acids have been substituted, inserted or deleted is also termed "GFP". "GFP" as used herein includes wild-type GFP derived from the jelly fish *Aequorea victoria*, or from other members of the Coelenterata, such as the red fluorescent protein from *Discosoma* sp. (Matz, M. V. et al. 1999, Nature Biotechnology 17: 969-973) or fluorescent proteins from other animals, fungi or plants, and modifications of GFP, such as the blue fluorescent variant of GFP disclosed by Heim et al. (Heim, R. et al., 1994, Proc. Natl. Acad. Sci. 91:26, pp 12501-12504), and other modifications that change the spectral properties of the GFP fluorescence, or modifications that exhibit increased fluorescence when expressed in cells at a temperature above about 30° C. described in PCT/DK96/00051, published as WO 97/11094 on Mar. 27, 1997 and hereby incorporated by reference, and which comprises a fluorescent protein derived from Aequorea Green Fluorescent Protein or any functional analogue thereof, wherein the amino acid in position 1 upstream from the chromophore has been mutated to provide an increase of fluorescence intensity when the fluorescent protein of the invention is expressed in cells. Preferred GFP variants are F64L-GFP, F64L-Y66H-GFP F64L-S65T-GFP, F64L-E222G-GFP. One especially preferred variant of GFP for use in all the aspects of this invention is EGFP (DNA encoding EGFP which is a F64L-S65T variant with codons optimized for expression in mammalian cells is available from Clontech, Palo Alto, plasmids containing the EGFP DNA sequence, cf. GenBank Acc. Nos. U55762, U55763). Another especially preferred variant of GFP is F64L-E222G-GFP. As used in the examples, the detectable group preferably is a green fluorescent protein (GFP). The GFP is preferably selected from the group consisting of GFPs having the F64L mutation as defined herein such as F64L-GFP, F64L-Y66H-GFP, F64L-S65T-GFP, EGFP, and F64L-E222G-GFP. The GFP is N- or C-terminally tagged, optionally via a peptide linker, to the biologically active polypeptide or a part or a subunit thereof.

In an alternative embodiment the detectable groups is labelled with chemical fluorophores either in situ or by microinjection or otherwise introduced into cells. In yet another embodiment the detectable group comprises an epitope for antibodies, which are themselves detectable by other methods, either because they are tagged with a fluorophore, or may be detected by a biotin-streptavidin labelling method, or by secondary antibodies labelled with fluorophores etc. Examples of such epitopes detectable tag such as the myc or flag antigens, which may then be detected with antibodies, which are themselves detectable by other methods, either because they are tagged with a fluorophore, or may be detected by a biotin-streptavidin labelling method, or by secondary antibodies labelled with fluorophores etc.

Internal structure as used herein refers to a separate, discreet, identifiable component contained within a cell. Such internal structures are, in general, anatomical structures of the cell in which they are contained. Examples of internal structures include both structures located in the cytosol or cytoplasm outside of the nucleus (also called cytoplasmic structures) and structures located within the nucleus (nuclear structures). The nucleus itself including the nuclear membrane is an internal structure.

The recording of the detectable group will vary with the detectable group chosen. For example, when GFP is used as a detectable group the emitted light can be measured with various apparatus known to the person skilled in the art. Typically such apparatus comprises the following components: (a) a light source, (b) a method for selecting the wavelength(s) of light from the source which will excite the luminescence of the luminophore, (c) a device which can rapidly block or pass the excitation light into the rest of the system, (d) a series of optical elements for conveying the excitation light to the specimen, collecting the emitted fluorescence in a spatially resolved fashion, and forming an image from this fluorescence emission (or another type of intensity map relevant to the method of detection and measurement), (e) a bench or stand which holds the container of the cells being measured in a predetermined geometry with respect to the series of optical elements, (f) a detector to record the light intensity, preferably in the form of an image, (g) a computer or electronic system and associated software to acquire and store the recorded information and/or images, and to compute the degree of redistribution from the recorded images.

In a preferred embodiment of the invention the apparatus system is automated. In one embodiment the components in d and e mentioned above comprise a fluorescence microscope. In one embodiment the component in f mentioned above is a CCD camera. In one embodiment the component in f mentioned above is an array of photomultiplier tubes/devices.

In one embodiment of the invention the actual fluorescence measurements are made in a standard type of fluorometer for plates of microtiter type (fluorescence plate reader).

In one embodiment the optical scanning system is used to illuminate the bottom of a plate of microtiter type so that a time-resolved recording of changes in luminescence or fluorescence can be made from all spatial limitations simultaneously.

In one embodiment the image is formed and recorded by an optical scanning system. In a preferred embodiment the actual luminescence or fluorescence measurements are made in a FLIPR™ instrument, commercially available from Molecular Devices, Inc.

The quantitative information which is indicative of the degree of the cellular response to the influence or the result of the influence on the intracellular pathway is extracted from the recording or recordings according to a predetermined calibration based on responses or results, recorded in the same manner, to known degrees of a relevant specific influence. Hereby the degree of redistribution caused by an influence is expressed as the dose of a relevant specific influence causing same degree of cellular response. By testing a unknown influence, e.g. new chemical entities or chemicals without known effect on the redistribution of the cellular component a screening assay for drugs with effect on redistribution is achieved.

Based on these scientific and intellectual findings, the present invention can among other things be useful to:
Create cellular assays to monitor interactions between cellular components at the intermolecular level. Create cellular assays to monitor transient interactions between cellular components.
Create cellular assays to monitor conditional interactions between cellular components.
Create cellular assays to monitor interactions between components that have low affinity for one another.
Create cellular test systems in which the mobility of specific molecular components, for example a species of signalling molecule, can conditionally be restricted (locked down) to achieve a functional knockout of activity for that species.
Create cellular test systems in which the mobility of specific molecular components, for example a species of signalling molecule, can conditionally be released (dispersed) to achieve a functional knock-in of activity for that species.
Create a cellular system where interaction events between specific components are restricted to a specific location
Examples of uses are:
Cellular assays to find inhibitors of interactions
Cellular assays to find activators of interactions
Cellular assays to identify novel binding partners to any specific cellular component through screening of cDNA libraries.
Cellular assays to automatically screen active compounds for their ability to penetrate the cell membrane to provide an indication of likely bioavailability.
Cellular assays to automatically screen compounds for stability in the cellular environment to provide an indication of compounds cellular metabolism and excretion over the period of the assay.
Cellular test systems to investigate the function of specific cellular components.
Cellular assays to identify the signalling pathways used by orphan receptors and/or orphan ligands.
Cellular assays in high throughput screening for interaction modulators.
Some features of the present invention:
Mammalian cell assays provide physiologically relevant context for interactions, to allow for the influence of factors which may modulate an interaction as they would in the native system, for instance as in cells in the intact human system.
The redistribution-trap idea is compatible with a variety of fluorescence imaging methods, using either live or chemically fixed cells.
The response of any of the assays based on the redistribution-trap idea can be monitored either continuously as a sequential series of measurements over time, to generate a time course for a response, or by single end-point measurement. Time course measurements require live cells throughout. End point measurements can be made on either live or chemically fixed cells.
The method is amenable to low as well as high throughput measurements.
The method is useful in mammalian cells. Mammalian cells, unlike cells of plant or fungal origin such as yeast cells, have no cell wall. A cell wall can prevent certain compounds from entering the cell.

The measurement of protein interactions described above is ideal for identification/screening of compounds modulating such interactions. In order to carry out such assays, and other assays in High Throughput, one aspect of the present invention relates to a method for measuring a change in mobility of a cellular component caused by an influence, the method comprising:
(a) contacting or incubating cells with and without the influence, the cells comprising a luminophore coupled to the cellular component;
(b) adding extraction buffer to the cells of step (a), the extraction buffer comprising a cellular fixation agent and a cellular permeabilisation agent; and
(c) measuring the light emitted from the luminophore from cells of step (b);

wherein a difference between light emitted from the cells with and without the influence indicates a difference in the mobility of the cellular component caused by the influence. The principle is to remove luminophore-component couplings that has either moved or not moved upon stimulation.

One major advantage of the present invention is that changes in mobility can be measured as a change in light intensity. As will be illustrated below, and as described in the examples, this technique allows Redistribution™ to be detected as a fluorescence intensity change.

A variety of instruments exist to measure light intensity. In a preferred aspect of the present invention, wherein the luminophore is GFP, the instrument for measuring the light emitted from the luminophore is a FLIPR (Molecular Devices). In an alternative embodiment, the light emitted from the luminophore is measured on a plate reader.

This technique has improved Redistribution™ assays like the NFkB assay (Example 11) and TRAP assays like PDE4A4-trap (Example 10 and Example 12) from a screen time of 4 hrs per plate (imaging) to app. 30 sec. per plate (that is 480 times faster).

Throughout this application the change in mobility is characterized in that the component is substantially immobile either prior to contact or incubation with the influence or after contact or incubation with the influence. Substantially immobile is defined as the component will not move outside of the detection field during the extraction procedure.

The detection field, when the cells are washed after extraction, will In essence be the cells (or whatever is left of the cells when permeabilized and chemically fixed). In the typical scenario, the change in mobility of the component is caused by the component being associated with or adhered to a cellular compartment. For example, the majority of PKAcat-GFP in the inactive form aggregates as spots in the cytoplasm. Upon activation the PKAcat spots dissolve into the cytosol where the individual PKAcat molecules are much more mobile.

In one aspect of the invention the immobility is caused by binding of the component to a binding partner with unknown intracellular distribution. In this embodiment of the invention, the binding partner is fused to a protein with known substantially immobile intracellular distribution and the component is still coupled to the luminophore. Thus, binding between the component and the binding partner will cause the component to be substantially immobile.

In one aspect the change in mobility is a change from a soluble cytoplasmic state to an attached cytoplasmic state. That is, attached to organelles, e.g. attached to IR. In another aspect the change in mobility is a change from an attached cytoplasmic state to a soluble cytoplasmic state.

In one aspect the change in mobility is a change from a soluble cytoplasmic state to a state wherein the component is attached to the cellular membrane. In another aspect the change in mobility is a change from a state wherein the component is attached to the cellular memebrane to a state wherein the component is soluble in the cytoplasm.

In one aspect the change in mobility is a change from a soluble cytoplasmic state to a state wherein the component is attached to, or incorporated in, the nucleus. In another aspect the change in mobility is a change from a state wherein the component is attached to, or incorporated in, the nucleus to a soluble cytoplasmic state.

In one aspect the change in mobility is a change from an attached cytoplasmic state to a state wherein the component is attached to, or incorporated in, the nucleus. In another aspect the change in mobility is a change from a state wherein the component is attached to, or incorporated in, the nucleus to an attached cytoplasmic state.

Attachment in the cell is anticipated to be mediated by an internal structure e.g. organelle, membrane, cytoskeleton, or a molecular structure.

It is preferred that the cellular component is taking part in an intracellular signalling pathway, such as enzymes involved in the intracellular phosphorylation and dephosphorylation processes including kinases, protein kinases and phosphatases, but also proteins making up the cytoskeleton play important roles in intracellular signal transduction. In a more preferred embodiment, the cellular component is a protein kinase, a protein phosphatase, or a transcription factor.

In a preferred embodiment of the invention, the influence is contact between the mechanically intact living cell or the group of mechanically intact living cells with a chemical substance and/or incubation of the mechanically intact living cell or the group of mechanically intact living cells with a chemical substance.

In one embodiment, the invention is used as a basis for a screening program, where the effect of unknown influences such as a compound library, can be compared to influence of known reference compounds under standardised conditions.

The extraction buffer comprises a cellular fixation agent and a cellular permeabilisation agent.

In one aspect of the invention the cellular fixation agent is one, or a mixture of, protein coagulants or protein cross-linking agents, such as ethanol, acetic acid, acrolein, formaldehyde, glutaraldehyde, potassium permanganate, tannic acid, paraformaldehyde. Most preferred fixation agent is formalin.

In another aspect of the invention the cellular permeabilisation agent is a, or a mixture of, agents capable of perforating the plasma membrane of the cell such as Streptolysin O, or a anionic, non-ionic, zwitterionic or cationic detergent or detergent buffer such as lauryl sulphate, deoxycholic acid, digitonin, pluronic F68, Saponin, Triton X-100, Triton X-114, nonidet P40, CHAPS, hexadecyltrimethylammonium bromide or an agent inducing osmotic shock like salt or digitoxin. The most preferred permeabilisation agent is Triton X-100.

Any basic buffer that supports the cell type suitable for the experiment can be used. One preferred basic buffer is ordinary PBS. The final wash buffer should be carefully buffered at a pH suitable for obtaining maximal fluorescence from GFP, e.g. between pH 7.5 and 9.0, most preferably at pH 8.5. The buffering capacity should be sufficient to counteract the effects of trace amounts of formalin and Hoechst stain that may remain in or around cells after washing.

The ratio between the fixation agent and the permeabilisation agent is of essential importance. On the one side, the cell must be permeabilised to let the mobile component diffuse of out the cell; on the other side, the cell must be chemically fixed to prevent all cellular compartment to diffuse. As illustrated in Examples 10 to 12, it is of highest importance to optimized the ratio in each case since the optimal ratio depends on the cell type and, more importantly, the component and the kind of immobility (as discussed previously). An extraction buffer comprising 0.1% Formaldehyde and 0.1% Triton-X turns out to be a good starting point as that will, in our hands, always improve the assay even though these concentrations might not be optimal.

In order to optimize the ratio between the cellular fixation agent and a cellular permeabilisation agent, the following steps are performed:
(a) contacting with the reference compound cells comprising a luminophore;
(b) contacting or incubating without the reference compound cells similar to the cells in (a);
(c) adding extraction buffer, the extraction buffer comprising a cellular fixation agent and a cellular permeabilisation agent, to the cells in (a) and (b);
(d) measuring the light emitted from the luminophore;
(e) repeating steps (a) through (d) with extraction buffers with various concentrations of cellular fixation agent and cellular permeabilisation agent;

(f) calculating the signal to noise (s/n) ratio as (fluorescence in stimulated cells minus the fluorescence in non-stimulated cells) divided by the fluorescence in the non-stimulated cells times 100% for each of the extraction buffers tested in step (e); the optimized extraction buffer being the buffer associated with the highest signal to noise ratio.

The reference compound is a compound known to cause high degree of change in mobility of the component.

A method for decreasing background fluorescence when measuring intracellular redistribution comprising the steps of:
(a) contacting or incubating with a substance a mechanically intact living cell or mechanically intact living cells comprising a luminophore, the luminophore being capable of being redistributed in a manner which is related to the influence of the substance, and/or of being associated with a component which is capable of being redistributed in a manner which is related to the influence of the substance;
(b) adding extraction buffer, the extraction buffer comprising a cellular fixation agent and a cellular permeabilisation agent to the cells; and
(c) measuring the distribution of spatially distributed light.

EXAMPLES

Example 1

Construction of the Probes and Fusions

PS462 contains a fusion of PDE4A4 and EGFP under the control of a CMV promoter and has resistance to G418 as selectable marker. To construct the PDE4A4-EGFP fusion, the ca. 1.9 kb C-terminal part of HSPDE4A4 (GenBank Acc. no. L20965), which is common to all PDE4A isoforms, is amplified using PCR with primers 4A-Ct-top and 4A-bottom described below. The sequence of the top primer contains a silent mutation, which introduces a Dra1 site exactly at the beginning of the shared 4A region. The bottom primer includes the common C-terminal sequence minus the stop codon, a BamH1 cloning site, and two extra nucleotides to preserve the reading frame when cloned into pEGFP-N1. The unique ca. 0.8 kb N-terminal part of HSPDE4A4 is amplified using PCR in the presence of 5% DMSO with primers 4A4-top and 4A4N-bottom described below. The top primer includes specific HSPDE4A4 sequences following the ATG, a Kozak sequence, and a Hind3 cloning site. The bottom primer spans the junction of the unique 4A4 N-terminal part and the common 4A C-terminal part, and it contains a silent mutation that introduces a Dra1 site exactly at the beginning of the shared 4A region. The PCR products are digested with the relevant restriction enzymes (Hind3 and Dra1 for the unique N-terminal part and Dra1 and BamH1 for the common C-terminal part), and ligated together into pEGFP-N1 (Clontech, Palo Alto; GenBank Accession number U55762) digested with Hind3 and BamH1. This produces a PDE4A4-EGFP fusion under the control of a CMV promoter. The resulting plasmid is referred to as PS462 (deposited under the Budapest Treaty with Deutsche Sammiung von Mikroorganismen und Zellkulturen GmbH (DSMZ) on Apr. 17, 2000 with DSM 13450).

4ACt-top: 5'-GTTTAAAAGGATGTTGAACCGT-GAGCTC-3' (SEQ ID NO: 7)
4A-bottom: 5'-GTGGATCCCAGGTAGGGTCTCCAC-CTGA-3' (SEQ ID NO: 8)
4A4-top: 5'-GTAAGCTTGCGCCATGGAAC-CCCCGACC-3' (SEQ ID NO: 9)
4A4N-bottom: 5'-GGTTTTAAACTTGTGCGAGGC-CATCTCGCTGAC-3' (SEQ ID NO: 10)

Plasmid PS642 contains a fusion of PDE4A4 and SOS1 under the control of a CMV promoter, and has resistance to zeocin as selectable marker. PS642 is derived from PS614, which is derived from PS462. PS462 is constructed as described above. The neomycin resistance marker on PS462 is replaced with a zeocin resistance marker by digesting PS462 with Avr2, which excises neomycin, and ligating the vector fragment with a ca 0.5 kb Avr2 fragment encoding zeocin resistance. This fragment is isolated by PCR using primers 9655 and 9658 described below with pZeoSV (Invitrogen) as template. Both primers contain Avr2 cloning sites, and flank the zeocin resistance gene including its E. coli promoter. The top primer 9658 spans the Ase1 site at the beginning of zeocin, which can be used to determine the orientation of the Avr2 insert relative to the SV40 promoter which drives resistance in mammalian cells. The resulting plasmis is referred to as PS614.

9658-top: TCCTAGGCTGCAGCACGTGTTGACAAT-TAATCATCGG-3' (SEQ ID NO: 11)
9655-bottom: TCCTAGGTCAGTCCTGCTCCTCGGC-CACGAAGTGCAC-3' (SEQ ID NO: 12)

The coding sequence of human SOS1 (GenBank accession number NM_005633) is isolated from e.g. a human fetus or brain cDNA library by PCR with primers 0099 and 0100 described below. The top primer includes specific SOS1 sequences following the ATG and a BamH1 cloning site. The bottom primer includes specific SOS1 sequence including the stop codon and a Not1 cloning site. The PCR product is digested with restriction enzymes BamH1 and Not1, and ligated into PS614 vector DNA digested with BamH1 and Not1. This creates a fusion between PDE4A4 and SOS1 under the control of a CMV promoter. The resulting plasmid is referred to as PS642.

0099-top: 5'-GTTGGATCCCATGCAGCAGGCGCCG-CAGCCTTAC-3' (SEQ ID NO: 13)
0100-bottom: 5'-GTTGCGGCCGCTCATTGGG-GAGTTTCTGCATTTTC-3' (SEQ ID NO: 14)

Plasmid PS587 contains a fusion of GRB2 and EGFP under the control of a CMV promoter, and has neomycin resistance as selectable marker. The coding sequence of human GRB2 (GenBank accession number NM_002086) is isolated from e.g. a human fetus or brain or placenta cDNA library by PCR with primers 0073 and 0074 described below. The top primer includes specific GRB2 sequences following the ATG and a Hind3 cloning site. The bottom primer includes specific GRB2 sequence including the stop codon and an EcoR1 cloning site. The PCR product is digested with restriction enzymes Hind3 and EcoR1, and ligated into pEGFP-N1 vector DNA (Clontech, Palo Alto, GenBank Accession number U55672) digested with Hind3 and EcoR1. This creates a fusion between GRB2 and EGFP under the control of a CMV promoter. The vector may optionally first have been modified to contain a T7 promoter (which can be used for in vitro transcription) immediately upstream of EGFP. This can be achieved by digesting pEGFP-N1 with restriction enzymes Nhe1 and Bgl2, which cut Immediately upstream of EGFP, and ligating the vector fragment with annealed oligos 9949 & 9950. The resulting plasmid is referred to as PS587.

0073-top: 5'-GCGAAGCTTTCAGAATGGAAGCCATCG-3' (SEQ ID NO: 15)
0074-bottom: 5'-GCCGAATTCGGACGTTCCGGT-TCACG-3' (SEQ ID NO: 16)
9949: 5'-CTAGCATTAATACGACTCACTATAGGGA-3' (SEQ ID NO: 17)

9950:  5'-GATCTCCCTATAGTGAGTCGTATTAATG-3' (SEQ ID NO: 18)

Plasmid PS639 contains a fusion of the catalytic subunit of PKA (PKAcat) and GRB2 under the control of a CMV promoter, and has resistance to zeocin as selectable marker. PS639 is derived from PS610, which is derived from PS457.

Plasmid PS457 contains a fusion of PKAcat and EGFP under the control of a CMV promoter, and has neomycin resistance as selectable marker. The coding sequence of human PKAcat (GenBank accession number X07767) except the 17 N-terminal amino acids is isolated from e.g. a human liver or spleen cDNA library by PCR with primers 9952 and 9922 described below. The top primer includes specific PKAcat sequences spanning an EcoR1 site near the N-terminus of the coding sequence. The bottom primer includes specific PKAcat sequence minus the stop codon and a BamH1 cloning site. The PCR product is digested with restriction enzymes EcoR1 and BamH1, and ligated into pEGFP-N1 vector DNA (Clontech, Palo Alto, GenBank Accession number U55672) digested with EcoR1 and BamH1. This intermediate is digested with Hind3 and EcoR1 and ligated with annealed oligos 9955 and 9956, which adds remaining N-terminal amino acids to PKAcat, and so creates a fusion between PKAcat and EGFP under the control of a CMV promoter. This construct is referred to as PS457.

9952-top: 5'-GAGCGTGAAAGAATTCTTAGCCAAAG-3' (SEQ ID NO: 19)

9922-bottom: 5'-GTGGATCCCAAAACTCAGAAAACTCCTTG-3' (SEQ ID NO: 20)

9955: 5'AGCTTCCGCGATGGGCAACGCCGCCGCCGCCAAGAAGGGCAGCGAGCAGGAGAGCGTGAAAG-3' (SEQ ID NO: 21)

9956: 5'AATTCTTTCACGCTCTCCTGCTCGCTGCCCTTCTTGGCGGCGGCGTTGCCCATCGCGGA-3' (SEQ ID NO: 22)

PS610 is constructed by replacing neomycin resistance on PS457 with zeocin resistance as described above.

The coding sequence of human GRB2 is isolated from PS587 described above by PCR with primers 0143 and 0142 described below. The top primer includes specific GRB2 sequences following the ATG and a BamH1 cloning site. The bottom primer includes specific GRB2 sequence including the stop codon and an Xba1 cloning site. The PCR product is digested with restricton enzymes BamH1 and Xba1, and ligated into PS610 vector DNA (isolated from a dam-minus *E. coli*) digested with BamH1 and Xba1. This creates a fusion between PKAcat and GRB2 under the control of a CMV promoter. The resulting plasmid is referred to as PS639.

0143-top: 5'-GTTGGATCCCATGGAAGCCATCGCCAAATATG-3' (SEQ ID NO: 23)

0142-bottom: 5'-GTTTCTAGATTAGACGTTCCGGTTCACGG-3' (SEQ ID NO: 24)

Plasmid PS602 contains a fusion of EGFP and the 265 C-terminal amino acids of SOS1 under the control of a CMV promoter, and the neomycin resistance marker. A C-terminal part of the coding sequence of human SOS1 (GenBank accession number NM_005633) is isolated from e.g. a human fetus or brain cDNA library by PCR with primers 0122 and 0123 described below. The top primer includes specific SOS1 sequences following amino acid number 1067 plus an ATG and an Xho1 cloning site. The bottom primer includes specific SOS1 sequence including the stop codon and a BamH1 cloning site. The PCR product is digested with restriction enzymes Xho1 and BamH1, and ligated into pEGFP-C1 vector DNA (Clontech, Palo Alto, GenBank Accession number U55673) digested with Xho1 and BamH1. This creates a fusion between EGFP and a C-terminal part of SOS1 under the control of a CMV promoter. The vector may optionally first have been modified to contain a T7 promoter (which can be used for in vitro transcription) immediately upstream of EGFP as described above. The resulting plasmid is referred to as PS602.

0122: 5'-GTTCTCGAGTCATGAGCTTTAGTCGGATTGCTG-3' (SEQ ID NO: 25)

0123: 5'-GTTGGATCCTCATTGGGGAGTTTCTGCATTTTC-3' (SEQ ID NO: 26)

Plasmid PS628 contains a fusion of the Cys1 domain of PKCgamma and GRB2 under the control of a CMV promoter, and has resistance to zeocin as selectable marker. PS628 is derived from PS613, which is derived from PS443.

Plasmid PS443 contains a fusion of the 90 N-terminal amino acids of human PKCgamma (the Cys1 domain) and EGFP under the control of a CMV promoter, and has neomycin resistance as selectable marker. The Cys1 domain of human PKCgamma (GenBank accession numbers M13977 and Z15114) is isolated from e.g. a human brain cDNA library by PCR with primers 9916 and 9935 described below. The top primer includes specific PKCgamma sequences spanning the ATG and an EcoR1 cloning site. The bottom primer includes specific PKCgamma sequence around amino acid number 90 and an Acc65 cloning site. The PCR product is digested with restriction enzymes EcoR1 and Acc65, and ligated into pEGFP-N1 vector DNA (Clontech, Palo Alto, GenBank Accession number U55672) digested with EcoR1 and Acc65. This creates a fusion between PKCgamma-Cys1 and EGFP under the control of a CMV promoter. This construct is referred to as PS443.

9916: 5'-GTGAATTCGGCCATGGCTGGTC-3' (SEQ ID NO: 27)

9935: 5'-GTGGTACCTTCCCAGCGCCTGGACACTC-3' (SEQ ID NO: 28)

PS613 is constructed by replacing neomycin resistance on PS443 with zeocin resistance as described above.

The coding sequence of human GRB2 is isolated from PS587 described above by PCR with primers 0143 and 0142 described below. The top primer includes specific GRB2 sequences following the ATG and a BamH1 cloning site. The bottom primer includes specific GRB2 sequence including the stop codon and an Xba1 cloning site. The PCR product is digested with restriction enzymes BamH1 and Xba1, and ligated into PS610 vector DNA (isolated from a dam-minus *E. coli*) digested with BamH1 and Xba1. This creates a fusion between Cys1 and GRB2 under the control of a CMV promoter. The resulting plasmid is referred to as PS628.

0143-top: 5'-GTTGGATCCCATGGAAGCCATCGCCAAATATG-3' (SEQ ID NO: 23)

0142-bottom: 5'-GTTTCTAGATTAGACGTTCCGGTTCACGG-3' (SEQ ID NO: 24)

To construct the HSPDE4A1-EGFP fusion, the ca. 1.95 kb coding region of HSPDE4A1 (GenBank Acc. no. U97584) is amplified using PCR and primers 4A1-top and 4A-bottom described below. The top primer includes specific HSPDE4A1 sequences following the ATG, a Kozak sequence, and a Hind3 cloning site. The bottom primer includes the common PDE4A C-terminal sequence minus the stop codon, a BamH1 cloning site, and two extra nucleotides to preserve the reading frame when inserted into in pEGFP-N1. The PCR product is digested with restriction enzymes Hind3 and BamH1, and cloned into pEGFP-N1 (Clontech, Palo Alto; GenBank Accession number U55762)

cut with Hind3 and BamH1. This produces an HSPDE4A1-EGFP fusion under the control of the CMV promoter. The resulting plasmid is referred to as PS461 and is deposited under the Budapest Treaty with Deutsche Sammiung von Mikroorganismen und Zellkulturen GmbH (DSMZ) on Apr. 17, 2000 with DSM 13449.

4A1-top: 5'-GTAAGCTTAAGATGCCCTTGGTG-GATTTCTTC-3' (SEQ ID NO: 29), specific for PDE4A1, 4A-bottom: 5'-GTGGATCCCAGGTAGGGTCTCCAC-CTGA-3' (SEQ ID NO: 8)

| SEQ ID NO: | Description |
|---|---|
| 1 | DNA sequence of PDE4A4 as it appears in PS462 from start codon to BamH1 cloning site in 3'-end. |
| 2 | Protein sequence of PDE4A4 as it appears in PS462. |
| 3 | DNA sequence of PDE4A1 as it appears in P3461, from start codon to BamH1 cloning site at 3'-end. |
| 4 | Protein sequence of PDE4A1 as it appears in PS461. |
| 5 | DNA sequence of SOS1 as it appears in PS642, from start codon to stop codon. |
| 6 | Protein sequence of SOS1 as it appears in PS642. |

Example 2

Protocols and Methods

This example describes protocols and methods used for in vivo expression of the probes described in Example 1, and the visualisation and measurement of changes undergone by EGFP fusion probes, either transfected singly or as co-transfections with anchor probes in CHO cells.

Transfection and Cell Culture:

Chinese hamster ovary cells (CHO), are transfected with the plasmids described in Example 1 above, either using a single species of plasmid, or pairs of plasmids co-transfected simultaneously, using the transfection agent FuGENE™ 6 (Boehringer mannheim Corp, USA) according to the method recommended by the suppliers. Stable transfectants of single GFP probes are selected using the appropriate selection agent, usually 0.5 mg/ml G418 sulphate (Calbiochem) in the growth medium (HAM's F12 nutrient mix with Glutamax-1, 10% foetal bovine serum (FBS), 100 μg penicillin-streptomycin mixture $ml^{-1}$ (GibcoBRL, supplied by Life Technologies, Denmark). Co-transfected cells are cultured in the same medium but with the addition of a two selection agents appropriate to the plasmids being used, usually 0.5 mg/ml G418 sulphate plus 1 mg/ml zeocin. Cell are cultured at 37° C. in 100% humidity and conditions of norrnal atmospheric gases supplemented with 5% $CO_2$.

Clonal cell lines with particular properties are sub cultured from mixed populations of stably transfected cells by isolating individual cells and removing them to sterile culture flasks containing fresh culture medium with 0.5 mg/ml G418 sulphate or 0.5 mg/ml G418 sulphate+1 mg/ml zeocin as appropriate to the plasmid(s) being selected.

For fluorescence microscopy, cells are allowed to adhere to Lab-Tek chambered coverglasses (Nalge Nunc International, Naperville USA) for at least 24 hours and are then cultured to about 80% confluence. Cells can also be grown in plastic 96-well plates (Polyfiltronics Packard 96-View Plate or Costar Black Plate, clear bottom; both types tissue culture treated) for imaging purposes. Prior to experiments, the cells are cultured over night without selection agent(s) in HAM F-12 medium with glutamax, 100 μg penicillin-streptomycin mixture $ml^{-1}$ and 10% FBS. This medium has low autofluorescence enabling fluorescence microscopy of cells straight from the incubator. For certain tests requiring medium of defined composition, particularly with regard to the presence of specific cell growth factors, the HAM's culture medium is replaced prior to imaging with a buffered saline solution (KRW buffer) containing (in mM) 3.6 KCl, 140 NaCl, 2 $NaHCO_3$, 0.5 $NaH_2PO_4$, 0.5 $MgSO_4$, 1.5 $CaCl_2$, 10 Hepes, 5 glucose, pH7.4.

Confocal Imaging:

Confocal images are collected using a Zeiss LSM 410 microscope (Carl Zeiss, Jena, Germany) equipped with an argon ion laser emitting excitation light at 488 nm. In the light path are a FT510 dichroic beamsplitter and a 515 nm long-pass filter or a 510 to 525 nm bandpass emission filter. Images are typically collected with a Fluar 40X, NA: 1.3 oil immersion objective, the microscope's confocal aperture set to a value of 10 units (optimum for this lens).

Time Lapse Sequences and Analysis:

Image sequences of live cells over time (time lapse, e.g. FIGS. 5, 6, 11, 12) are gathered using a Zeiss Axiovert 135M fluorescence microscope fitted with a Fluar 40x, NA: 1.3 oil immersion objective and coupled to a Photometrics CH250 charged coupled device (CCD) camera (Photometrics, Tucson, Ariz. U.S.A.). The cells are illuminated with a 100 W HBO arc lamp. In the light path are a 470±90 nm excitation filter, a 510 nm dichroic mirror and a 515±15 nm emission filter for minimal image background. The cells are maintained at 37° C. with a custom-built stage heater.

Time lapse response profiles are extracted from image sequences using a region of interest (ROI) defined over the same co-ordinates or pixels for each successive image in a sequence: pixel values are summed and averaged over the ROI in each image, and the resulting values plotted against image number to generate a time lapse response profile for that defined region of the sequence. A ROI can include many cells, a single cell, or a region within a single cell.

Automated Imaging and Analysis:

The amount of fluorescent spots and other accumulations of a transfected probe in a population of cells can be imaged and quantified in an automated fashion to yield a measure of mean number of spots per cell. For this purpose cells are cultured to near 80% to 90% confluence in coverglass chambers or plastic 96-well plates, given the relevant treatment and allowed to respond. At the end of the response period, cells are chemically fixed in 4% formaldehyde buffer (Lillies fixative buffer, pH7.4: Bie and Berntsen A/S, Denmark) for 30 minutes to 2 hours, and then washed three times in phosphate buffered saline (PBS, Life Technologies, Denmark). An alternative simultaneous fixation+permeabilisation method, useful to remove non-localised (i.e. mobile) GFP probe from the cytoplasm, involves a single fixation process incorporating 0.4% to 2% formaldehyde buffer (10% to 50% strength Lillies fixative) plus 0.2% to 1% Triton X-100. The actual concentrations used need to be optimised for the cell type being used; for CHO cells 2% formaldehyde+1% Triton X-100 gives excellent results. The combined fixative+detergent are applied to the cells for 10 to 20 minutes at room temperature. Cells are then washed three times with phosphate buffered saline. Nuclear DNA is stained with 10 μM Hoechst 33258 (Molecular Probes, Eugene, Oreg., U.S.A.) in PBS for 10 minutes at 25° C., then washed twice in PBS. Automated images are collected on a Nikon Diaphot 300(Nikon, Japan) using a Nikon Plan Fluor 20X/0.5NA objective lens. The basic microscope is fifted with a motorised specimen stage and motorised focus control (Prior Scientific, Fulbourn, Cambridge UK), excitation filter wheel (Sutter Instruments, Novato Calif. U.S.A.) and Photometrics PXL series camera with a KAF1400 CCD chip (Photometrics, Tucson, Ariz. U.S.A.), each of these items being under the control of a Macintosh 7200/90 computer (Apple Computer, Cupertino, Calif. U.S.A.). Automation of stage positioning, focus, excitation filter selection, and image acquisition is performed using macros written in-house, running under IPLab Spectrum for Macintosh (Scanalytics, Fairfax, Va. U.S.A.). Fluorescence illumination comes from a 100 W HBO lamp. Images are collected in pairs, the first using a 340/10 nm excitation filter, the second with a 475RDF40 excitation filter (Chroma, Brattleboro, Vt.). Both images are collected via the same dichroic and emission filters, which are optimised for EGFP applications (XF100 filter set, Omega Optical, Brattleboro, Vt.). While the choice of filters for imaging the nuclear stain (Hoechst 33258) is not well matched to that dye's spectral properties, resulting in lower image intensity, it greatly improves the throughput of the procedure by allowing both images to be collected using the same dichroic and emission filter. This eliminates any image registration problems and focus shifts which would result from using two different filter sets, which would require more steps in the acquisition procedure and more extensive image processing to overcome.

The necessary images are collected as follows: A holder containing four 8-well coverglass chambers, or a single 96-well plate, is loaded onto the microscope. The program is started, and the first well of cells is moved into position and manually coarse-focused by the operator. The image is fine-focused by an auto-focus routine using the 340/10 excitation. An image is captured and stored at this excitation wavelength (the nuclear image), and then a second image is captured and stored at the longer wavelength excitation (the GFP image). The stage is automatically repositioned and microscope automatically refocused to capture a second pair of images within the same well. This process is repeated a set number of times (typically 4 to 8) for the first well. The stage then advances the next well to the imaging position, and the process repeats itself until the set number of image pairs has been captured from each well of cells.

Figure 3:
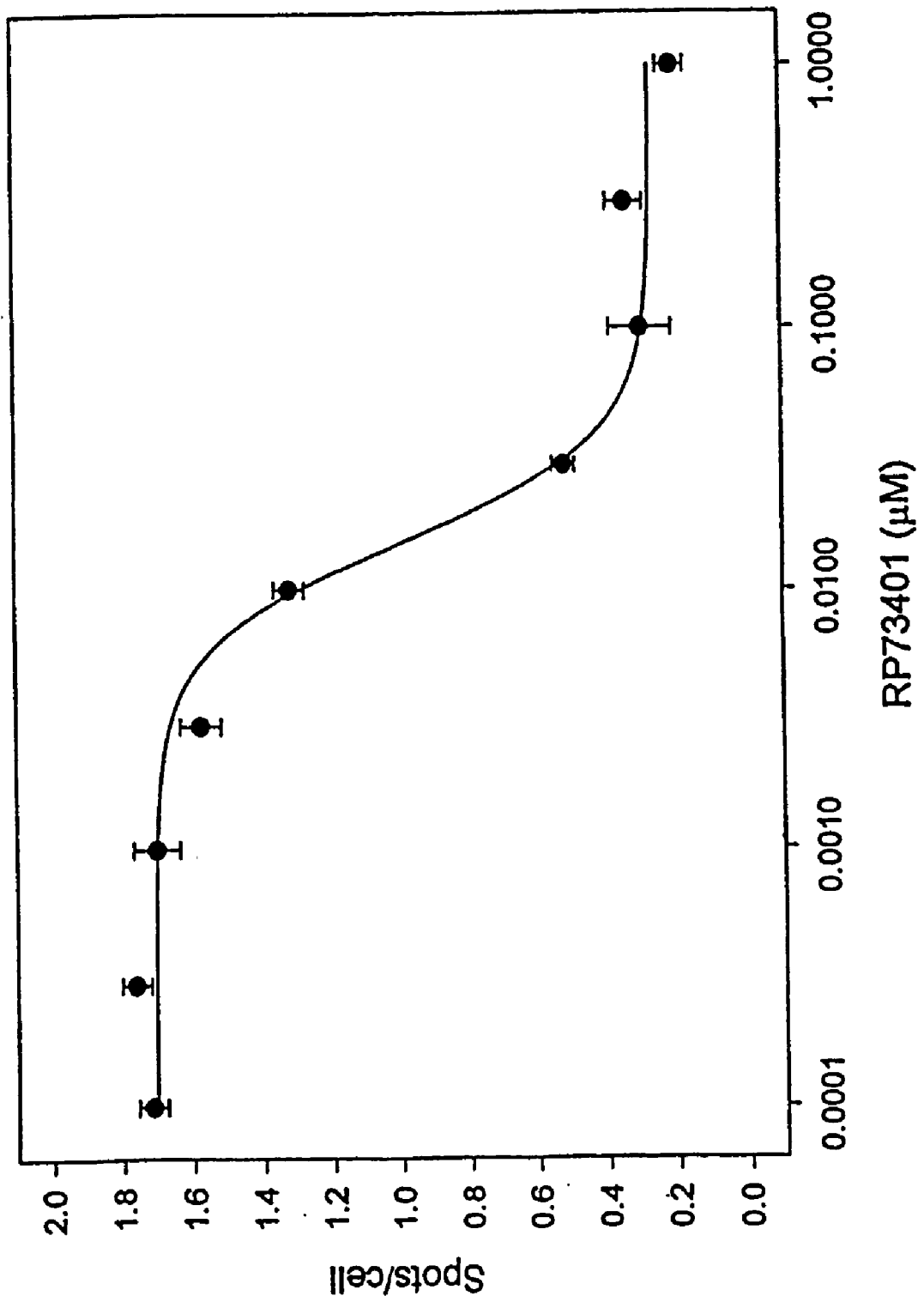

Image pairs are automatically analysed in the following way using a suite of macros running under the IPLab Spectrum software: First the nuclear image of a pair is filtered with a digital filter to simultaneously sharpen the edges of and suppress differences in intensity of the nuclei. The choice of filter, and the filter constants, were arrived at through experimentation with various data sets. The filtered image is then segmented at a pre-determined intensity value, such that pixels below this threshold are very likely not within a nuclear region, and pixels above this threshold are very likely within a nuclear region. The contiguous regions above the threshold are then counted, after rejecting contiguous regions that are larger than a certain area or smaller than a certain (different) area, the areas having been previously determined to provide a sufficiently accurate distinction between nuclei and other objects that are not nuclei. The final count is the estimated number of nuclei in the field. The GFP image of each pair is then digitally filtered with a filter chosen experimentally to suppress the variation of intensity due to the typical non-localised distribution of GFP, while accentuating the intensity of any bright point-like objects relative to this background. This filtered image is then segmented at a threshold that has been experimentally determined to divide the image into pixels that are very likely to be in a spot (above the threshold) and pixels that are very likely not to be in a spot (below the threshold). The contiguous regions of pixels that are above the threshold are counted, after rejecting regions that do not have certain morphological properties, which were previously determined to be characteristic of spots. The ratio of spot count to nuclear count for each pair represents an estimate of the average number of spots per cell in that image pair. All image pairs are treated in this way, and the final table of values is used to establish the cellular response to a given treatment. FIG. 3 is an example of how the effect of a compound upon spot density in CHO cells expressing HSPDE4A4-EGFP can be measured using the automated imaging and image analysis method.

Figure 4:
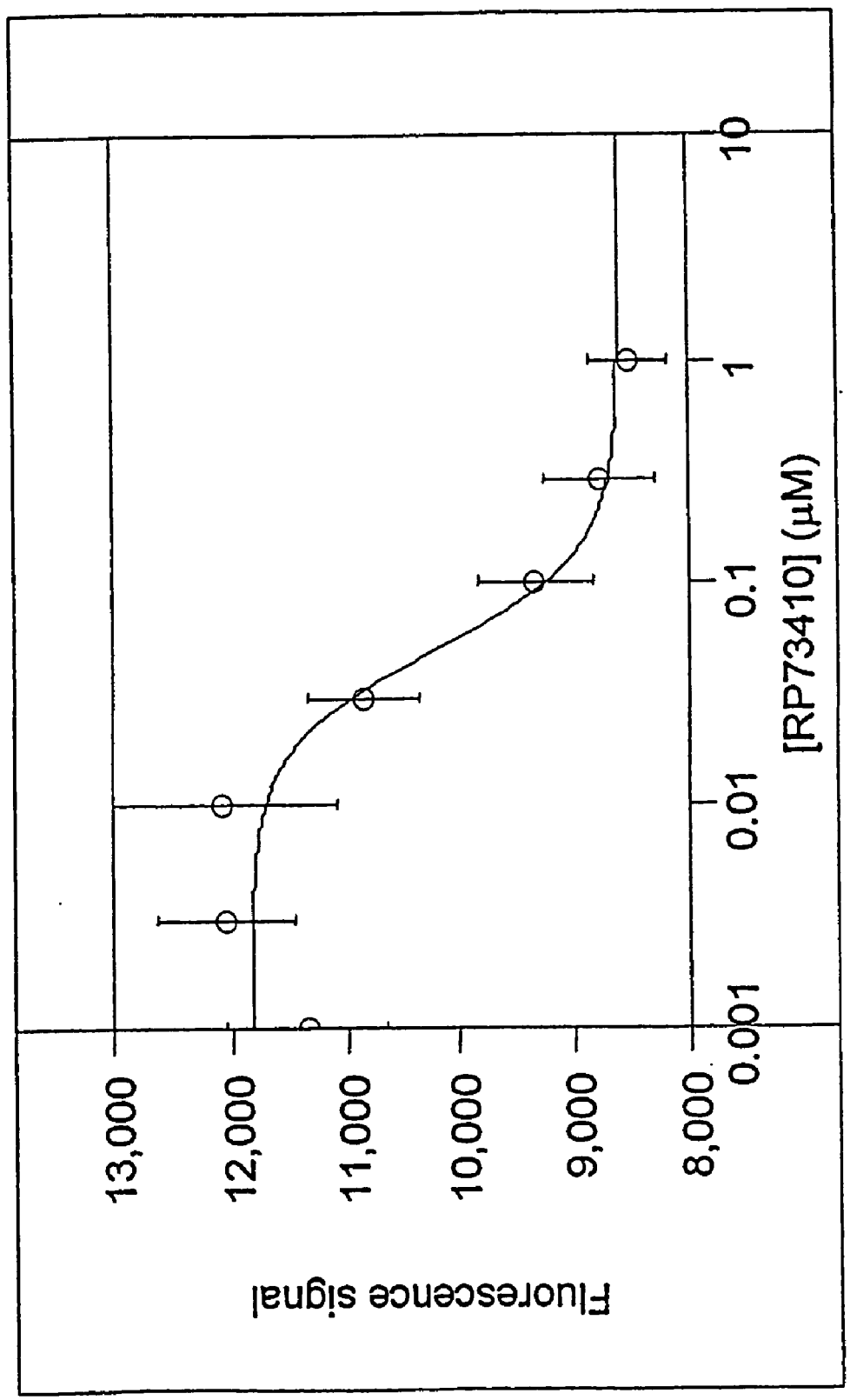

The amount of fluorescent spots and other accumulations of a transfected probe in a population of cells can also be quantified using a fluorescent plate reader, such as a TECAN Spectrafluor (Tecan U.S. Inc., Research Triangle Park, N.C. 27709, U.S.A.) or using a fluorescence imaging plate reader (FLIPR; Molecular Devices Corp., Sunnyvale, Calif. 94089, U.S.A.). The use of the combined fixation+permeabilisation method greatly improves the signal over background for measurements of spots and other accumulations in cells, particularly when the measurements are made on fluorescent plate readers. FIG. 4 is an example of the use of the FLIPR to measure the effect of a compound upon spot density in CHO cells expressing HSPDE4A4-EGFP. The cells were treated with the simultaneous fix and permeabilisation protocol to obtain these data.

Redistributions of fluorescent probes from cytoplasm to plasma membrane may be quantified by standard imaging methods using simple image analysis of the changes in fluorescence intensity of cytoplasmic ROIs. Similar redistributions may also be measured on the FLIPR, and even on standard fluorescent plate readers, especially those configured to measure signal from adherent cells in microtitre plates.

Figure 7:
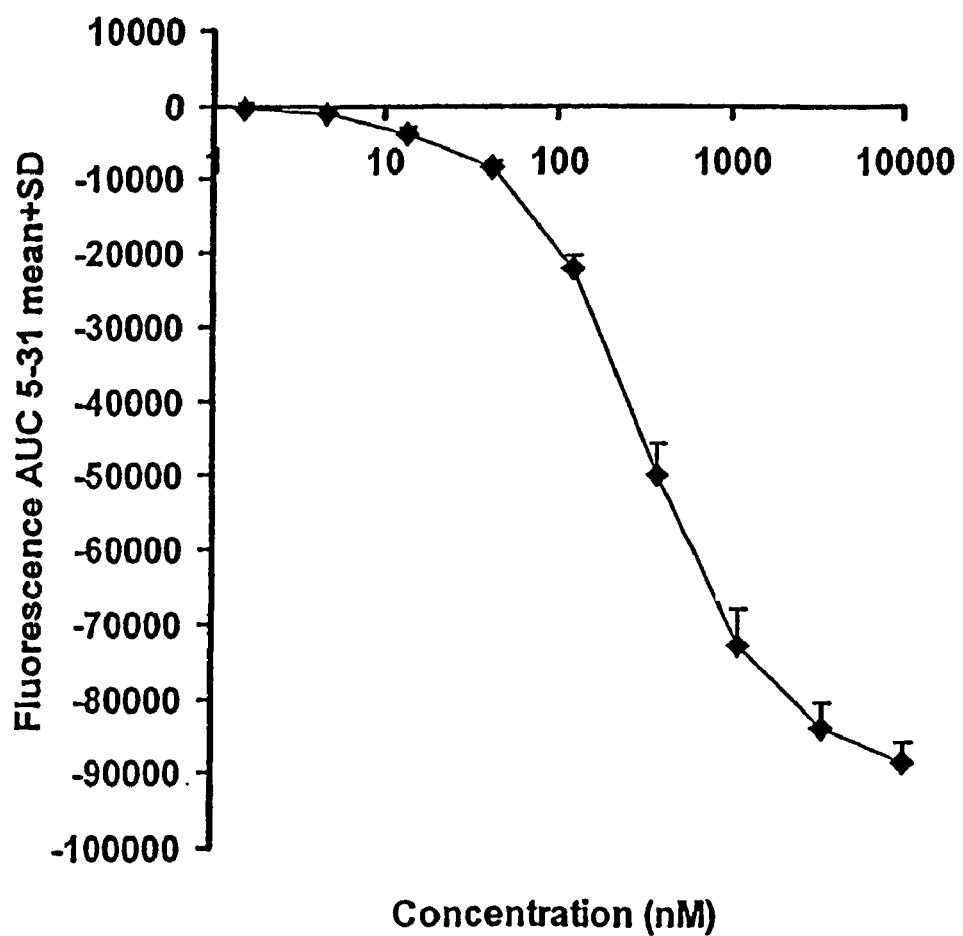

Use of the FLIPR to measure PKC-like redistributions (of which EGFP-Cysl(PKCy) is an example), and also PKAc-like redistributions, in real time, is detailed in an earlier patent AN IMPROVED METHOD FOR EXTRACTING QUANTITATIVE INFORMATION RELATING TO AN INFLUENCE ON A CELLULAR RESPONSE (WO 00/23615). FIG. 7 shows how the effect of a compound on the redistribution of Cys1γ-EGFP can be quantified using the FLIPR.

Example 3

Probes for Proteins X and Y with PDE4A4 Anchor Protein

The present example and Example 4, Example 5 and Example 6, describe generic ways to produce a cell line suitable for screening compounds targeting against a specific interaction between two partner components X and Y. In these examples the cells are derived from CHO cells co-transfected with two plasmids, one coding for fusion probes with X or Y attached to either the C or N terminal of the anchor moiety (the anchor probe), and the second with the other partner, Y or X, attached to either the C or N terminal of GFP (the detectable probe). There are therefore 4 possible anchor probes and 4 possible detectable probes that can be made for the interacting pair X-Y, and 8 useful combinations to co-transfect. Anchor and detectable probes use different selection markers to ensure that cells under selection maintain both plasmids; for example, the anchor may confer resistance to zeocin, the detectable to neomycin. Cells that maintain both probes under continuous selection (minimum of 2 weeks) are termed "stable".

Figure 2:
Figure 8:
Figure 8:
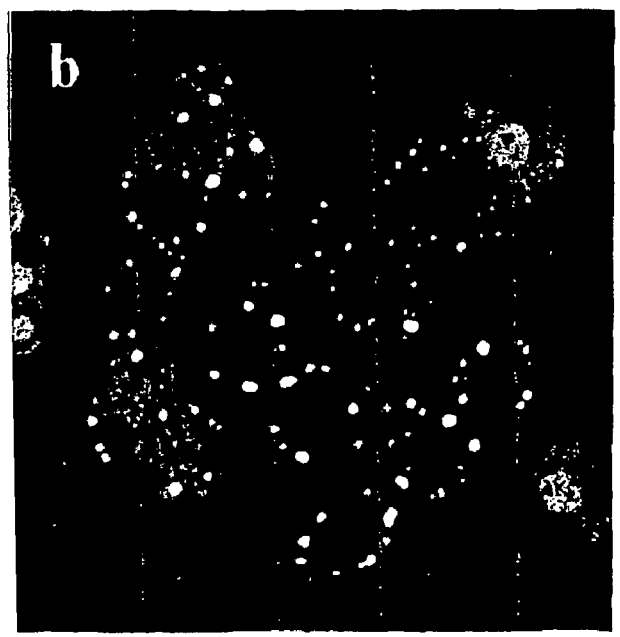

In this example the anchor probes are based on HSPDE4A4B (human phosphodiesterase type 4, isoform A, splice variant 4B: referred to hereafter as PDE4A4), which when treated with the PDE4 inhibitor rolipram forms a number of dense aggregates in the cytoplasm of each cell ($EC_{50}$ 0.2 to 0.3 µM). These rolipram-induced aggregates may be detected with an antibody directed against the unique C-terminal peptide sequence of HSPDE4A, as demonstrated in FIG. 10. In cells successfully transfected with a plasmid coding for a fusion protein having GFP fused to the C-terminal of PDE4A4, the fluorescence is distributed in a general and fairly even way within the cytoplasm (FIG. 1), but when treated with rolipram aggregates form and these are apparent as bright green fluorescent spots in the cell (FIG. 2). There are on average 2 such aggregates per rolipram-treated cell positioned diametrically opposite each other either side of the nucleus. After 10 to 16 hours of exposure to 10 µM rolipram these aggregates grow to about 2 to 4 µm in diameter. Removal of rolipram causes these aggregates to disperse within 60 minutes. Similar spots appear in PDE4A4-transfected cells if treated with the PDE4 inhibitors RS25344 ($EC_{50}$ 0.02 µM, Syntex) and Ro 20-1724 ($EC_{50}$ 4 µM, Roche). In cells co-transfected with PDE4A4-anchor probe-X plus EGFP-Y detectable probe, GFP-bright spots will only appear in cells after treatment with rolipram if X and Y interact and attract each other (FIG. 8). The spots will disappear (FIG. 9) when rolipram is removed, or competed against with RP73401 (Piclamilast, Rhone-Poulenc Rorer) another potent PDE4 inhibitor ($IC_{50}$ versus 3 µM rolipram approx. 20 nM, FIGS. 3 and 4).

Protocol for PDE4A4 Anchor System:
1) Co-transfect a PDE4A4 anchor-detectable pair into CHO
2) Check there are no GFP-bright spots to start. If there are spots, or other distinct distribution of GFP present, may still be worth testing cells at (3): a change in distribution must be seen in step (3) if this transfection is to be useful.
3) Test transients with 10 µM rolipram and (separately) with 1 µM RS25344, overnight
   a. spots appear: clone cells from transients and put under double selection (as in 4). Cells ready for screening when stable.
   b. no spots: wait for stable cell line to form from cells under double selection (see 4)
4) Make stable cell line using double selection (e.g. 1 mg/ml of zeocin plus 0.5 mg/ml neomycin/G418). Test separately with 10 µM rolipram and 1 µM RS25344
   a. spots appear: clone cells from stables under double selection ready for screening use.
   b. no spots: fix and stain (rolipram or RS25344-treated cells) with anti-4A antibody
      i. spots stain with antibody: go to (5)
      ii. no spots: anchor system not present or not working—repeat the co-tranfection or try another anchor system or orientation.
5) Test for conditional association (see A and B below).
6) If no association conditions are found, choose another combination of anchor/detectable pairs and start again.

Test for conditional association with an appropriate interaction stimulus: A and B can be done in parallel. B tests for possible conditions or associations that can only occur in the "soluble phase".

A i) incubate stables overnight with 10 M rolipram and separately with 1 M RS25344
   ii) test with an interaction stimulus, i.e. a treatment likely to bring pair together. NB this may need time-lapse to catch transients:
      a. spots appear clone cells from stables
      b. No spots: try (B)
B i) incubate stables overnight with 10 µM rolipram and separately with 1 µM RS25344
   ii) washout rolipram or RS, incubate 60 minutes (to allow PDE4A4 anchor to be liberated from its attachment)
   iii) test with an interaction stimulus, i.e. a treatment likely to bring pair together, together with (or followed quickly by) 10 µM rolipram or 1 µM RS25344, as appropriate:
      a. spots appear clone cells from stables
      b. No spots: see (6)

Example 4

Probes for Proteins X and Y with PKAcatα Anchor protein

Figure 5:
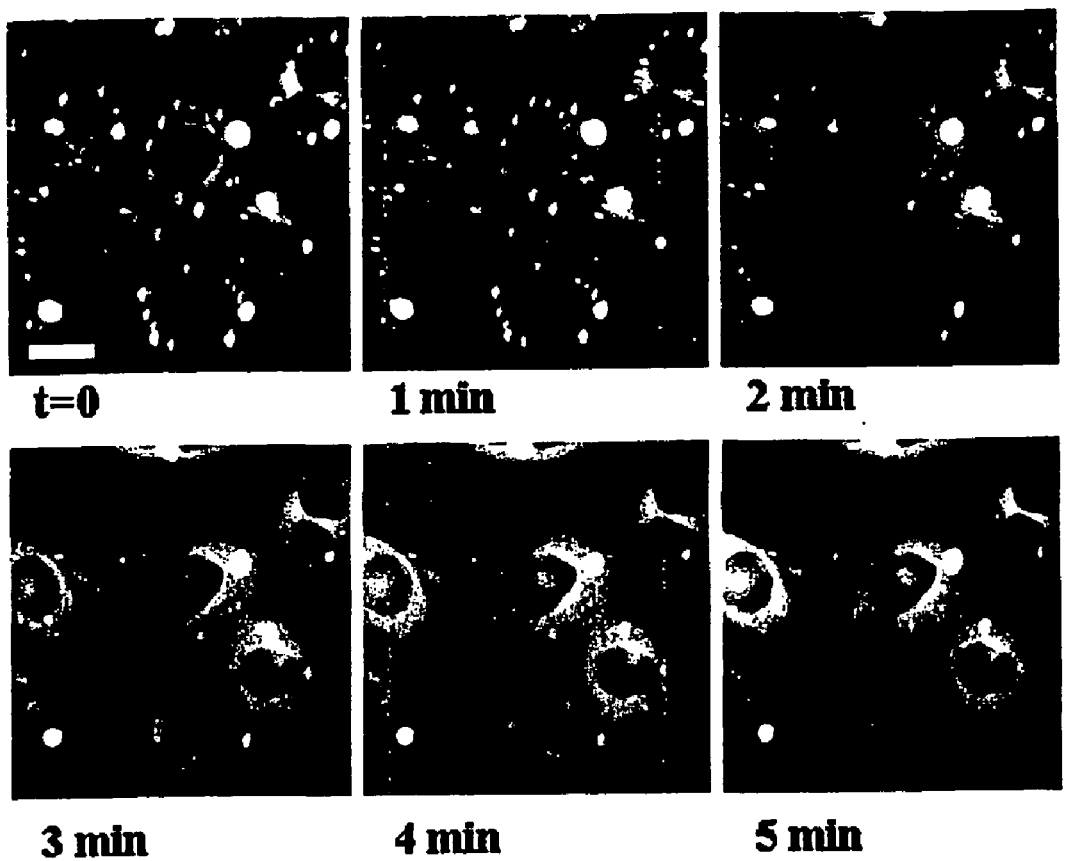

In this example the anchor probes are based on HSPKA-catα (catalytic subunit of human cyclic AMP-dependant protein kinase, isoform α: hereafter referred to as PKAc), which when transfected into cells forms aggregates in the cytoplasm under conditions of low cytoplasmic cAMP concentrations. These aggregates may be detected with an antibody directed against PKAc, also with antibodies directed against the PKA regulatory subunit type 1α (R1α). In cells successfully transfected with a plasmid coding for a fusion protein having GFP fused to the C-terminal of PKAc, such aggregates are seen as bright green fluorescent spots in the cell (FIG. 5). These aggregates disperse into the cytoplasm when cAMP is elevated in the cell, for example when cells are treated with 25 µM forskolin plus 500 µM isobutyl methyl xanthine (IBMX). In cells co-transfected with PKAc anchor probe plus EGFP detectable (X on one, Y on the other), GFP-bright spots will only appear in cells if X and Y interact and attract each other (FIG. 11*a*). The spots will disappear when cAMP is elevated in the cells (FIG. 11*b*).

Protocol for PKAc Anchor System:
1) Co-transfect an anchor-detectable pair into CHO
2) Check distribution in transients
   a) spots present: clone cells from transients and put under double selection (as in 3). Cells ready for screening when stable.
   b) no spots: wait for stables (3)
   c) If other distribution present, distinct from normal PKA spots, test with 50 µM forskolin+500 µM IBMX.
      i) if distribution changes, clone cells ready for use in screening under double selection as described in (3).
      ii) No change: may still be worth continuing to stables at (3)
3) Make stable cell line using double selection (e.g. 1 mg/ml of zeocin plus 0.5 mg/ml neomycin/G418).
   a) spots appear: test with 50 µM forskolin+500 µM IBMX; if distribution changes, clone cells under double selection ready for use in screening.
   b) no spots: fix and stain with anti-PKAcat antibody
      i) spots stain with PKAcat antibody: go to (4)
      ii) no spots: anchor system not present or not working, or cAMP too high stain with antibody to PKA regulatory subunit type 1α (R1α)—this will reveal PKA "spots" even if catalytic subunit detached (high cAMP): if no spots seen, retransfect.
4) Test for conditional association (see A and B below).
5) If no association conditions are found, choose another combination of anchor/detectable pairs and start again.

Test for conditional association with an appropriate interaction stimulus: A and B can be done in parallel. B tests for possible conditions or associations that can only occur in the "soluble phase".

A i) test with an interaction stimulus, i.e. a treatment likely to bring pair together. NB this may need time-lapse to catch transients:
  (a) spots appear: clone cells ready for use in screening.
  (b) No spots: try (B)
B i) incubate stables with 50 μM forskolin+500 μM IBMX for 30 minutes (to allow PKA anchor to be liberated)
  ii) washout forskolin+IBMX, test with an interaction stimulus, i.e. a treatment likely to bring pair together, incubate for 30 to 60 minutes:
    (a) spots appear: clone cells ready for use in screening.
    (b) No spots: see (5).

Example 5

Probes for Proteins X and Y with PDE4A1 Domain Anchor Protein

In this example the anchor probes are based on PDE4A1 domains. PDE4A1 accumulates as small perinuclear spots in otherwise untreated cells. These spots are readily detected wioth an antibody raised against the unique C-terminal portion of PDE4A. Treatment with rolipram causes these spots to disperse into the cytoplasm (FIG. 13). Subsequent removal of rolipram results in the rapid re-appearance of perinuclear spots.

In FIG. 13a CHO cells stably expressing HSPDE4A1-GFP are growing in only HAM's F12 medium with 10% FBS; the GFP fluorescence is restricted to bright granule-like spots within the perinuclear cytoplasm of each cell. The spots may be clustered around, in or on the Golgi membranes. In FIG. 13b similar cells to those seen in 13a have been treated with 2 micromolar rolipram for 2 hours. The majority of GFP-bright spots disappear in all cells under rolipram treatment, and the cytoplasm becomes generally brighter. Larger spots may not disperse completely in some cells. When rolipram is washed away, the spots reform within 1.75 hours.

Furthermore, the distribution of PDE4A1, and any change thereof, is readily measurable by automated imaging.

Figure 14:
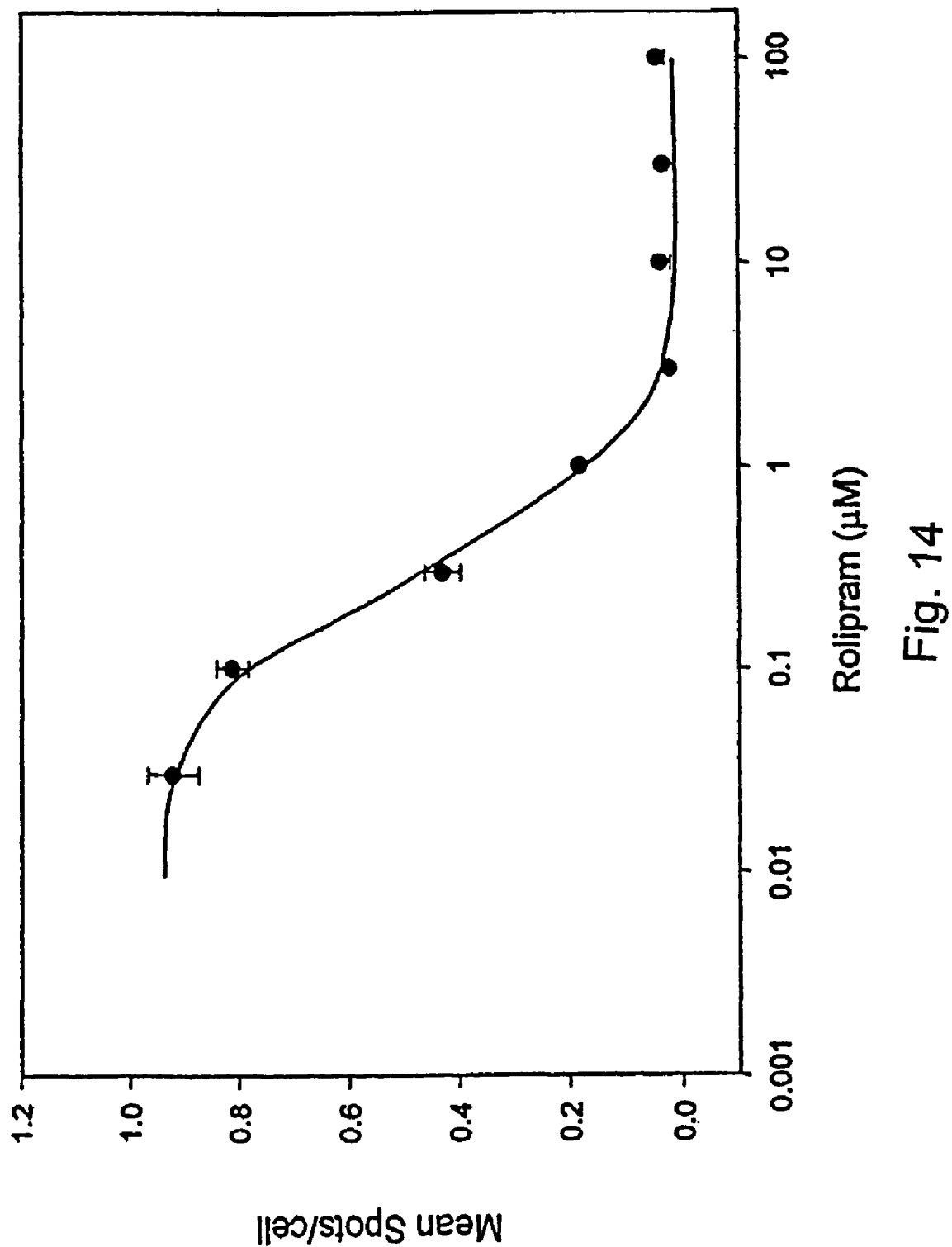

FIG. 14 shows a dose response curve for spot dispersal in response to rolipram. The number of spots per cell for each concentration of rolipram is the mean of 4 measurements±sem, where each measurement is itself an average taken from not less than 100 cells. Cells are grown in HAM's F12 medium plus 10% FBS plus various concentrations of rolipram for 7 hours. The cells are then chemically fixed with 4% formalin buffer (pH7.5) for 15 minutes, washed with PBS and stained with 10 PM Hoechst 33258 in PBS for 10 minutes at 25° C., then washed twice in PBS. Automated images are collected and analysed for the number of spots per cell as described in Example 2.

Protocol for PDE4A1 Anchor System:
1) Co-transfect an anchor-detectable pair into CHO
2) Check distribution in transients
  a) spots present: clone cells from transients and put under double selection (as in 3).
    Cells ready for screening when stable.
  b) no spots: wait for stables (3)
  c) If other distribution present, distinct from normal PDE4A1 spots, test with 10 μM rolipram.
    i) if distribution changes, clone cells ready for use in screening under double selection as described in (3).
    ii) No change: may still be worth continuing to stables at (3)
3) Make stable cell line using double selection (e.g. 1 mg/ml of zeocin plus 0.5 mg/ml neomycin/G418).
  a) spots appear test with 10 μM rolipram; if distribution changes, clone cells under double selection ready for use in screening.
  b) no spots: fix and stain with anti-PDE4A antibody
    i) spots stain with PDE4A antibody: go to (4)
    ii) no spots: anchor system not present or not working; retransfect.
4) Test for conditional association (see A and B below).
5) If no association conditions are found, choose another combination of anchor/detectable pairs and start again.

Test for conditional association with an appropriate interaction stimulus: A and B can be done in parallel. B tests for possible conditions or associations that can only occur in the "soluble phase".

A ii) test with an interaction stimulus, i.e. a treatment likely to bring pair together. NB this may need time-lapse to catch transients:
  (c) spots appear clone cells ready for use in screening.
  (d) No spots: try (B)
B i) incubate stables with 10 μM rolipram for 7 hours (to allow PDE4A1 anchor to be liberated)
  ii) washout rolipram, test with an interaction stimulus, i.e. a treatment likely to bring pair together, incubate for 2 to 4 hours:
    (c) spots appear: clone cells ready for use in screening.
    (d) No spots: see (5).

Example 6

Probes for Proteins X and Y with Cys1 Domain Anchor Protein

Figure 6:
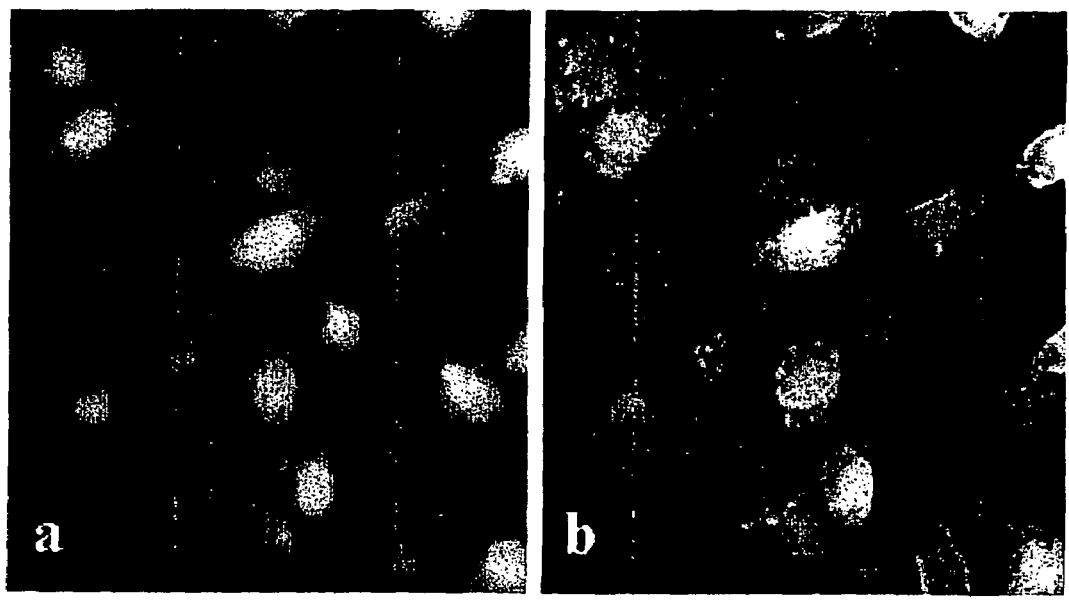
Figure 12:
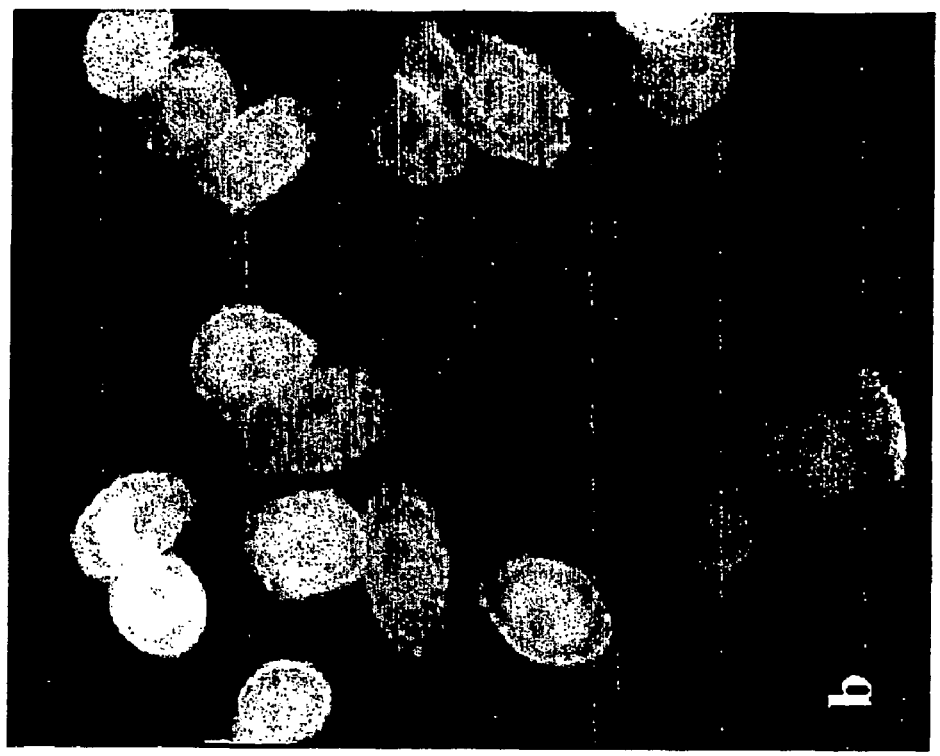
Figure 12:
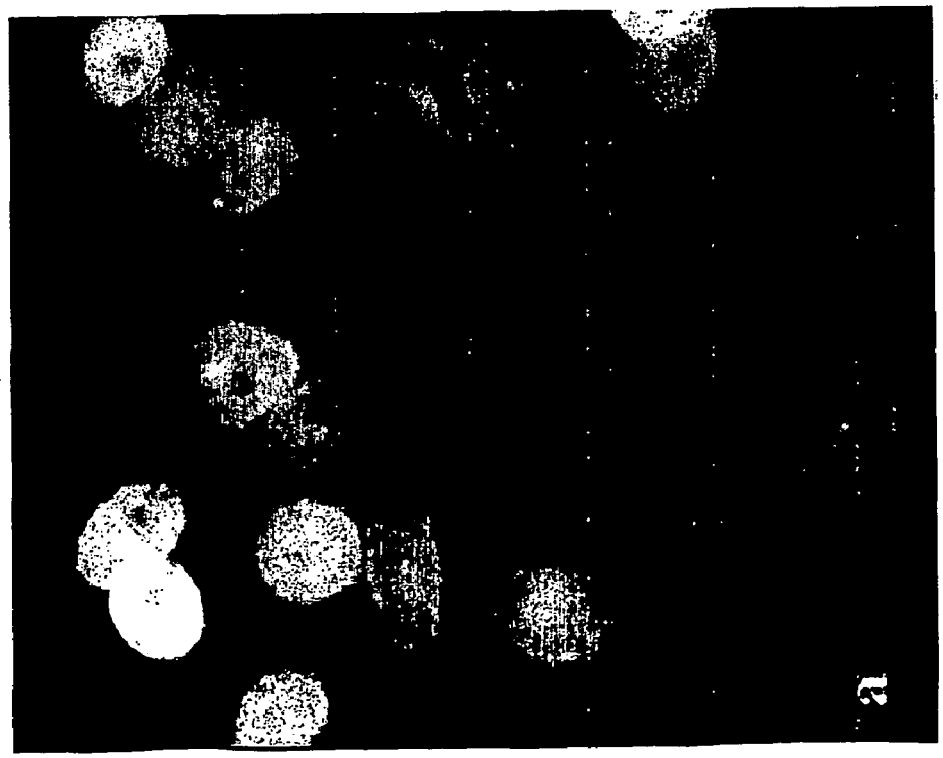

In this example the anchor probes are based on the Cys1 domain of PKCγ (Cys1 domain of protein kinase C isoform γ) in which coding sequences for the myc or flag antigens are optionally included, which when transfected into cells has a general cytoplasmic distribution that redistributes to the plasma membrane when treated with PMA (phorbol-12-myristate-13-acetate). The redistribution from cytoplasm to plasma membrane may be detected with an antibody directed against the Cys1 domain of PKCγ, or with antibodies directed against the myc or flag antigens, if these have been engineered into the Cys1 construct. In cells successfully transfected with a plasmid coding for a fusion protein having GFP fused to the C-terminal of the Cys1 domain of PKCγ, with or without the myc or flag antigen sequences, the PMA-induced redistribution is observable as a decrease in GFP fluorescence in the cytoplasm with a concomitant increase in GFP fluorescence at the plasma membrane (FIG. 6). In cells co-transfected with Cys1 domain of PKCγ anchor probe plus EGFP detectable probe (X on one, Y on the other), GFP fluorescence will only redistribute to the plasma membrane upon PMA treatment if X and Y interact and attract each other (FIG. 12).

Cys1 Anchor.
1) Co-transfect new anchor-detectable pair into CHO
2) Check that distribution is cytoplasmic in transients. If spots, or other distinct distribution present, may still be worth testing at (3), but only if a change in distribution is be measurable.
3) Test transients with 100 nM PMA for 30 minutes
   a) Probe redistributes to plasma membrane: clone cells from transients under double selection as in (4)
   b) no redistribution: wait for stables (see 4)
4) Make stable cell line using double selection (e.g. 1 mg/ml of zeocin plus 0.5 mg/ml neomycin/G418). Test with PMA
   a) Probe redistributes to plasma membrane: under double selection ready for use in screening.
   b) no redistribution: fix and stain with anti-myc antibody
      i) PM stains with antibody: go to (5)
      ii) no PM stain: anchor system not present or not working—retransfect.
5) Test for conditional association (see A and B below).
6) If no association conditions are found, choose another combination of anchor/detectable pairs and start again.

Test for conditional association with an appropriate interaction stimulus: A and B can be done in parallel. B tests for possible conditions or associations that can only occur in the "soluble phase", before targeting to PM is imposed.
A i) incubate stables with 100 nM PMA for 30 minutes
   ii) test with an interaction stimulus, i.e. a treatment likely to bring pair together. NB this may need time-lapse to catch transients:
      (a) redistribution to PM occurs: clone cells from stables etc.
      (b) No redistribution: try (B)
B i) test with an interaction stimulus, i.e. a treatment likely to bring pair together, together with (or followed quickly by) 100 nM PMA
      (a) redistribution to PM occurs: clone cells from stables under double selection as in (4)
      (b) No redistribution: see (6)

Example 7

Assessment of Sos and Grb2 Interactions with PDE4A4

Figure 9:
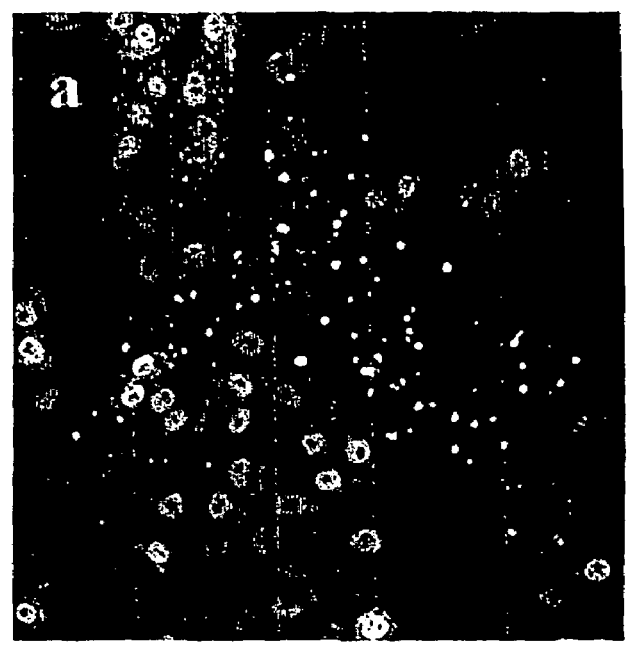
Figure 9:
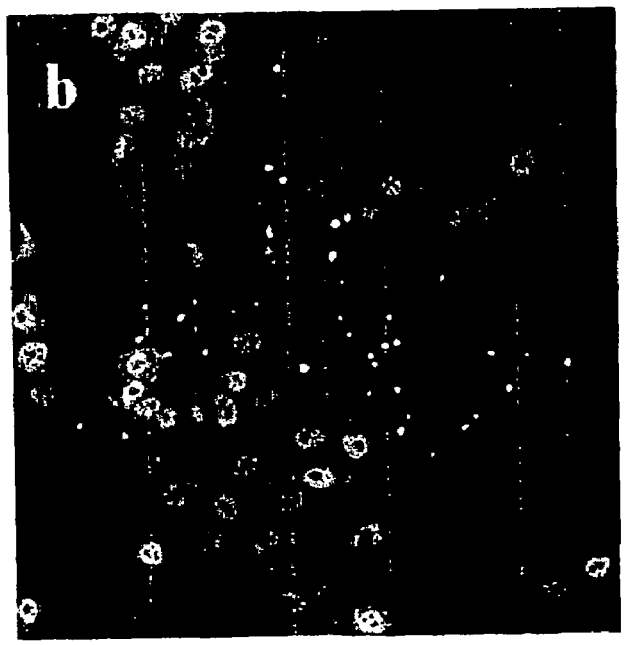
Figure 10:
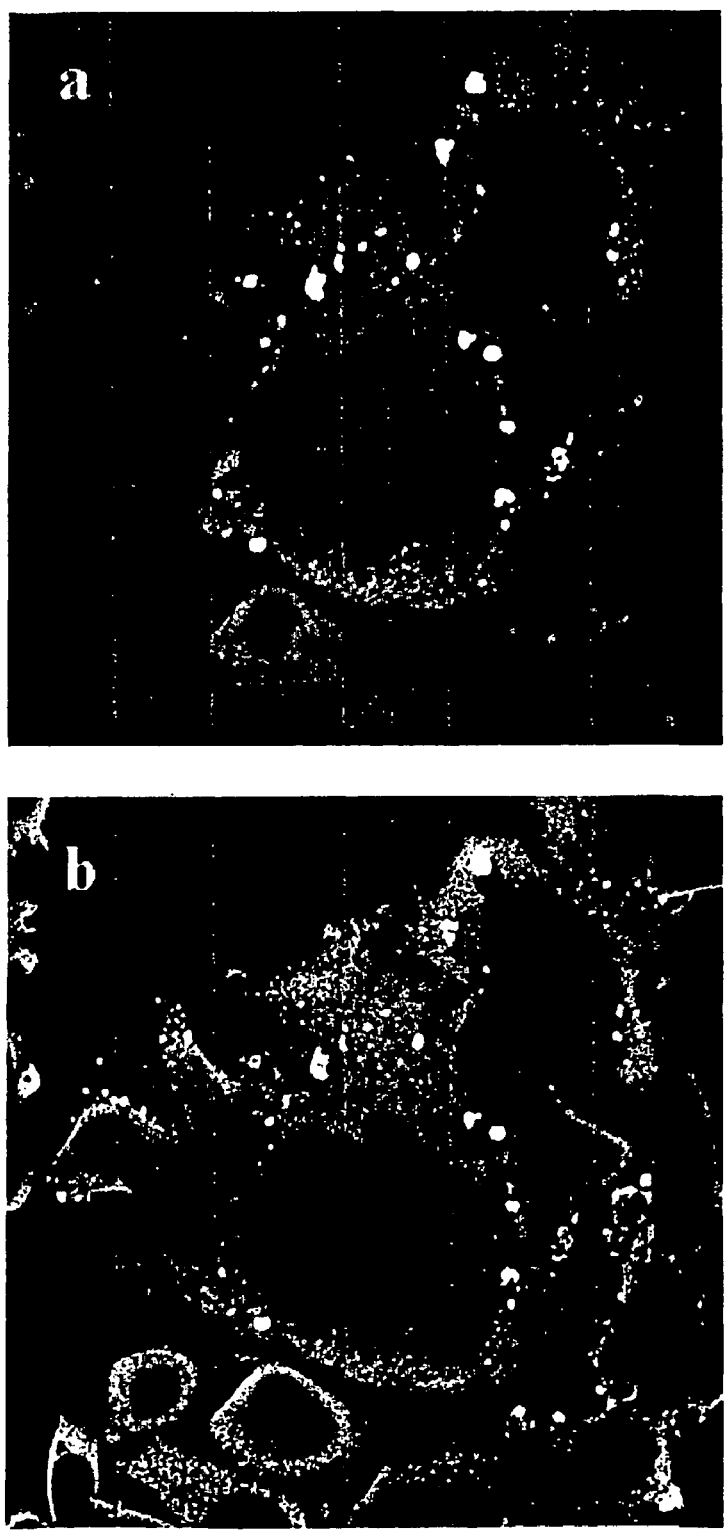

This example demonstrates the use of the redistribution trap method to create a cell line suitable for screening compounds against the interaction between Sos and Grb2, components involved in the signalling pathway immediately downstream from certain tyrosine kinase receptors located at the plasma membrane of mammalian cells, for example the insulin and the epidermal growth factor receptors. Sos is a guanine nucleotide exchange factor responsible for activation Ras-like GTPases, Grb2 an adaptor component responsible for recuiting Sos to the activated receptor. In this example the anchor probe is based on HSPDE4A4. CHO cells are stably co-transfected with anchor probe HSPDE4A4-SosA and "detectable" probe hGrb2-EGFP as described in Example 2 and Example 3. The anchor probe is selected for with zeocin, and the detectable probe with neomycin (G418). FIG. 8a is a confocal image of such cells growing in HAM's F12 medium with 10% FBS and FIG. 8b shows similar cells after treatment with 10 μM rolipram. The transfected cells are a mixed non-clonal population. The GFP-labelled detectable probe (GFP fluorescence) is distributed throughout the cell prior to rolipram treatment, with a slightly higher concentration in the nuclei. After rolipram treatment (20 hours) some cells, in clonal groups, develop distinct bright spots (FIG. 8b). The appearance of the spots, and the requirement for rolipram, indicate that in these cells the anchor probe has responded to rolipram as PDE4A4 is expected to (FIG. 2), and that the GFP-labelled detectable probe must be associated with it. To confirm that the spots are the result of a rolipram induced effect on the anchor probe, the PDE4 specific inhibitor RP73401 is applied in the presence of rolipram (FIG. 9). RP73401 competes with rolipram and causes PDE4A4 spots to disperse (FIG. 3 and 4). As can be seen in FIG. 9, the spots disappear with RP73401 treatment, confirming that it is the anchor probe that is responsible for the spotty distribution of the detectable probe, and thus that anchor and detectable pairs are interacting. Since HSPDE4A4 and EGFP do not interact when co-transfected and rolipram treated (not shown, but EGFP distribution is always pan-cellular, in both nucleus and cytoplasm in such cells, and its distribution is unaffected by rolipram), the interaction must be mediated by the natural interaction of Sos and Grb2.

When cloned, the co-transfected cells may be used for screening compounds against the Sos-Grb2 interaction. Compounds, which make the rolipram-induced spots, disappear in these co-transfected cells, but which do not affect rolipram-induced spots in cells stably expressing only the HSPDE4A4-EGFP probe, are compounds, which specifically disrupt the interaction between Sos and Grb2.

Example 8

Assessment of Sos and Grb2 Interactions with PKAcatα

This example describes the creation of a cell line suitable for screening compounds against the interaction between Grb2 and the C-terminal sequence of Sos (amino acids 1067 to 1332 of Sos). This is similar to the interaction pair described in Example 7, except that the anchor probe is based upon the catalytic subunit of cAMP-dependent protein kinase isoform α (HSPKAcat-hGrb2), and therefore locates in unstimulated cells as aggregates, which if they attract the detectable probe (EGFP-Sos-Cterm) will become GFP-bright. One potential advantage of this anchor system is that a prior anchor stimulus is not needed in order to appreciate an interaction, but is used as a confirmatory test after the interaction has been identified. The process of screening for interaction modulators with this system therefore involves no likelihood of changing the activity of other cellular signaling pathways which may interfere with the interaction under test.

Treatment with forskolin±IBMX (isobutyl methylxanthine, a non-specific PDE inhibitor) is used in the PKAcat system to confirm that any GFP-bright aggregates are the result of a specific interaction between anchor and detectable probes in this system, since aggregates of PKAcat will dissolve into the cytoplasm under this treatment.

Figure 11:
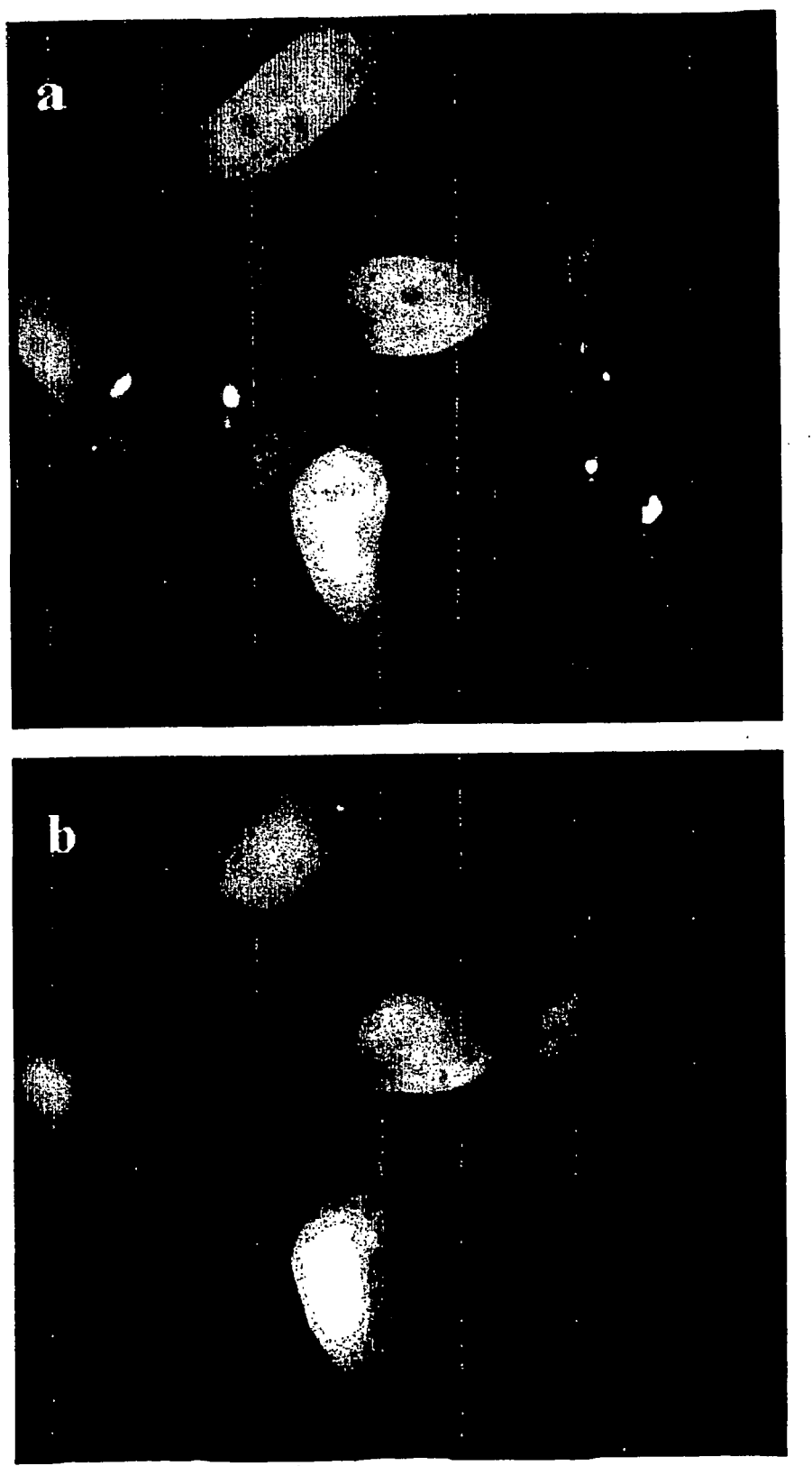

CHO cells are stably co-transfected with the anchor probe HSPKAcat-hGrb2 and GFP-labelled detectable probe EGFP-Sos-Cterm as described in Example 2 and Example 4. The anchor probe is selected for with zeocin, and the detectable probe with neomycin (G418). CHO cells stably expressing both the anchor probe HSPKAcat-hGrb2 and GFP-labelled detectable probe EGFP-Sos-Cterm are shown in FIG. 11 before (FIG. 11a) and 10 minutes after (FIG. 11b) treatment with 50 micromolar forskolin+500 micromolar IBMX. Three cells are evident in (FIG. 11a) with GFP-bright aggregates typical of the distribution of PKAcat- EGFP seen in unstimulated cells (FIG. 5, t=0 minutes). The dispersal of these spots by forskolin+IBMX, a treatment which increases cAMP in the cells, shows that the GFP-labelled detectable probe must be interacting with the anchor probe in the co-transfected cells, because only the anchor probe can react to increased cAMP in this way (FIG. 5).

Cells showing spots are suitable for cloning and may then be used for screening compounds against the interaction between Grb2 and Sos-Cterm. Compounds which make the GFP-bright aggregates disappear in these co-transfected cells, but which do not affect aggregates in cells stably transfected with PKAcat-EGFP probe alone, are compounds which specifically disrupt the interaction between Sos-Ctern and Grb2.

Example 9

Assessment of Sos and Grb2 Interactions with Cys 1 Domain

This example describes the creation of another cell line suitable for screening compounds against the interaction between Grb2 and the C-terminal sequence of Sos (amino acids 1067 to 1332 of Sos). This is the same interaction pair described in Example 6, except that the anchor probe is based upon the Cys1 domain of protein kinase C isoform gamma, and therefore locates in unstimulated cells throughout the cytoplasm and nucleus. When these cells are treated with 100 nM PMA the anchor probe redistributes to the plasma membrane, and if an interaction occurs between anchor and detectable probes, the GFP fluorescence will also be seen to redistribute to the plasma membrane. An advantage of this anchor system is that when stimulated with PMA, the anchor probe is taken to the plasma membrane where it will come into close proximity with other components that may be important in modulating the interaction between the components attached to the anchor and EGFP moieties. In the case of Grb2 and Sos-Cterm proximity to the plasma membrane does not appear to be necessary in order to initiate their interaction, but certain component pairs may fail to interact unless this condition is met. Treatment with PMA is used to confirm that an interaction between anchor and detectable probes occurs in this system, since redistribution of fluorescence to the plasma membrane can only occur if interaction of the two probes has first taken place. This can be checked in CHO cells transfected with EGFP-Sos-Cterm alone, where PMA has no effect on the distribution of fluorescence.

CHO cells are stably co-transfected with the anchor probe Cys1-hGrb2 and the GFP-labelled detectable probe EGFP-Sos-Cterm as described in Example 2 and Example 6. The anchor probe is selected for with zeocin, and the detectable probe with neomycin (G418). FIG. 12 shows CHO cells stably expressing both the anchor probe Cys1-hGrb2 and GFP-labelled detectable probe EGFP-Sos-Cterm before (FIG. 12a) and 5 minutes after (FIG. 12b) treatment with 100 nM PMA. The majority of cells in before PMA treatment have a rather general cytoplasmic and nuclear distribution of fluorescence. Treatment with PMA causes a measurable shift in fluorescence to the plasma membrane, in the same way that Cys1-EGFP would redistribute in response to PMA (FIG. 6). This result shows that the GFP-labelled detectable probe must be interacting with the anchor probe, because only the anchor probe can react to PMA in this way.

Cells showing this behaviour are suitable for cloning and may then be used for screening compounds against the interaction between Grb2 and Sos-Cterm. Compounds which prevent PMA-induced redistribution of EGFP fluorescence in these co-transfected cells, but which do not affect fluorescence redistribution in cells stably transfected with the Cys1-EGFP probe alone, are compounds, which specifically disrupt the interaction between Sos-Cterm and Grb2.

Example 10

Assay Procedure for Trap Assay

The selective PDE4 inhibitor rolipram affects the physical properties and behaviour of PDE4A4 such that the general cytoplasmic distribution of PDE4A4 in most cells gradually changes to one consisting of concentrations of PDE4A4 located at several distinct spots within the cytoplasm (see Example 3).

This example illustrates how binding between the 14-3-3 protein and BAD can be visualized using the PDE4A4-14-3-3beta and eGFP-BAD fusions. It is an example of a change in mobility from a soluble cytoplasmic state to a state wherein the eGFP-BAD fusion is attached, or actually aggregated in the cytoplasm.

Chemicals used:
NUT.MIX F-12(HAM) with GLUTAMAX-1. Gibco Brl 31765-027.
"FCS", Foetal Bovine Serum, Gibco Brl 10084-168.
Pen/strep (100 u/ml/100 µg/ml, Gibco cat Brl 15140-122)
Formaldehyde 4%. Bie & Berntsen Lab 00220.
Triton-x 100, Sigma
Hoechst 33258 (stock solution: 10 mM)
rolipram, RBI
DMSO, Sigma D-5879.

Instrumentation:
Fluoscan ASCENT CF plate reader (Labsystems)
Filters: 485/527 (GFP) and 355/460 (Hoechst) all from Labsystems
Buffers:
Extraction buffer: Formaldehyde 4% diluted 1:40 (=0.1%) in PBS+Triton-x 100 1%+Hoechst33258 10 µM.
PBS Dulbecco's: GIBCO 14190-094
Cells:
Cell type: CHO cells transfected with one plasmid expressing an in frame protein fusion between PDE4A4 and human 14-3-3beta and another plasmid expressing an in frame protein fusion between EGFP and human BAD (details on the construction of such probes can be found in examples 1 and 3).
Density: 1.0×10E5/well (the day they are seeded), in 96-well microtitre plates (ViewPlate-96, Black; Packard)
Procedure:
Cells are plated in 1.0×10E5/well in 200 µl HAM F-12 w. 10% FCS and 5% pen/strep 20-24 hrs before screening. Stimulated cells are further added 10 µM rolipram. For testing drugs capable of inhibiting the interaction between 14-3-3 and BAD the test compound is added on top of the 200 µl HAM F-12 growth medium and incubated for 2 hrs in $CO_2$ incubator HAM F-12 with test compound is drained from all wells of the microtitre plate and cells are extracted in 200 µl extraction buffer for 5 min.

Cells are added 100 µl formaldehyde 4% buffer on top of the 200 µl extraction buffer and are incubate for 5 min.

Extraction buffer is drained and cells are washed×2 in 100 µl PBS. Cells are added 200 µl PBS buffer.

Figure 15:
Figure 15:
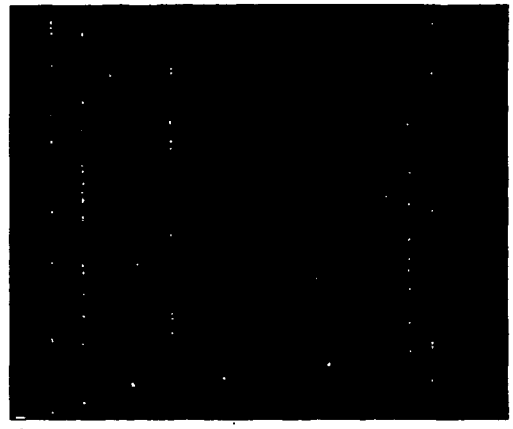
Figure 15:
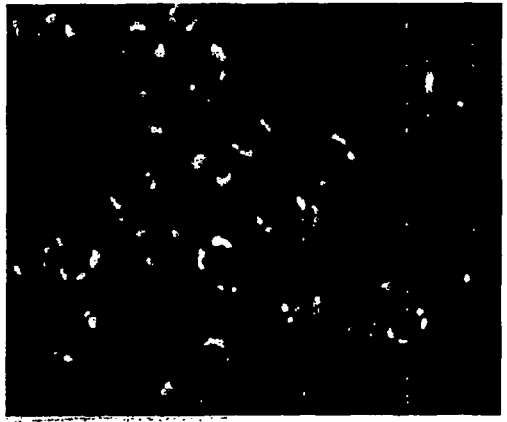
Figure 15:

The fluorescence is read in ASCENT plate reader using a pre-programmed procedure and filter settings suitable for GFP and Hoechst 33258 fluorophores. The Hoechst reading is used to provide a signal by which cell number can be estimated, and thereby useful in normalising GFP signals from wells that may not contain identical number of cells. The results are presented in FIG. 15.

Example 11

Assay Procedure for Redistribution™ Assay

It is well established that NFkB(p65) moves from cytosol to nucleus upon stimulation of NFkB with II-1. This can be visualized with a NFkB(p65)-GFP fusion. The total GFP intensity measured after removing cytosolic NFkB(p65)-YGFP is indicative of the degree of translocation to the nucleus, and thus of the degree of activation of NFkB. This is an example of a change in mobility as a change from a soluble cytoplasmic NFkB to a component attached in the nucleus.

Figure 16:
Figure 16:
Figure 16:
Figure 16:
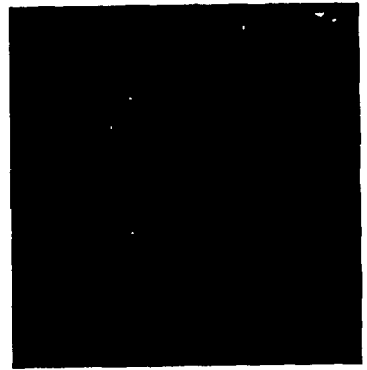

Applying the extraction procedure, the difference between non-stimulated and stimulated cells can be read by the intensity of fluorescence (see FIG. 16).

Example 12

Extraction Optimisation

Cells are seeded in a known concentration and grown for 24 hrs. Stimulated and non-stimulated cells (representing the full "dynamic" range) are extracted with different combinations of triton-x 100 and formalin and the signal is read in a plate reader.

The aim is to identify the ratio between formalin and triton-x that gives the optimal signal to noise (s/n) ratio. The s/n is calculated as (fluorescence in stimulated cells minus the fluorescence in non-stimulated cells) divided by the fluorescence in the non-stimulated cells times 100%.

$$s/n = \frac{(\text{stimulated cell} - \text{non stimulated cells})}{\text{non stimulated cells}} * 100\%$$

Figure 17A:
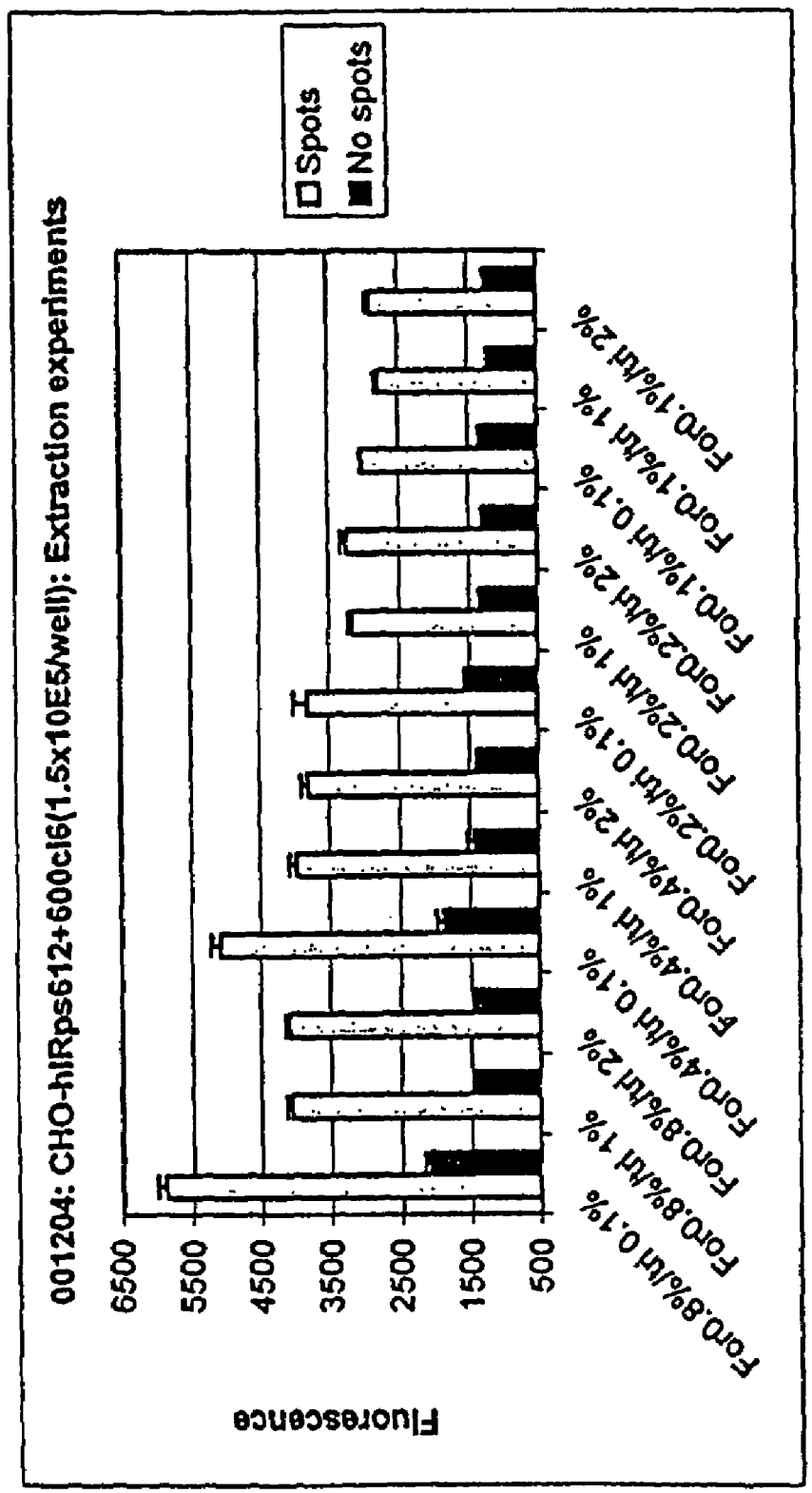
Figure 17B:
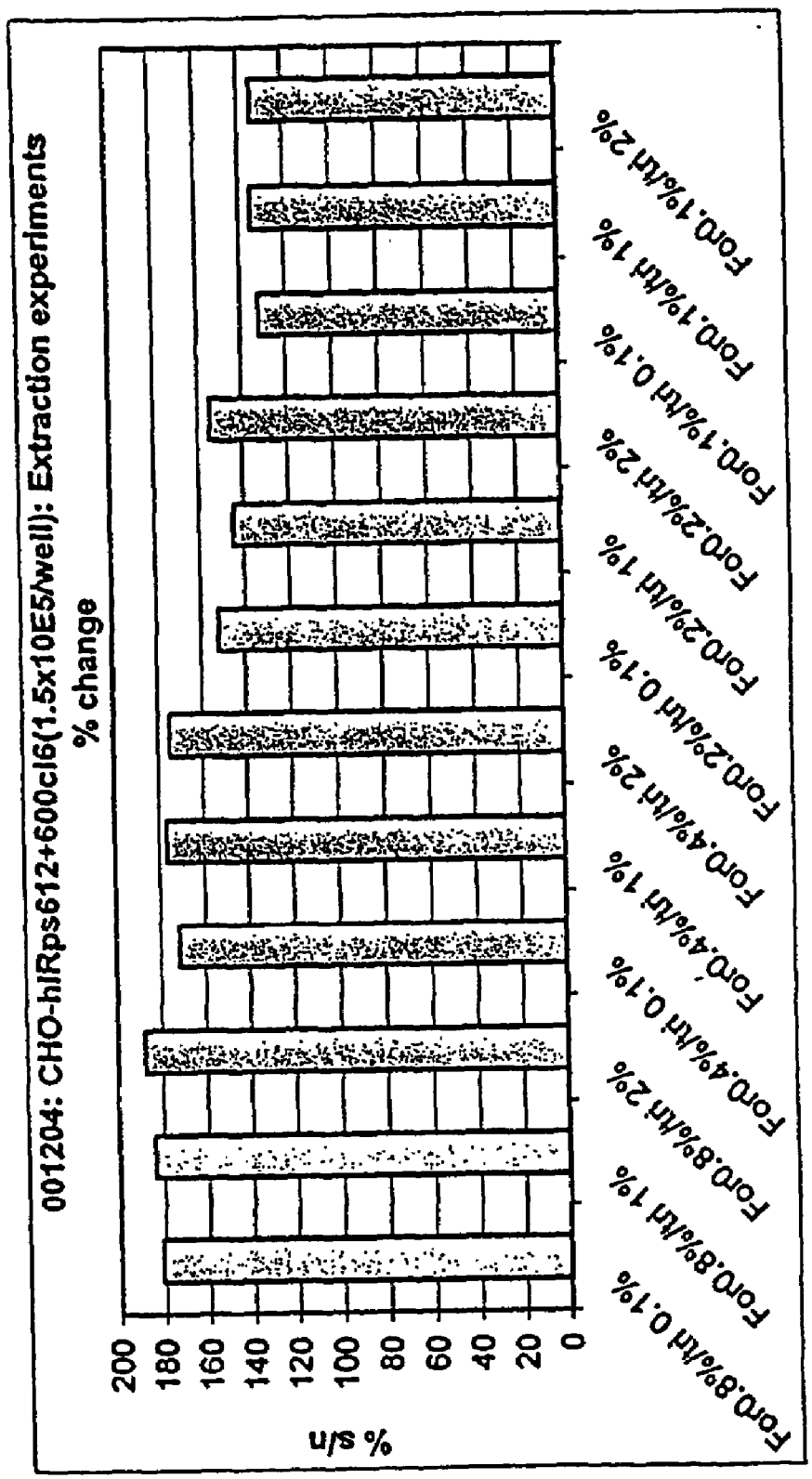

Optimisation of the extraction buffer for binding between the 14-3-3 protein and BAD The optimization is illustrated in FIG. 17.

Example 13

Quantification of Forskolin Induced PKAcat Translocation using Extraction

PKAcat-GFP forms distinct spots in its inactive tetrameric form. Upon increase in cellular cAMP (e.g. by stimulation of adenylate cyclase activity by forskolin) PKAcat dissociates from its regulatory subunits and spots "dissolves" into the cytosol. The total GFP intensity measured after removing cytosolic PKAcat-GFP through the extraction procedure is indicative of the level of non-activated, non-dissociated PKAcat.

In this example the extraction procedure is used to quantify a forskolin dose response in a PKAcat-GFP assay.

Figure 18:
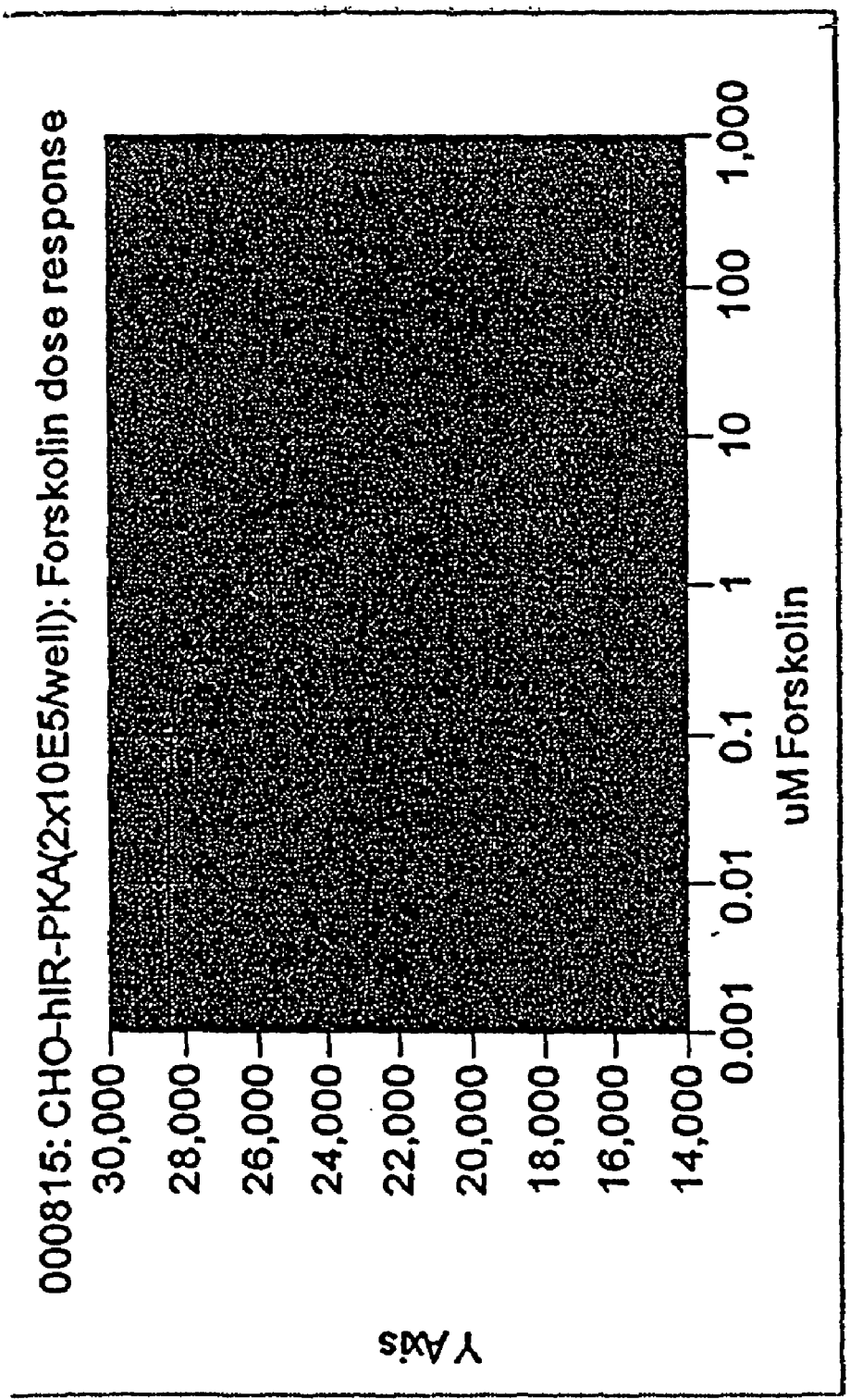

Cells are treated with forskolin in various conc. for 15 min. (remove spots). Cells are extracted (Formalin 0.2%/Triton-x 0.2%). Signal is read in FLIPR. Results presented in FIG. 18. The determined ED50 at about 3 µM is in accordance with literature standards.

Example 14

Comparison of the Effect of Rolipram Treatment upon Normal CHO Cells and upon CHO Cells Stably Expressing a HSPDE4A4B-GFP Fusion Protein The PDE4 inhibitor rolipram is used to stimulate the production of the dense aggregates 5 of PDE4A4 in the cytoplasm of cells transfected with fusions to PDE4A4 described in Example 3. A possible concern of using such a stimulus is that levels of the second messenger molecule cAMP, the substrate for PDE4 enzymes, may increase in rolipram treated cells to such an extent that unwanted cAMP-dependent processes in those cells may also become activated. Examples of cAMP-dependent effector proteins include the PKA family of kinases, some ion channels and certain guanine nucleotide exchange factors such as cAMP-GEF1 and 2. This example demonstrates that treatment with rolipram does not by itself increase cellular cAMP levels in CHO cells expressing HSPDE4A4B-GFP, although this fusion protein has phophodiesterase activity. Unwanted activation of cAMP-dependent processes in these cells is therefore highly unlikely when rolipram is used to stimulate the production of the dense aggregates of PDE4A4 in these cells.

CHO cells stably expressing HSPDE4A4B-GFP (see Example 2), and untransfected CHO cells are seeded into individual wells of a 96-well microtiter plate at a density of $1.2 \times 10^5$ cells/well, and cultured for 16 to 18 hours in HAM F-12 medium with glutamax, 100 µg penicillin-streptomycin mixture ml$^{-1}$ and 10% FBS plus various concentrations of rolipram. After the incubation period, cAMP content is measured using a commercial kit from Amersham-Pharmacia Biotech, kit # RPA538, according to the manufacturers instructions.

Figure 19:
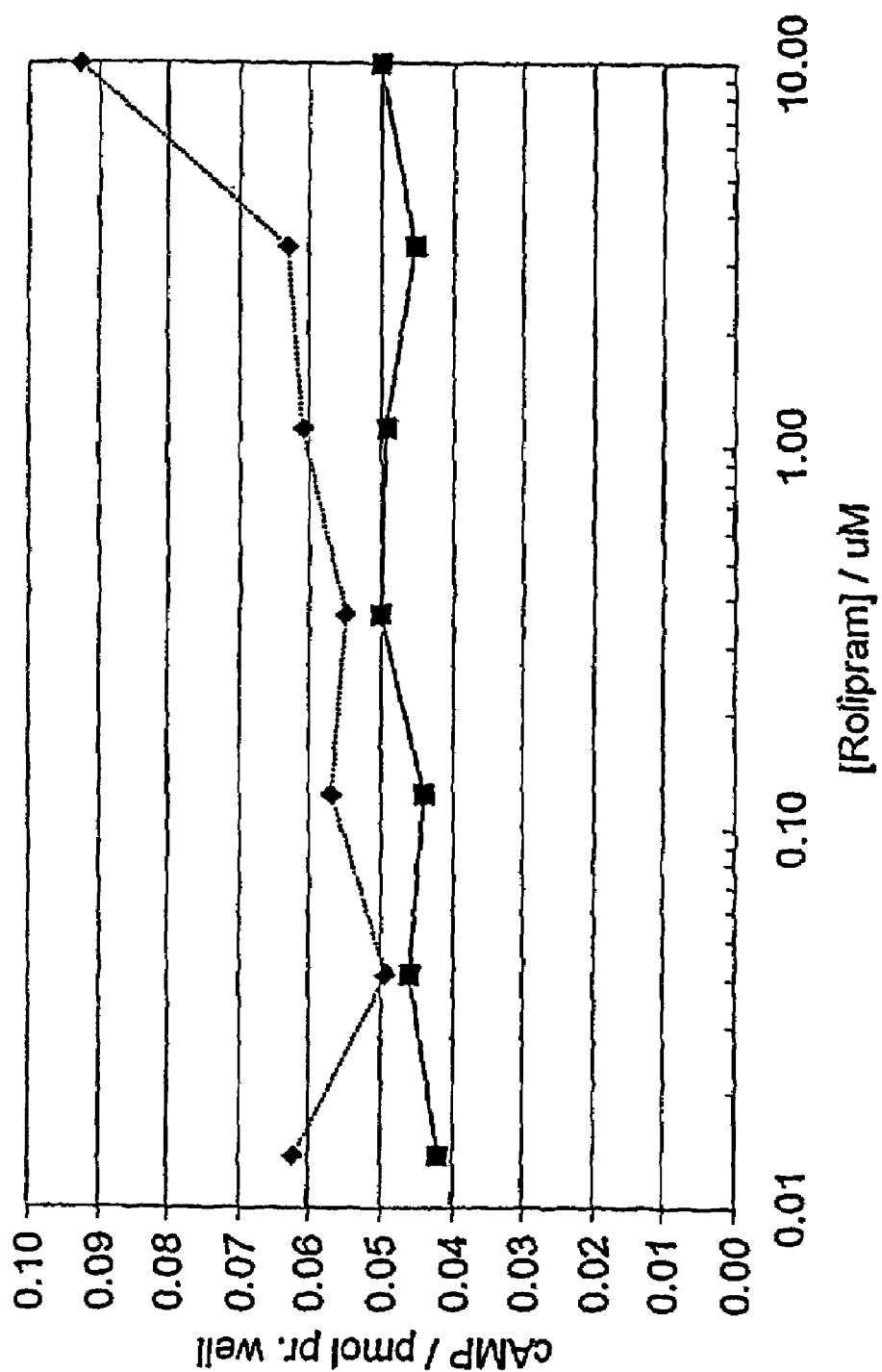

The amount of cAMP/well was calculated using regression analysis from a cAMP standrad curve, as recommended by the manufacturers of the assay kit. The results of this experiment are shown in FIG. 19. The curves for both normal untransfected CHO cells (♦), and cells stably expressing HSPDE4A4B-GFP (□) show no appreciable increase in cellular cAMP concentration over a range of rolipram treatments from 0.03 µM to 3 µM. The slight rise in cAMP in normal CHO cells at 10 µM rolipram is probably not significant, since this concentration is between 30 to 300 fold higher than any reported IC$_{50}$ value for inhibition of any known isoform of PDE4 by rolipram.

Figure 20:
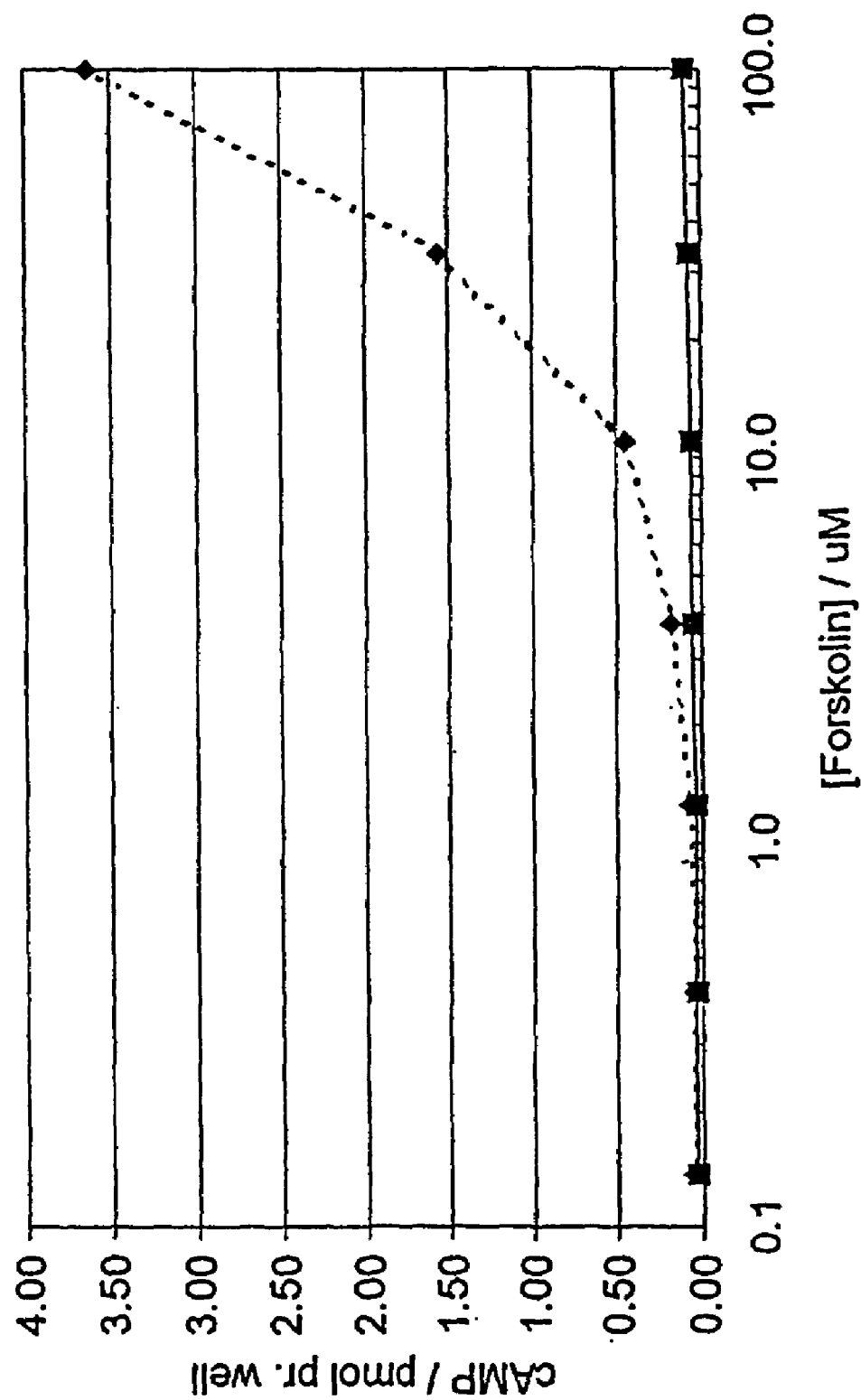

In a separate experiment, untransfected CHO cells and CHO cells stably expressing HSPDE4A4B-GFP were cultured as described for FIG. 19 without the addition of rolipram, but with various concentrations of forskolin added 60 minutes prior to measurement of cAMP levels. The results of this experiment are shown in FIG. 20. The curve for normal untransfected CHO cells (♦) shows the expected dose-dependent increase of cellular cAMP in response to this adenylate cyclase activator. Cells stably expressing HSPDE4A4B-GFP (□) show no appreciable increase in cellular cAMP concentration over a range of forskolin treatments from 0.3 µM to 100 µM. This result indicates that the HSPDE4A4-GFP fusion protein is an active phosphodiesterase enzyme and that its greatly increased expression effectively prevents any cAMP increase in these cells despite adenylate cyclase activation by forskolin over the range tested.

Figure Legends

FIG. 1

Confocal fluorescence image showing CHO cells stably transfected with probe HSPDE4A4-EGFP-N1 growing in HAM's F12 medium with 10% FBS. The transfected cells are clonal, derived from a mixed, non-clonal population. GFP fluorescence is more or less evenly distributed throughout the non-nuclear cytoplasm, darker regions within this area are probably mitochondria from which the probe is apparently excluded.

FIG. 2

Confocal fluorescence image showing CHO cells stably transfected with probe HSPDE4A4-EGFP-N1 growing in HAM's F12 medium with 10% FBS and with 2 μM rolipram. The transfected cells have been derived from a single cell isolated from a non-clonal population. The cells have been treated with rolipram for 6.7 hours. GFP fluorescence concentrates in bright spots in more than 95% of the cells.

FIG. 3

Dose response of RP73401 versus 3 μM rolipram in clonal cells expressing HSPDE4A4-EGFP. Cells have been seeded into a 96-well Packard ViewPlate and grown in HAM's F12 medium plus 10% FBS plus 3 μM rolipram to approximately 80% confluence. rolipram treatment was for a total of 16 hours. Various concentrations of RP73401 were added to the rolipram-containing wells and incubated for a further 4 hours. The cell were then chemically fixed, washed and stained with Hoechst 33258, and a measurement of mean spots per cell made for each treatment well using an automated imager, all as described in Example 2. Each point is the average of the mean spots per cell determined from 5 individual treatment wells at the same RP73401 concentration. Results have been fitted to a 4-parameter Hill plot, and yield an $IC_{50}$ figure of 20 nM for the competitive inhibition by RP73401 of spot formation by 3 μM rolipram.

FIG. 4

Dose response of RP73401 versus 1 μM rolipram in clonal cells expressing HSPDE4A4-EGFP, measured on the FLIPR. Cells have been seeded into a 96-well Packard ViewPlate and grown in HAM's F12 medium plus 10% FBS plus 1 μM rolipram to approximately 80% confluence. rolipram treatment was for a total of 16 hours. Various concentrations of RP73401 were added to the rolipram-containing wells and incubated for a further 4 hours. The cells were then simultaneously chemically fixed and permeabilised, washed and a measure of spot formation made on a FLIPR device, all as described in Example 2. The degree of spot formation (ordinate values) is given as raw values, which include the background signal (value from cells with no rolipram treatment)±standard deviation.

Results have been fitted to a 4-parameter Hill plot, and yield an $IC_{50}$ figure of approximately 50 nM for the competitive inhibition by RP73401 of spot formation by 1 μM rolipram.

FIG. 5

Time-lapse images of CHO cells expressing HSPKAcat-EGFP, the fusion of EGFP to the C-terminal of human cAMP-dependent protein kinase catalytic subunit isoform alpha, treated with forskolin. Cells are a clonal cell line growing in HAM's F12 medium plus 10% FBS to which has been added I micromolar forskolin at time t=0. Successive images show how the fluorescently tagged catalytic subunit of PKA redistributes from the bright aggregates into the cytoplasm over a period of minutes as cAMP levels increase in the cells as a result of forskolin treatment. Scale bar=10 microns.

FIG. 6

Time-lapse images of CHO cells expressing Cys1-EGFP, the fusion of EGFP to the C-terminal of the cys1 domain from human protein kinase C isoform gamma, before (a) and after 5 minutes treatment with 100 nM PMA. Cells are a clonal cell line growing in HAM's F12 medium plus 10% FBS. After 5 minutes treatment with 100 nM PMA (b), the fluorescently tagged Cys1 domain of PKCgamma redistributes from the cytoplasm and nucleus to the plasma membrane.

FIG. 7

A clonal CHO cell line stably expressing the Cys1 domain of the human isoform of PKC gamma tagged with GFP in its C-terminal end was cultured in 96-well microliter plates (Packard View-Plate). After 20 min preincubation in KRW (experimental buffer; A modified Krebs-Ringer buffer containing (in mM): NaCl 140, KCl 3.6, NaH2PO4 0.5, MgSO4 0.5, NaHCO3 2.0, CaCl2 1.5 and HEPES 10, D-glucose 5 (pH 7.4, btrated with 1M NaOH)) the cell plate was placed in the FLIPR. Subsequently the cells were stimulated in place on the FLIPR machine with the phorbol ester PMA given in doses from 10 μM to 0.5 nM in 1:3 steps. This gives a type of redistribution response in these cells that can be quantified as a reduction in fluorescence intensity, as PKC-gamma-Cys1 moves from the cytosolic and nuclear compartments to the plasma membrane during the first 1-5 minutes of stimulation. The figure shows the dose response as mean (+SD) accumulated fluorescence change during the first three minutes of stimulation with PMA (n=8). All data were corrected for background by subtraction of a background trace based on 8 individual background traces and set to zero at the point of addition of PMA.

FIG. 8

Confocal fluorescence images showing CHO cells stably co-transfected with anchor probe HSPDE4A4-SosA and detectable probe hGrb2-EGFP growing in HAM's F12 medium with 10% FBS plus (a) and similar cells after treatment with 10 μM rolipram (b). The transfected cells are a mixed non-clonal population. The GFP-labelled detectable probe (GFP fluorescence) is distributed throughout the cell prior to rolipram treatment (a), with a slightly higher concentration in the nuclei. After rolipram treatment (20 hours; b) some cells, in clonal groups, develop distinct bright spots. The appearance of the spots, and the requirement for rolipram, indicate that in these cells the anchor probe has responded to rolipram as PDE4A4 is expected to (FIG. 2), and that the GFP-labelled detectable probe must be associated with it.

FIG. 9

The same population of cells as in FIG. 8b, treated for 20 hours with 10 micromolar rolipram (a) are additionally treated with 10 μM RP73401 for 75 minutes at room temperature (b). This treatment dissolves rolipram-induced spots of HSPDE4A4-EGFP (FIGS. 3 and 4), and has the same effect on GFP-bright spots in these cells, confirming that these spots are the result of interaction between the anchor probe and GFP-labelled detectable probe.

FIG. 10

CHO cells expressing HSPDE4A4-EGFP have been treated with 10 μM rolipram for 20 hours then chemically fixed and immunostained with an antibody raised in an ovine host against a peptide identical to a portion of the unique C-terminal sequence of HSPDE4A enzymes. The antibody is detected using Alexa 549-conjugated donkey anti-sheep antibody (Molecular Probes Inc., Oregon, USA). This pair of confocal micrographs show the image of EGFP fluorescence in the cells (a) in comparison to that obtained for Alexa 549 fluorescence (b). Emission filters (a: 515-525 nm bandpass. b: 590 nm long pass) have been chosen to ensure that there is no significant bleed-through of fluorescence between GFP and Alexa 594 images. These images demonstrate how the PDE4A4 antibody can be used to detect aggregates of HSPDE4A4 independently of the need for an EGFP tag, which is useful in confirming the existence of unlabelled HSPDE4A4-based anchor probes in co-transfected cells that have been rolipram treated.

FIG. 11

CHO cells stably expressing both the anchor probe HSP-KAcat-hGrb2 and GFP-labelled detectable probe EGFP-Sos-Cterm before (a) and 10 minutes after (b) treatment with 50 micromolar forskolin+500 micromolar IBMX. Three cells are evident in (a) with GFP-bright aggregates typical of the distribution of PKAcat-EGFP seen in unstimulated cells (FIG. 5, t=0 minutes). The dispersal of these spots by forskolin+IBMX, a treatment which increases cAMP in the cells, shows that the GFP-labelled detectable probe must be interacting with the anchor probe in the co-transfected cells, because only the anchor probe can react to increased cAMP in this way (FIG. 5).

FIG. 12

CHO cells stably expressing both the anchor probe Cys1-hGrb2 and GFP-labelled detectable probe EGFP-Sos-Cterm before (a) and 5 minutes after (b) treatment with 100 nM PMA. The majority of cells in (a) have a rather general cytoplasmic and nuclear distribution of fluorescence. Treatment with PMA causes a measurable shift in fluorescence to the plasma membrane, in the same way that Cys1-EGFP would redistribute in response to PMA (FIG. 6). This result shows that the GFP-labelled detectable probe must be interacting with the anchor probe, because only the anchor probe can react to PMA in this way.

FIG. 13

Confocal fluorescence images showing CHO cells stably transfected with probe HSPDE4A1-EGFP. Images are recorded at the same microscope settings for direct comparison of intensities. The transfected cells are a clonal population derived from a single parent cell. In FIG. 13a the cells are growing in only HAM's F12 medium with 10% FBS; the GFP fluorescence is restricted to bright granule-like spots within the perinuclear cytoplasm of each cell. In FIG. 13b similar cells to those seen in FIG. 13a have been treated with 2 micromolar rolipram for 2 hours. The majority of GFP-bright spots disappear in all cells under rolipram treatment, and the cytoplasm becomes generally brighter. Larger spots do not disperse in some cells. When rolipram is washed away, the spots reform within 1.75 hours.

FIG. 14

FIG. 14 shows a dose response curve for PDE4A1 spot dispersal in response to rolipram. The number of spots per cell for each concentration of the different inhibitors is the mean of 4 measurements±sem, where each measurement is itself an average taken from not less than 100 cells. Cells are grown in HAM's F12 medium plus 10% FBS plus various concentrations of rolipram for 7 hours. The cells are then chemically fixed with 4% formalin buffer (pH7) for 15 minutes, washed with PBS and stained with 10 μM Hoechst 33258 in PBS for 10 minutes at 25° C., then washed twice in PBS. Automated images are collected and analysed for the number of spots per cell as described in Example 2.

FIG. 15

Effect of stimulating CHO cells expressing an in frame protein fusion between PDE4A4 and human 14-3-3beta and an in frame protein fusion between EGFP and human BAD. A marked appearance of spots is observed in the cells stimulated with rolipram (left panels). Extractted cells retain most of the fluorescence that is located in spots and aggregates, but lose that which is more generally distributed in the cytoplasm. This non-anchored fluorescence is presumably more mobile, and therefore rapidly washes out of the cells upon their permeabilisation.

FIG. 16

Effect of stimulating CHO cells expressing the NFkB (p65)EGFP fusion with ll-1 at 1 ng/ml. A marked redistribution from the cytosol to the nucleus is observed (left panel). Extracted cells retain most of the fluorescence originating from the nucleus, whereas fluorescence originating from the cytosol is lost (right panel).

FIG. 17

Trap assay (spots): 4A4-14-3-3b+eGFP-BAD

A: the absolute fluorescence measured.

B: the signal to noise ratio in based on the data in figure A. As can be seen, the optimal signal to noise ratio is in this case obtained with Formalin 0.8%+Triton-x100 2%.

FIG. 18

Dose response on the effect of forskolin to stimulate PKA translocation. The calculated $EC_{50}$=3.28 uM forskolin.

FIG. 19

CHO cells stably expressing HSPDE4A4B-GFP (see Example 2), and untransfected CHO cells are seeded into individual wells of a 96-well microtiter plate at a density of $1.2 \times 10^5$ cells/well, and cultured for 16 to 18 hours in HAM F-12 medium with glutamax, 100 μg penicillin-streptomycin mixture ml$^{-1}$ and 10% FBS plus various concentrations of rolipram. After the incubation period, cAMP content is measured using a commercial kit from Amersham-Pharnacia Biotech, kit # RPA538, according to the manufacturers instructions.

The amount of cAMP/well was calculated using regression analysis from a CAMP standrad curve, as recommended by the manufacturers of the assay kit. The curves for both normal untransfected CHO cells (♦), and cells stably expressing HSPDE4A4B-GFP (□) show no appreciable increase in cellular cAMP concentration over a range of rolipram treatments from 0.03 μM to 3 μM. The slight rise in cAMP in normal CHO cells at 10 μM rolipram is probably not significant.

FIG. 20

CHO cells stably expressing HSPDE4A4B-GFP (see Example 2), and untransfected CHO cells are seeded into individual wells of a 96-well microtiter plate at a density of $1.2 \times 10^5$ cells/well, and cultured for 16 to 18 hours in HAM F-12 medium with glutamax, 100 μg penicillin-streptomycin mixture ml$^{-1}$ and 10% FBS. After 16 to 18 hours incubation, cells are treated for 60 minutes with various concentrations of forskolin. After the treatment period, cAMP content is measured using a commercial kit from Amersham-Pharmacia Biotech, kit # RPA538, according to the manufacturers instructions.

The amount of cAMP/well was calculated using regression analysis from a cAMP standrad curve, as recommended by the manufacturers of the assay kit. The curve for normal untransfected CHO cells (♦) shows the expected dose-dependent increase of cellular cAMP in response to this adenylate cyclase activator. Cells stably expressing HSPDE4A4B-GFP (□) show no appreciable increase in cellular CAMP concentration over a range of forskolin treatments from 0.3 μM to 100 μM.

The invention claim is:

1. A method for detecting if a compound modulates an intracellular protein interaction comprising the steps of:
   (a) providing a cell that contains two heterologous conjugates, the first heterologous conjugate comprising a first protein of interest conjugated to a detectable group, the second heterologous conjugate comprising a second protein of interest conjugated to a phosphodiesterase type 4, isoform A, splice variant 4B (PDE4A4), said PDE4A4 being characterized to form cytoplasmic aggregates in the presence of rolipram, wherein the PDE4A4 of the second heterologous conjugate specifically binds to an internal structure within the cell;
   (b) detecting the intracellular distribution of the detectable group, wherein an intracellular distribution of said detectable group that mimics the intracellular distribution of PDE4A4 is indicative of binding between the two proteins of interest;
   (c) repeating step (b) with and without the compound;
   a change in intracellular distribution of the detectable group with and without the compound being indicative of the compound modulating said protein interaction.

2. A method according to claim 1, wherein the specific binding to the internal structure within the cell is dissolved by addition of an anchor stimulus.

3. A method according to claim 1, wherein the specific binding to the internal structure within the cell is induced by an anchor stimulus that by itself is substantially devoid of stimulating or inhibiting signaling activity within the cell of interest.

4. A method according to claim 3, wherein the specific binding is induced by addition of rolipram.

5. A method according to claim 1, wherein the detectable group is a Green Fluorescent Protein (GFP).

6. A method according to claim 5, wherein the GFP is a GFP having the F64L mutation.

7. A method according to claim 5, wherein the GFP is a GFP variant selected form the group consisting of F64L-GFP, F64L-Y66H-GFP, F64L-S65T-GFP, F64L-E22G-GFP and EGFP.

8. A method according to claim 1, further comprising contacting the cell that contains the two heterologous conjugates with rolipram; and determining that cytoplasmic aggregates form in the cell cytoplasm in response to the rolipram.

9. A method according to claim 8, wherein the cytoplasmic aggregates include the PDE4A4.

10. A method according to claim 1, further comprising contacting the cell that contains the two heterologous conjugates with rolipram; and determining that cytoplasmic aggregates do not form in the cell cytoplasm in response to the rolipram.

11. A method according to claim 1, further comprising determining that a cytoplasmic aggregate in the cell cytoplasm dissolves in response to the rolipram.

12. A method according to claim 11, wherein the cytoplasmic aggregate that dissolves in response to rolipram is devoid of PDE4A4.

13. A method according to claim 11, wherein the cytoplasmic aggregate that dissolves in response to rolipram includes PDE4A1.

* * * * *

UNITED STATES PATENT AND TRADEMARK OFFICE
CERTIFICATE OF CORRECTION

PATENT NO. : 7,282,347 B2
APPLICATION NO. : 10/332065
DATED : October 16, 2007
INVENTOR(S) : Bjorn et al.

It is certified that error appears in the above-identified patent and that said Letters Patent is hereby corrected as shown below:

Column 1
Line 46, change "characterisabon" to --characterization--

Column 2
Line 40, change "to internal" to --to the internal--

Column 3
Line 54, change "to it" to --to--
Line 66, change "aggregates is" to --aggregates are--

Column 4
Line 8, change "PKAcata" to --PKAcatα--
Line 19, change "peptde" to --peptide--

Column 5
Line 27, change "allow" to --allows--
Line 40, change "group an" to --group, an--

Column 6
Line 35, change "embodiment one" to --embodiment, one--
Line 38, change "to mitochondria" to --to the mitochondrial--
Line 60, change "it's" to --its--
Line 60, change "he" to --the--

Column 7
Line 60, change "spot like" to --spot-like--
Line 61, change "spot like" to --spot-like--
Line 63, change "spot like" to --spot-like--
Line 65, change "protein is" to --protein--

Column 8
Line 10, change "stmulus" to --stimulus--
Line 28, change "milk, urine," to --milk, or urine,--

Column 9
Line 26, change "lipidabon" to --lipidation--
Line 35, change "protein, components" to --protein components--
Line 52, change "polypepbde" to --polypeptide--

Column 10
Line 17, change "F64L-Y66H-GFP F64L-S65T-GFP" to --F64L-Y66H-GFP, F64L-S65T-GFP--
Line 32, change "groups is" to --groups are--
Line 40, change "such epitopes detectable tag such" to --epitope detectable tags are--
Line 41, change "as the myc" to --the myc--
Line 58, change "the person" to --persons--

Column 11
Line 42, change "component a" to --component, a--

Column 13
Line 17, change "In essence" to --in essence--
Line 44, change "memebrane" to --membrane--

Column 14
Line 20, change "paraformaldehyde. Most" to --or paraformaldehyde. The most--
Line 44, change "of out" to --out of--
Line 45, change "compartment to" to --components from--
Line 46, change "diffuse" to --diffusing--
Line 47, change "optimized" to --optimize--
Line 52, change "that" to --it--

Column 15
Line 10, change "comprising" to --comprises--
Line 56, change "Sammiung" to --Sammlung--

Column 16
Line 19, change "plasmis" to --plasmid--
Line 59, change "Immediately" to --immediately--

Column 17
Line 45, change "restricton" to --restriction--

Column 18
Line 59, change "4A-boftom" to --4A-bottom--

Column 19
Line 4, change "Sammiung" to --Sammlung--
Line 18, change "P3461" to --PS461--
Line 51, change "norrnal" to --normal--

Column 20
Line 27, change "90 nm" to --20 nm--
Line 67, change "fifted" to --fitted--

Column 22
Line 39, change "PKCy" to --PKCγ--

CERTIFICATE OF CORRECTION (continued)
U.S. Pat. No. 7,282,347 B2

Column 23
Line 1, change "the detectable to" to --and the detectable probe with--
Line 16, change "rolipram aggregates" to --rolipram, aggregates--

Column 25
Line 13, change "Ume" to --time--
Line 33, change "wioth" to --with--

Column 27
Line 6, change "be measurable" to --measurable--
Line 54, change "recuiting" to --recruiting--

Column 30
Line 29, change "Bemtsen" to --Berntsen--

Column 31
Line 15, change "YGFP" to --GFP--
Line 56, change ""dissolves"" to --"dissolve"--

Column 32
Line 10, change "aggregates 5" to --aggregates--
Line 40, change "standrad" to --standard--

Column 33
Line 24, change "rolipram" to --Rolipram--
Line 43, change "rolipram" to --Rolipram--
Line 62, change "I" to --1--

Column 34
Line 19, change "btrated" to --titrated--
Line 37, change "FBS plus" to --FBS--

Column 36
Line 10, change "(p65)EGFP" to --(p65)-EGFP--
Line 19, change "ratio in" to --ratio is--
Line 38, change "standrad" to --standard--
Line 60, change "standrad" to --standard--

Signed and Sealed this

Second Day of March, 2010

David J. Kappos
*Director of the United States Patent and Trademark Office*